US008623894B2

(12) United States Patent
DeMattei et al.

(10) Patent No.: US 8,623,894 B2
(45) Date of Patent: *Jan. 7, 2014

(54) SOLID FORMS OF N-[2,4-BIS(1,1-DIMETHYETHYL)-5- HYDROXYPHENYL]-1,4-DIHYDRO-4-OXOQUIOLINE-3-CARBOXAMIDE

(71) Applicant: Vertex Pharmaceuticals Incorporated, Cambridge, MA (US)

(72) Inventors: John DeMattei, Berthoud, CO (US); Yushi Feng, Zionsville, IN (US); Cristian L. Harrison, Beverly, MA (US); Adam R. Looker, Cambridge, MA (US); Praveen Mudunuri, Waltham, MA (US); Stefanie Roeper, Medford, MA (US); Yuegang Zhang, Wayland, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/714,911

(22) Filed: Dec. 14, 2012

(65) Prior Publication Data

US 2013/0109717 A1      May 2, 2013

Related U.S. Application Data

(63) Continuation of application No. 13/413,327, filed on Mar. 6, 2012, now Pat. No. 8,362,253, which is a continuation of application No. 12/283,702, filed on Sep. 15, 2008, now Pat. No. 8,163,772.

(60) Provisional application No. 60/972,605, filed on Sep. 14, 2007.

(51) Int. Cl.
*A61K 31/04*        (2006.01)

(52) U.S. Cl.
USPC .......................................................... 514/312

(58) Field of Classification Search
USPC .......................................................... 514/312
See application file for complete search history.

(56) References Cited

U.S. PATENT DOCUMENTS

| 7,495,103 B2 | 2/2009 | Hadida-Ruah et al. |
| 8,163,772 B2 * | 4/2012 | DeMattei et al. ............. 514/312 |
| 8,362,253 B2 * | 1/2013 | DeMattei et al. ............. 546/159 |
| 2010/0074949 A1 | 3/2010 | Rowe et al. |
| 2010/0256184 A1 | 10/2010 | Rowe et al. |
| 2010/0267768 A1 | 10/2010 | DeMattei et al. |

FOREIGN PATENT DOCUMENTS

| WO | 2006002421 A2 | 1/2006 |
| WO | 2007079139 A2 | 7/2007 |

OTHER PUBLICATIONS

International Search Report for PCT/US2008/010728, dated Jul. 6, 2010.
Written Opinion for PCT/US2008/010728, dated Jul. 6, 2010.

* cited by examiner

*Primary Examiner* — D M Seaman
(74) *Attorney, Agent, or Firm* — Honigman Miller Schwartz and Cohn LLP; Christopher C. Forbes; Jonathan P. O'Brien

(57) ABSTRACT

Solid forms of N-[2,4-bis(1,1-dimethylethyl)-5-hydroxyphenyl]-1,4-dihydro-4-oxoquinoline-3-carboxamide are described herein, including crystalline forms thereof.

3 Claims, 52 Drawing Sheets

DSC

TGA

SOLID FORMS OF N-[2,4-BIS(1,1-DIMETHYETHYL)-5-HYDROXYPHENYL]-1,4-DIHYDRO-4-OXOQUIOLINE-3-CARBOXAMIDE

CROSS-REFERENCE

This application is a continuation of U.S. application Ser. No. 13/413,327, filed Mar. 6, 2012 now U.S. Pat. No. 8,362,253, issued Jan. 29, 2013, which is a continuation of U.S. application Ser. No. 12/283,702, filed Sep. 15, 2008, now U.S. Pat. No. 8,163,772, issued on Apr. 24, 2012, which claims priority under 35 USC §119(e) to U.S. Application No. 60/972,605, filed on Sep. 14, 2007. The entire contents of each of the aforementioned applications are incorporated herein.

TECHNICAL FIELD

This invention relates to solid forms of N-[2,4-bis(1,1-dimethylethyl)-5-hydroxyphenyl]-1,4-dihydro-4-oxoquinoline-3-carboxamide.

BACKGROUND

N-[2,4-bis(1,1-dimethylethyl)-5-hydroxyphenyl]-1,4-dihydro-4-oxoquinoline-3-carboxamide (hereinafter "Compound 1") has the structure below:

Compound 1

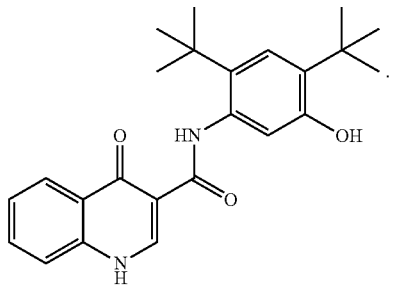

Compound 1 is described and claimed in International PCT publication WO 2006002421 and has the following molecular formula: $C_{24}H_{28}N_2O_3$.

Compound 1 has been demonstrated to restore the function of the cystic fibrosis transmembrane conductance regulator (CFTR) protein, the defective cell membrane protein responsible for the progression of CF. Defects in the CFTR protein can affect the transport of chloride and other ions across cells, and lead to the accumulation of thick, sticky mucus in the lungs of patients with CF. This mucus can foster chronic infection and inflammation, and can result in irreversible lung damage. Potentiator compounds such as Compound 1 can increase the probability that the CFTR channel is open, which could result in an increase in chloride transport across the cell surface in some patients. In laboratory experiments, using cells from patients with CF where CFTR proteins are present on the cell surface, Compound 1 has restored the function of defective CFTR channels.

SUMMARY

Solid forms of Compound 1 are described herein. The properties of a solid relevant to its efficacy as a drug can be dependent on the form of the solid. For example, in a drug substance, variation in the solid form can lead to differences in properties such as dissolution rate, oral absorption, bioavailability, toxicology results and even clinical trial results. In some embodiments, the solid forms of Compound 1 are co-forms, for example, salts, solvates, co-crystals and hydrates of Compound 1.

Isotopically-labeled forms of Compound 1 wherein one or more atoms are replaced by an atom having an atomic mass or mass number different from the atomic mass or mass number usually found in nature are also included herein. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, and $^{17}O$. Such radiolabelled and stable-isotopically labelled compounds are useful as research or diagnostic tools.

In one aspect, the invention features Compound 1.2-methylbutyric acid, for example, crystalline Compound 1.2-methylbutyric acid. In some embodiments, the crystalline Compound 1.2-methylbutyric acid has a ratio of 1:1.

In some embodiments, the crystalline Compound 1.2-methylbutyric acid is characterized by one or more of the following X-ray powder diffraction peaks (all peaks referred to herein are measured in degrees): a peak from about 5.6 to about 6.0 (e.g., about 5.8), a peak from about 6.5 to about 6.9 (e.g., about 6.7), a peak from about 8.6 to about 9.0 (e.g., about 8.8), a peak from about 9.9 to about 10.3 (e.g., about 10.1), a peak from about 10.3 to about 10.7 (e.g., about 10.5), a peak from about 11.2 to about 11.6 (e.g., about 11.4), a peak from about 13.7 to about 14.1 (e.g., about 13.9), a peak from about 15.1 to about 15.5 (e.g., about 15.3), a peak from about 16.7 to about 17.1 (e.g., about 16.9), a peak from about 17.2 to about 17.6 (e.g., about 17.4), a peak from about 20.2 to about 20.6 (e.g., about 20.2), or a peak from about 8.6 to about 9.0 (e.g., about 8.8). In some preferred embodiments, the crystalline Compound 1.2-methylbutyric acid is characterized by at least the following X-ray powder diffraction peaks: 5.8, 6.7, and 8.8. In some embodiments, the crystalline Compound 1.2-methylbutyric acid, is characterized by a X-ray ray powder diffraction pattern substantially similar to the X-ray powder diffraction pattern provided in FIG. 1.

In some embodiments, the crystalline Compound 1.2-methylbutyric acid has a triclinic crystal system. In some embodiments, the crystalline Compound 1.2-methylbutyric acid has a P-1 space group. In some embodiments, the crystalline Compound 1.2-methylbutyric acid has the following unit cell dimensions when measured in Å at 120K:
 a=about 10.3 to about 10.7 (e.g., about 10.5)
 b=about 16.0 to about 16.4 (e.g., about 16.2)
 c=about 17.5 to about 17.9 (e.g., about 17.7).

In some embodiments, the crystalline Compound 1.2-methylbutyric acid is characterized by a weight loss from about 20 to about 22% in a temperature range of from about 60° C. to about 198° C.

In one aspect, the invention features a pharmaceutical preparation of Compound 1.2-methylbutyric acid, e.g., crystalline Compound 1.2-methylbutyric acid. In some embodiments, the pharmaceutical preparation is substantially free of other solid forms of Compound 1.

In some embodiments, the crystalline Compound 1.2-methylbutyric acid is part of a pharmaceutical preparation, for example, a pharmaceutical preparation substantially free of other solid forms of Compound 1.

In one aspect, the invention features a method of making crystalline Compound 1.2-methylbutyric acid. The method includes:
 dissolving Compound 1 in 2-methyl butyric acid and then cooling the solution of Compound 1 and methyl butyric acid to provide crystalline Compound 1.2-methylbutyric acid. In some embodiments, the Compound 1 is dissolved in hot methyl butyric acid.

In one aspect, the invention features Compound 1.propylene glycol, for example, crystalline Compound 1.propylene glycol. In some embodiments, the crystalline Compound 1.propylene glycol has a ratio of the Compound 1:propylene glycol of 1:1.

In some embodiments, the crystalline Compound 1.propylene glycol is characterized by one or more of the following X-ray powder diffraction pattern peaks (all peaks referred to herein are measured in degrees): a peak from about 9.9 to about 10.3 (e.g., about 10.1), a peak from about 11.5 to about 11.9 (e.g., about 11.7), a peak from about 11.9 to about 12.3 (e.g., about 12.1), a peak from about 13.1 to about 13.5 (e.g., about 13.3), a peak from about 13.5 to about 13.9 (e.g., about 13.7), a peak from about 14.0 to about 14.4 (e.g., about 14.2), a peak from about 15.3 to about 15.7 (e.g., about 15.5), a peak from about 17.9 to about 18.3 (e.g., about 18.1), a peak from about 19.2 to about 19.6 (e.g., about 19.4), a peak from about 20.3 to about 20.7 (e.g., about 20.5), a peak from about 22.4 to about 22.8 (e.g., about 22.6), a peak from about 24.4 to about 24.8 (e.g., about 24.6), or a peak from about 24.8 to about 25.2 (e.g., about 25.0). In some preferred embodiments, the compound is characterized by at least the following peaks: 10.1, 18.1, and 20.1.

In some embodiments, the crystalline Compound 1.propylene glycol, is characterized by an X-ray powder diffraction pattern substantially similar to the provided in FIG. 5.

In some embodiments, the crystalline Compound 1.propylene glycol is characterized by a weight loss of from about 16 to about 17% with an onset temperature of about 144° C.

In one aspect, the invention features a method of making crystalline Compound 1.propylene glycol. The method includes dissolving Compound 1 in propylene glycol and then cooling the solution of Compound 1 and propylene glycol to provide crystalline Compound 1.propylene glycol. In some embodiments, the Compound 1 is dissolved in hot propylene glycol. In some embodiments, the method further includes rinsing the crystalline Compound 1.propylene glycol with a polar aprotic solvent, for example, acetone.

In one aspect, the invention features a pharmaceutical preparation of Compound 1.propylene glycol, e.g., crystalline Compound 1.propylene glycol. In some embodiments, the pharmaceutical preparation is substantially free of other solid forms of Compound 1.

In one aspect, the invention features Compound 1.PEG. In some embodiments the Compound 1.PEG further comprises a salt, for example, a carboxylate salt such as an acetate salt (e.g., sodium, potassium, or calcium). In some embodiments the PEG is a PEG from about PEG 200 to about PEG 2000, e.g., PEG 400 or PEG 600.

In one aspect, the invention features Compound 1.PEG 400.KOAc, for example, crystalline Compound 1.PEG 400.KOAc. In some embodiments, the crystalline Compound 1.PEG 400.KOAc has a ratio of the Compound 1:PEG 400.KOAc of 2:1:1:1.

In some embodiments, the crystalline Compound 1.PEG 400.KOAc is characterized by one or more of the following X-ray powder diffraction pattern peaks(all peaks referred to herein are measured in degrees): a peak from about 6.0 to about 6.4 (e.g., about 6.2), a peak from about 7.9 to about 8.3 (e.g., about 8.1), a peak from about 9.5 to about 9.9 (e.g., about 9.7), a peak from about 12.0 to about 12.4 (e.g., about 12.2), a peak from about 12.9 to about 13.3 (e.g., about 13.1), a peak from about 13.5 to about 13.9 (e.g., about 13.7), a peak from about 14.2 to about 14.6 (e.g., about 14.4), a peak from about 16.1 to about 16.5 (e.g., about 16.3), a peak from about 16.7 to about 17.1 (e.g., about 16.9), a peak from about 18.3 to about 18.7 (e.g., about 18.5), a peak from about 19.0 to about 19.4 (e.g., about 19.2), or a peak from about 20.3 to about 20.7 (e.g., about 20.5). In some preferred embodiments, the Crystalline Compound 1.PEG 400.KOAc is characterized by at least the following peaks: 6.2, 12.2, and 13.7. In some embodiments, the crystalline Compound 1.PEG 400.KOAc is characterized by an X-ray powder diffraction pattern substantially similar to the X-ray powder diffraction pattern provided in FIG. 9.

In some embodiments, the crystalline Compound 1.PEG 400.KOAc has a monoclinic crystal system. In some embodiments, the crystalline Compound 1.PEG 400.KOAc has a P2/n space group.

In some embodiments, the crystalline Compound 1.PEG 400.KOAc has the following unit cell dimensions as measured in Å when measured at 120K
a=about 14.3 to about 14.7 (e.g., about 14.5)
b=about 14.3 to about 14.7 (e.g., about 14.5)
c=about 16.3 to about 16.7 (e.g., about 16.5).

In some embodiments, the crystalline Compound 1.PEG 400.KOAc is characterized by a weight loss of from about 1 to about 2% with an onset temperature of from about 140° C. to about 172° C.

In one aspect, the invention features a method of making crystalline Compound 1.PEG 400.KOAc. The method includes dissolving Compound 1 in a mixture of PEG and KOAc, and then cooling the resulting mixture to provide crystalline Compound 1.PEG 400.KOAc. In some embodiments, the solution also includes PVP.

In one aspect, the invention features a method of making crystalline Compound 1.PEG 400.KOAc. The method includes providing a mixture of crystalline Compound 1, PEG, and KOAc, stirring the mixture and cooling the mixture to provide crystalline crystalline Compound 1.PEG 400.KOAc. In some embodiments, the mixture also includes ethyl acetate.

In one aspect, the invention features a pharmaceutical preparation of Compound 1.PEG 400.KOAc, e.g., crystalline Compound 1.PEG 400.KOAc. In some embodiments, the pharmaceutical preparation is substantially free of other solid forms of Compound 1.

In one aspect, the invention features Compound 1.lactic acid, for example, crystalline Compound 1.lactic acid. In some embodiments, the crystalline Compound 1.lactic acid has a ratio of Compound 1:lactic acid of 1:1.

In some embodiments, the crystalline Compound 1.lactic acid is characterized by one or more of the following X-ray powder diffraction pattern a peaks(all peaks referred to herein are measured in degrees): a peak at from about 7.1 to about 7.5 (e.g., about 7.3), a peak at from about 11.1 to about 11.5 (e.g., about 11.3), a peak at from about 7.1 to about 7.5 (e.g., about 7.3), a peak at from about 13.2 to about 13.6 (e.g., about 13.4), a peak at from about 14.2 to about 14.6 (e.g., about 14.4), a peak at from about 15.2 to about 15.6 (e.g., about 15.4), a peak at from about 17.0 to about 17.4 (e.g., about 17.2), a peak at from about 17.8 to about 18.2 (e.g., about 18.0), a peak at from about 18.5 to about 18.9 (e.g., about 18.7), a peak at from about 19.3 to about 19.7 (e.g., about 19.5), or a peak at from about 21.5 to about 21.9 (e.g., about 21.7). In some preferred embodiments, the crystalline Compound 1.lactic acid includes at least the following characteristic peaks: 7.3, 11.3, and 21.7. In some embodiments, the crystalline Compound 1.lactic acid, is characterized by an X-ray powder diffraction pattern substantially similar to the an X-ray powder diffraction pattern provided in FIG. 13.

In some embodiments, the crystalline Compound 1.lactic acid has a triclinic crystal system. In some embodiments, the crystalline Compound 1.lactic acid of has a P-1 space group. In some embodiments, the crystalline Compound 1.lactic acid has the following unit cell dimensions as measured in Å at 100K a=about 8.9 to about 9.3 (e.g., about 9.1)
b=about 11.7 to about 12.1 (e.g., about 11.9)
c=about 12.1 to about 12.5 (e.g., about 12.3).

In some embodiments, the crystalline Compound 1.lactic acid is characterized by a weight loss of from about 20 to about 21% with an onset temperature of about 173° C.

In one aspect, the invention features a method of making crystalline Compound 1.lactic acid. The method includes dissolving Compound 1 and lactic acid in acetonitrile, and evaporating at least a portion of the acetonitrile to provide crystalline Compound 1.lactic acid In one aspect, the invention features a pharmaceutical preparation comprising Compound 1.lactic acid, e.g., crystalline Compound 1.lactic acid. In some embodiments, the pharmaceutical preparation is substantially free of other forms of Compound 1.

In one aspect, the invention features Compound 1.isobutyric acid, for example, crystalline Compound 1.isobutyric acid. In some embodiments, the crystalline Compound 1.isobutyric acid of has a ratio of Compound 1:isobutyric acid of 1:2.

In some embodiments, the crystalline Compound 1.isobutyric acid us characterized by one or more of the following X-ray powder diffraction pattern peaks (all peaks referred to herein are measured in degrees): a peak at from about 5.0 to about 5.4 (e.g., about 5.2), a peak at from about 6.3 to about 6.7 (e.g., about 6.5), a peak at from about 9.2 to about 9.6 (e.g., about 9.4), a peak at from about 10.1 to about 10.5 (e.g., about 10.3), a peak at from about 12.4 to about 12.8 (e.g., about 12.6), a peak at from about 13.1 to about 13.5 (e.g., about 13.3), a peak at from about 14.0 to about 14.4 (e.g., about 14.2), a peak at from about 14.8 to about 15.2 (e.g., about 15.0), a peak at from about 15.3 to about 15.7 (e.g., about 15.5), a peak at from about 15.8 to about 16.2 (e.g., about 16.0), a peak at from about 17.8 to about 18.2 (e.g., about 18.0), a peak at from about 18.2 to about 18.6 (e.g., about 18.4), a peak at from about 18.6 to about 19.0 (e.g., about 18.8), a peak at from about 19.2 to about 19.6 (e.g., about 19.4), a peak at from about 19.7 to about 20.1 (e.g., about 19.9), a peak at from about 20.5 to about 20.9 (e.g., about 20.7), a peak at from about 21.0 to about 21.4 (e.g., about 21.2), a peak at from about 25.1 to about 25.5 (e.g., about 25.3), or a peak at from about 27.4 to about 27.8 (e.g., about 27.6). In some preferred embodiments, the crystalline Compound 1.isobutyric acid includes the following characteristic peaks: 5.2, 6.5, and 9.4. In some embodiments, the crystalline Compound 1.isobutyric acid, has a X-ray powder diffraction pattern substantially similar to the X-ray powder diffraction pattern provided in FIG. 17.

In some embodiments, the crystalline Compound 1.isobutyric acid has a triclinic crystal system. In some embodiments, the crystalline Compound 1.isobutyric acid has a P-1 space group. In some embodiments, the crystalline Compound 1.isobutyric acid has the following unit cell dimensions as measured in Å at 100K a=about 13.1 to about 13.5 (e.g., about 13.3)
b=about 14.6 to about 15.0 (e.g., about 14.8)
c=about 18.0 to about 18.4 (e.g., about 18.2).

In some embodiments, the crystalline Compound 1.isobutyric acid is characterized by a weight loss of from about 30 to about 31% with an onset temperature of about 60° C. to about 184° C.

In one aspect, the invention features a method of making crystalline Compound 1.isobutyric acid. The method includes dissolving Compound 1 in isobutryic acid, and cooling the solution of Compound 1 and isobutryic acid to provide crystalline Compound 1.isobutyric acid. In some embodiments, the Compound 1 is dissolved into hot isobutyric acid.

In one aspect, the invention features a pharmaceutical preparation comprising Compound 1.isobutyric acid, e.g., crystalline Compound 1.isobutyric acid. In some embodiments, the pharmaceutical preparation is substantially free of other forms of Compound 1.

In one aspect, the invention features Compound 1.propionic acid, for example, crystalline Compound 1.propionic acid. In some embodiments, the crystalline Compound 1.propionic acid has a ratio of Compound 1:propionic acid of 1:2.

In some embodiments, the crystalline Compound 1.propionic acid is characterized by at least one of the following X-ray powder diffraction pattern peaks (all peaks referred to herein are measured in degrees): a peak at from about 5.1 to about 5.5 (e.g., about 5.3), a peak at from about 6.9 to about 7.3 (e.g., about 7.1), a peak at from about 10.1 to about 10.5 (e.g., about 10.3), a peak at from about 10.5 to about 10.9 (e.g., about 10.7), a peak at from about 12.9 to about 13.3 (e.g., about 13.1), a peak at from about 15.8 to about 16.2 (e.g., about 16.0), a peak at from about 18.6 to about 19.0 (e.g., about 18.8), a peak at from about 19.5 to about 19.9 (e.g., about 19.7), or a peak at from about 19.9 to about 20.3 (e.g., about 20.1). In some preferred embodiments, the Crystalline Compound 1.propionic acid is characterized by at least the following peaks: 5.3, 7.1, and 10.3. In some embodiments, the crystalline Compound 1.propionic acid, having an X-ray powder diffraction pattern substantially similar to the X-ray powder diffraction pattern provided in FIG. 21.

In some embodiments, the crystalline Compound 1.propionic acid has a triclinic crystal system. In some embodiments, the crystalline Compound 1.propionic acid has a P-1 space group. In some embodiments, the crystalline Compound 1.propionic acid of claim 1, having the following unit cell dimensions as measured in Å as measured at 100K a=about 6.6 to about 7.0 (e.g., about 6.8)
b=about 13.0 to about 13.4 (e.g., about 13.2)
c=about 17.4 to about 17.8 (e.g., about 17.6).

In some embodiments, the crystalline Compound 1.propionic acid s characterized by a weight loss of from about 26 to about 27% with an onset temperature of about 60° C. to about 160° C.

In one aspect, the invention features a method of making crystalline Compound 1.propionic acid. The method includes dissolving Compound 1 in propionic acid, and cooling the solution of Compound 1 and propionic acid to provide crystalline Compound 1.propionic acid. In some embodiments, the Compound 1 is dissolved into hot propionic acid.

In one aspect, the invention features a pharmaceutical preparation comprising Compound 1.propionic acid, e.g., crystalline Compound 1.propionic acid. In some embodiments, the pharmaceutical preparation is substantially free of other forms of Compound 1.

In one aspect, the invention features Compound 1.EtOH, for example, crystalline Compound 1.EtOH. In some embodiments, the crystalline Compound 1.EtOH has a ratio of Compound 1:EtOH of 1:1.5.

In some embodiments, the crystalline Compound 1.EtOH is characterized by at least one of the following X-ray powder diffraction pattern a peaks (all peaks referred to herein are measured in degrees): a peak at from about 6.0 to about 6.4 (e.g., about 6.2), a peak at from about 10.2 to about 10.6 (e.g., about 10.4), a peak at from about 12.2 to about 12.6 (e.g., about 12.4), a peak at from about 13.4 to about 13.8 (e.g., about 13.6), a peak at from about 14.1 to about 14.5 (e.g., about 14.3), a peak at from about 14.9 to about 15.3 (e.g., about 15.1), a peak at from about 15.4 to about 15.8 (e.g., about 15.6), a peak at from about 17.7 to about 18.1 (e.g., about 17.9), a peak at from about 18.4 to about 18.8 (e.g., about 18.6), a peak at from about 19.8 to about 20.2 (e.g., about 20.2), a peak at from about 22.6 to about 23.0 (e.g., about 22.8), a peak at from about 23.8 to about 24.2 (e.g., about 24.0), a peak at from about 24.8 to about 25.2 (e.g., about 25.0), a peak at from about 27.4 to about 27.8 (e.g., about 27.6), or a peak at from about 32.4 to about 32.8 (e.g., about 32.6). In some preferred embodiments, the crystalline Compound 1.EtOH has at least the following characteristic peaks: 6.2, 10.4, and 12.4. In some embodiments, the crystalline Compound 1.EtOH, has a X-ray powder diffraction pattern substantially similar to the provided in FIG. 25.

In some embodiments, the crystalline Compound 1.EtOH has a monoclinic crystal system. In some embodiments, the crystalline Compound 1.EtOH has a P2/n space group. In some embodiments the crystalline Compound 1.EtOH has the following unit cell dimensions as measured in Å at 100K
    a=about 16.4 to about 16.8 (e.g., about 16.6)
    b=about 9.7 to about 10.1 (e.g., about 9.9)
    c=about 17.0 to about 17.4 (e.g., about 17.2).

In some embodiments, the crystalline Compound 1.EtOH is characterized by a weight loss of from about 13 to about 15% with an onset temperature of about 60° C. to about 121° C.

In one aspect, the invention features a method of making crystalline Compound 1.EtOH. The method includes dissolving Compound 1 in EtOH, and cooling the solution of Compound 1 and EtOH to provide crystalline Compound 1.EtOH. In some embodiments, the Compound 1 is dissolved into hot EtOH.

In one aspect, the invention features a pharmaceutical preparation comprising Compound 1.EtOH, e.g., crystalline Compound 1.EtOH. In some embodiments, the pharmaceutical preparation is substantially free of other forms of Compound 1.

In one aspect, the invention features Compound 1.2-propanol, for example, crystalline Compound 1.2-propanol. In some embodiments, the crystalline Compound 1.2-propanol has a ratio of Compound 1:2-propanol of 1:1.5.

In some embodiments, the Crystalline Compound 1.2-propanol is characaterized by one or more of the following X-ray powder diffraction pattern peaks (all peaks referred to herein are measured in degrees): a peak at from about 6.0 to about 6.4 (e.g., about 6.2), a peak at from about 10.1 to about 10.5 (e.g., about 10.3), a peak at from about 12.1 to about 12.5 (e.g., about 12.3), a peak at from about 10.1 to about 10.5 (e.g., about 10.3), a peak at from about 13.3 to about 13.7 (e.g., about 13.5), a peak at from about 13.8 to about 14.2 (e.g., about 14.0), a peak at from about 14.9 to about 15.3 (e.g., about 15.1), a peak at from about 18.3 to about 18.7 (e.g., about 18.5), a peak at from about 20.5 to about 20.9 (e.g., about 20.7), a peak at from about 22.3 to about 22.7 (e.g., about 22.5), or a peak at from about 23.6 to about 24.0 (e.g., about 23.8). In some preferred embodiments, the crystalline Compound 1.2-propanol has at least the following characteristic peaks: 6.2, 10.3, and 12.3. In some embodiments, the crystalline Compound 1.2-propanol, has an X-ray powder diffraction pattern substantially similar to the X-ray powder diffraction pattern provided in FIG. 29.

In some embodiments, the crystalline Compound 1.2-propanol has a monoclinic crystal system. In some embodiments, the crystalline Compound 1.2-propanol has a P2/n space group. In some embodiments, the crystalline Compound 1.2-propanol has the following unit cell dimensions as measured in Å at 100K
    a=about 16.8 to about 17.2 (e.g., about 17.0)
    b=about 9.7 to about 10.1 (e.g., about 9.9)
    c=about 17.1 to about 17.5 (e.g., about 17.3).

In some embodiments, the crystalline Compound 1.2-propanol is characterized by a weight loss of from about 18 to about 19% with an onset temperature of about 60° C. to about 201° C.

In one aspect, the invention features a method of making crystalline Compound 1.2-propanol. The method includes dissolving Compound 1 in 2-propanol, and cooling the solution of Compound 1 and 2-propanol to provide crystalline Compound 1.2-propanol. In some embodiments, the Compound 1 is dissolved into hot 2-propanol.

In one aspect, the invention features a pharmaceutical preparation comprising Compound 1.2-propanol, e.g., crystalline Compound 1.2-propanol. In some embodiments the pharmaceutical preparation is substantially free of other forms of Compound 1.

In one aspect, the invention features Compound $1.H_2O$, for example, crystalline Compound $1.H_2O$. In some embodiments, the crystalline Compound $1.H_2O$ has a ratio of Compound $1:H_2O$ of 1:1.

In some embodiments, the Crystalline Compound $1.H_2O$ is characterized by at least one of the following X-ray powder diffraction pattern peaks (all peaks referred to herein are measured in degrees): a peak from about 6.0 to about 6.4 (e.g., about 6.2), a peak from about 7.4 to about 7.8 (e.g., about 7.6), a peak from about 8.2 to about 8.6 (e.g., about 8.4), a peak from about 10.8 to about 11.2 (e.g., about 11.0), a peak from about 12.1 to about 12.5 (e.g., about 12.3), a peak from about 14.6 to about 15.0 (e.g., about 14.8), a peak from about 15.9 to about 16.3 (e.g., about 16.1), a peak from about 16.9 to about 17.3 (e.g., about 17.1), a peak from about 17.8 to about 18.2 (e.g., about 18.0), a peak from about 18.3 to about 18.7 (e.g., about 18.5), a peak from about 19.2 to about 19.6 (e.g., about 19.4), a peak from about 20.8 to about 21.2 (e.g., about 21.0), a peak from about 22.3 to about 22.7 (e.g., about 22.5), a peak from about 23.2 to about 23.6 (e.g., about 23.4), a peak from about 23.7 to about 24.1 (e.g., about 23.9), a peak from about 24.7 to about 25.1 (e.g., about 24.9), a peak from about 25.3 to about 25.7 (e.g., about 25.5), a peak from about 26.5 to about 26.9 (e.g., about 26.7), a peak from about 27.3 to about 27.7 (e.g., about 27.5), a peak from about 29.4 to about 29.8 (e.g., about 29.6), a peak from about 33.3 to about 33.7 (e.g., about 33.5), or a peak from about 36.6 to about 37.0 (e.g., about 36.8). In some embodiments the crystalline Compound $1.H_2O$, has an X-ray powder diffraction pattern substantially similar to the X-ray powder diffraction pattern provided in FIG. 33.

In one aspect, the invention features a method of making crystalline Compound $1.H_2O$. The method includes suspending Compound 1 in $H_2O$, and stirring the suspension of Compound 1 and $H_2O$ to provide crystalline Compound $1.H_2O$. In some embodiments, the method also includes filtering the suspension of Compound 1 and $H_2O$.

In one aspect, the invention features Compound 1.besylate, for example, crystalline Compound 1.besylate. In some embodiments, the crystalline Compound 1.besylate has a ratio of Compound 1:besylate of 1:1. In other embodiments, the crystalline Compound 1.besylate has a ratio of Compound 1:besylate of 2:1.

In some embodiments, when the crystalline Compound 1.besylate has a ratio of Compound 1:besylate of 1:1, the Compound 1.besylate may complex into distinctive crystalline forms, e.g., FORMS A, B, D, E, and F described below.

In some embodiments, the crystalline Compound 1.besylate, having a 1 to 1 ratio of Compound 1 to besylate, is characterized by one or more of the following peaks as measured in degrees in an X-ray powder diffraction pattern: a peak from about 6.8 to about 7.2 (e.g., about 7.0), a peak from about 12.7 to about 13.1 (e.g., about 12.9), a peak from about 13.6 to about 14.0 (e.g., about 13.8), a peak from about 16.2 to about 16.6 (e.g., about 16.4), a peak from about 18.5 to about 18.9 (e.g., about 18.7), a peak from about 20.9 to about 21.3 (e.g., about 21.1), a peak from about 21.8 to about 22.2 (e.g., about 22.0). In some embodiments, the crystalline Compound 1.besylate is characterized by at least the following peaks: 7.0, 13.8, 18.7, 21.1, and 22.0.

In some embodiments the crystalline Compound 1.besylate, has an X-ray powder diffraction pattern substantially similar to the X-ray powder diffraction pattern provided in FIG. 36.

In some embodiments, the crystalline Compound 1.besylate, having a 1 to 1 ratio of Compound 1 to besylate, is characterized by one or more of the following peaks as measured in degrees in an X-ray powder diffraction pattern: a peak from about 6.0 to about 6.4 (e.g., about 6.2), a peak from about 10.5 to about 10.9 (e.g., about 10.7), a peak from about 12.6 to about 13.0 (e.g., about 12.8), a peak from about 13.4 to about 13.8 (e.g., about 13.6), a peak from about 15.0 to about 15.4 (e.g., about 15.0), a peak from about 17.3 to about 17.7 (e.g., about 17.5), a peak from about 18.9 to about 19.3 (e.g., about 19.1), a peak from about 19.8 to about 20.2 (e.g., about 20.0), a peak from about 20.8 to about 21.2 (e.g., about 21.0), and a peak from about 28.7 to about 29.1 (e.g., about 28.9). In some embodiments, the crystalline Compound 1.besylate is characterized by at least the following peaks: 6.2, 15.2, 17.5, 21.0, and 28.9.

In some embodiments the crystalline Compound 1.besylate, has an X-ray powder diffraction pattern substantially similar to the X-ray powder diffraction pattern provided in FIG. 38.

In some embodiments, the crystalline Compound 1.besylate, having a 1 to 1 ratio of Compound 1 to besylate, is characterized by one or more of the following peaks as measured in degrees in an X-ray powder diffraction pattern: a peak from about 6.6 to about 7.0 (e.g., about 6.8), a peak from about 12.4 to about 12.8 (e.g., about 12.6), a peak from about 13.2 to about 13.6 (e.g., about 13.4), a peak from about 14.8 to about 15.2 (e.g., about 15.0), a peak from about 15.8 to about 16.2 (e.g., about 16.0), a peak from about 17.6 to about 18.0 (e.g., about 17.8), a peak from about 18.7 to about 19.1 (e.g., about 18.9), a peak from about 21.0 to about 21.4 (e.g., about 21.2), a peak from about 23.3 to about 23.7 (e.g., about 23.5), and a peak from about 29.7 to about 30.1 (e.g., about 29.9). In some embodiments, the crystalline Compound 1.besylate is characterized by at least the following peaks: 6.8, 12.6, 15.0, 17.8, and 18.9.

In some embodiments the crystalline Compound 1.besylate, has an X-ray powder diffraction pattern substantially similar to the X-ray powder diffraction pattern provided in FIG. 40.

In some embodiments, the crystalline Compound 1.besylate, having a 1 to 1 ratio of Compound 1 to besylate, is characterized by one or more of the following peaks as measured in degrees in an X-ray powder diffraction pattern: a peak from about 3.2 to about 3.6 (e.g., about 3.4), a peak from about 6.5 to about 6.9 (e.g., about 6.7), a peak from about 12.2 to about 12.6 (e.g., about 12.4), a peak from about 14.6 to about 15.0 (e.g., about 14.8), a peak from about 16.5 to about 16.9 (e.g., about 16.7), a peak from about 17.2 to about 17.6 (e.g., about 17.4), a peak from about 18.0 to about 18.4 (e.g., about 18.2), a peak from about 18.6 to about 19.0 (e.g., about 18.8), a peak from about 20.0 to about 20.4 (e.g., about 20.2), a peak from about 20.9 to about 21.3 (e.g., about 21.1), and a peak from about 23.2 to about 23.6 (e.g., about 23.4). In some embodiments, the crystalline Compound 1.besylate is characterized by at least the following peaks: 3.4, 6.7, 12.4, 12.6, 14.8, 18.2, and 18.8.

In some embodiments the crystalline Compound 1.besylate, has an X-ray powder diffraction pattern substantially similar to the X-ray powder diffraction pattern provided in FIG. 43.

In some embodiments, the crystalline Compound 1.besylate, having a 1 to 1 ratio of Compound 1 to besylate, is characterized by one or more of the following peaks as measured in degrees in an X-ray powder diffraction pattern: a peak from about 6.3 to about 6.7 (e.g., about 6.5), a peak from about 9.2 to about 9.6 (e.g., about 9.4), a peak from about 11.8 to about 12.2 (e.g., about 12.0), a peak from about 12.5 to about 12.9 (e.g., about 12.7), a peak from about 13.0 to about 13.4 (e.g., about 13.2), a peak from about 15.5 to about 15.9 (e.g., about 15.7), a peak from about 16.3 to about 16.7 (e.g., about 16.5), a peak from about 16.7 to about 17.1 (e.g., about 16.9), a peak from about 17.1 to about 17.5 (e.g., about 17.3), a peak from about 17.7 to about 18.1 (e.g., about 17.9), a peak from about 18.4 to about 18.8 (e.g., about 18.6), a peak from about 19.5 to about 19.9 (e.g., about 19.7), a peak from about 23.8 to about 24.2 (e.g., about 24.0), and a peak from about 26.4 to about 26.8 (e.g., about 26.6). In some embodiments, the crystalline Compound 1.besylate is characterized by at least the following peaks: 6.5, 16.5, 18.6, 19.7 and 24.0.

In some embodiments the crystalline Compound 1.besylate, has an X-ray powder diffraction pattern substantially similar to the X-ray powder diffraction pattern provided in FIG. 46.

In some embodiments, the crystalline Compound 1.besylate, having a 1 to 1 ratio of Compound 1 to besylate, has a triclinic crystal system. In some embodiments, the crystalline Compound 1.besylate, having a 1 to 1 ratio of Compound 1 to besylate, has a P-1 bar space group.

In some embodiments, the crystalline Compound 1.besylate, in which the ratio of Compound 1 to besylate having a 1 to 1, has the following unit cell dimensions as measured in Å at 120K a=about 13.3 to about 13.7 (e.g., about 13.5)
b=about 14.0 to about 14.4 (e.g., about 14.2)
c=about 15.5 to about 15.9 (e.g., about 15.7).

In some embodiments, the crystalline Compound 1.besylate, having a 1 to 1 ratio of Compound 1 to besylate, has a monoclinic crystal system. In some embodiments, the crystalline Compound 1.besylate, having a 1 to 1 ratio of Compound 1 to besylate, has a $P2_1/n$ space group.

In some embodiments, the crystalline Compound 1.besylate, in which the ratio of Compound 1 to besylate is 1 to 1, has the following unit cell dimensions as measured in Å at 120K a=about 10.7 to about 11.1 (e.g., about 10.9)
b=about 53.0 to about 53.4 (e.g., about 53.2)
c=about 11.1 to about 11.5 (e.g., about 11.3).

In some embodiments, the crystalline Compound 1.besylate, having a 2 to 1 ratio of Compound 1 to besylate, is characterized by one or more of the following peaks as measured in degrees in an X-ray powder diffraction pattern: a peak from about 5.0 to about 5.4 (e.g., about 5.2), a peak from about 10.5 to about 10.9 (e.g., about 10.7), a peak from about 11.0 to about 11.4 (e.g., about 11.2), a peak from about 12.2 to about 12.6 (e.g., about 12.4), a peak from about 14.7 to about 15.1 (e.g., about 14.9), a peak from about 15.0 to about 15.4 (e.g., about 15.2), a peak from about 15.9 to about 16.3 (e.g., about 16.1), a peak from about 17.8 to about 18.2 (e.g., about 18.0), a peak from about 18.4 to about 18.8 (e.g., about 18.6), a peak from about 20.7 to about 21.1 (e.g., about 20.9), a peak from about 23.1 to about 23.5 (e.g., about 23.3), and a peak from about 24.5 to about 24.9 (e.g., about 24.7). In some embodiments, the crystalline Compound 1.besylate is characterized by at least the following peaks: 5.2, 11.2, 12.4, 14.9, 18.6 and 24.7.

In some embodiments the crystalline Compound 1.besylate, has an X-ray powder diffraction pattern substantially similar to the X-ray powder diffraction pattern provided in FIG. 48.

In some embodiments, the crystalline Compound 1.besylate, having a 2 to 1 ratio of Compound 1 to besylate, has a monoclinic crystal system. In some embodiments, the crystalline Compound 1.besylate, having a 1 to 1 ratio of Compound 1 to besylate, has a $P2_1/c$ space group.

In some embodiments, the crystalline Compound 1.besylate, in which the ratio of Compound 1 to besylate is 2 to 1, has the following unit cell dimensions as measured in Å at 120K
a=about 17.4 to about 17.8 (e.g., about 17.6)
b=about 17.5 to about 17.9 (e.g., about 17.7)
c=about 18.7 to about 19.1 (e.g., about 18.9).

In one aspect, the invention features Compound 1.besylate.$H_2O$, for example, crystalline Compound 1.besylate.$H_2O$. In some embodiments, the crystalline Compound 1.besylate.$H_2O$ has a ratio of Compound 1:besylate: water of 1:2:1.

In some embodiments, the crystalline Compound 1.besylate.$H_2O$, having a 1 to 2 to 1 ratio of Compound 1 to besylate to water, is characterized by one or more of the following peaks as measured in degrees in an X-ray powder diffraction pattern: a peak from about 4.9 to about 5.3 (e.g., about 5.1), a peak from about 8.5 to about 8.9 (e.g., about 8.7), a peak from about 12.9 to about 13.3 (e.g., about 13.1), a peak from about 17.6 to about 18.0 (e.g., about 17.8), a peak from about 18.0 to about 18.4 (e.g., about 18.2), a peak from about 20.1 to about 20.5 (e.g., about 20.3), a peak from about 20.9 to about 21.3 (e.g., about 21.1), a peak from about 22.2 to about 22.6 (e.g., about 22.4), a peak from about 24.0 to about 24.4 (e.g., about 24.2), and a peak from about 25.9 to about 26.3 (e.g., about 26.1). In some embodiments, the crystalline Compound 1.besylate is characterized by at least the following peaks: 5.1, 13.1, 17.8, 18.2, 20.3, and 25.4.

In some embodiments the crystalline Compound 1.besylate.$H_2O$ has an X-ray powder diffraction pattern substantially similar to the X-ray powder diffraction pattern provided in FIG. 49.

In some embodiments, the crystalline Compound 1.besylate.$H_2O$ has a triclinic crystal system. In some embodiments, the crystalline Compound 1.besylate.$H_2O$ has a P-1 bar space group.

In some embodiments, the crystalline Compound 1.besylate.$H_2O$ has the following unit cell dimensions as measured in Å at 120K
a=about 10.1 to about 10.5 (e.g., about 10.3)
b=about 10.4 to about 10.8 (e.g., about 10.6)
c=about 17.4 to about 17.8 (e.g., about 17.6).

In one aspect, the invention features a method of making crystalline Compound 1.besylate. The method comprises mixing Compound 1, benzenesulfonic acid (preferably 0.95 equivalents anhydrous), and an aprotic aromatic solvent such as toluene to provide a slurry. The slurry is heated (preferably 75-95° C.) and then cooled and filtered to provide crystalline Compound 1.besylate. In some embodiments, the benzenesulfonic acid is used as a hydrate. In some embodiments, the amount of benzenesulfonic acid use is 0.6-1.3 equivalents. In some embodiments, the temperature is 20-110° C. In some embodiments the solvent is an aprotic ether such as dimethoxy methane, t-butyl methyl ether, and anisole. In some embodiments, the solvent is an aprotic ester such as ethyl acetate, isopropyl acetate, n-butyl acetate, n-propyl acetate, t-butyl acetate or mixtures thereof (such as ethyl acetate and isopropyl acetate). In some embodiments, the solvent is a nitrile such as acetonitrile. In some embodiments, the solvent is a mixture of aprotic ether and aprotic ester such as mixtures of tetrahydrofuran with acetate solvents (such as isopropyl acetate) or 2-methyltetrahydrofuran with acetate solvents (such as isopropyl acetate). In some embodiments, the aromatic solvent is a carbocyclic aromatic solvent such as toluene, benzene, and xylene. In some embodiments, the aromatic carbocyclic aromatic solvent is anhydrous such as anhydrous toluene, anhydrous benzene, or anhydrous xylene. In some embodiments the drying of crystalline Compound 1.besylate is performed using fluidized bed or under humidified conditions between 60% RH and 98% RH. For instance, in some embodiments, Compound 1.besylate is dried in commercially available drying equipment, such as an environmental chamber ES2000 REACH-IN upright model available from Environmental Specialties located in North Carolina, substituting humidified drying air for anhydrous drying air to provide a relative humidity between about 60% and 98% at a temperatures between about 25° C. and about 40° C.

In one aspect, the invention features a method of making crystalline N-[2,4-bis(1,1-dimethylethyl)-5-hydroxyphenyl]-1,4-dihydro-4-oxoquinoline-3-carboxamide.besylate.$H_2O$. The method comprises mixing Compound 1.besylate, benzenesulfonic acid hydrate, and an aprotic acetate solvent such as the mixture of ethyl acetate and isopropyl acetate to provide a slurry. The slurry is stirred then filtered to provide crystalline Compound 1.besylate.$H_2O$.

In one aspect, the invention features a pharmaceutical preparation of Compound 1.besylate, e.g., crystalline Compound 1.besylate. In some embodiments, the pharmaceutical preparation is substantially free of other solid forms of Compound 1. In some embodiments the ratio of Compound 1 to besylate in the preparation is 1:1. In other embodiments, the ratio of Compound 1 to besylate in the preparation is 2:1.

In one aspect, the invention features a pharmaceutical preparation of Compound 1.besylate.$H_2O$, e.g., crystalline Compound 1.besylate.$H_2O$. In some embodiments, the pharmaceutical preparation is substantially free of other solid forms of Compound 1. In some embodiments, the ratio of Compound 1 to besylate to water in the preparation is 1:2:1.

In one aspect, the invention features a method for treating a CFTR mediated disease in a mammal comprising administering a solid form of Compound 1 as described herein. In some embodiments, the disease is selected from cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjogren's disease. In some preferred embodiments, the disease is cystic fibrosis.

In some embodiments, the Compound 1 is a component of a pharmaceutical composition.

In some embodiments, the method includes administering an additional therapeutic agent.

In one aspect, the invention features a pharmaceutical pack or kit comprising a solid form of Compound 1 as described herein and a pharmaceutically acceptable carrier.

The term "besylate", as used herein, unless otherwise indicated, means benzene sulfonate.

The term "treatment", as used herein, unless otherwise indicated, means the treatment or prevention of a CFTR related disorder as provided in the methods described herein, including curing, reducing the symptoms of or slowing the progress of said disorder. The terms "treat" and "treating" are defined in accord the foregoing term "treatment".

The term "substantially free" when referring to a designated crystalline form of Compound 1 means that there is less than 20% (by weight) of the designated form(s) (e.g., a crystalline or amorphous form of Compound 1) present, more preferably, there is less than 10% (by weight) of the designated form(s) present, more preferably, there is less than 5% (by weight) of the designated form(s) present, and most preferably, there is less than 1% (by weight) of the designated crystalline form(s) present.

The term "substantially pure" when referring to a designated crystalline form of Compound 1 means that the designated crystalline form contains less than 20% (by weight) of residual components such as alternate polymorphic or isomorphic crystalline form(s) of Compound 1. It is preferred that a substantially pure form of Compound 1 contain less than 10% (by weight) of alternate polymorphic or isomorphic crystalline forms of Compound 1, more preferred is less than 5% (by weight) of alternate polymorphic or isomorphic crystalline forms of Compound 1, and most preferably less than 1% (by weight) of alternate polymorphic or isomorphic crystalline forms of Compound 1.

The details of one or more embodiments of the invention are set forth in the accompanying figures and the description below. Other features, objects, and advantages of the invention will be apparent from the description and figures, and from the claims.

DETAILED DESCRIPTION

Figure 1:
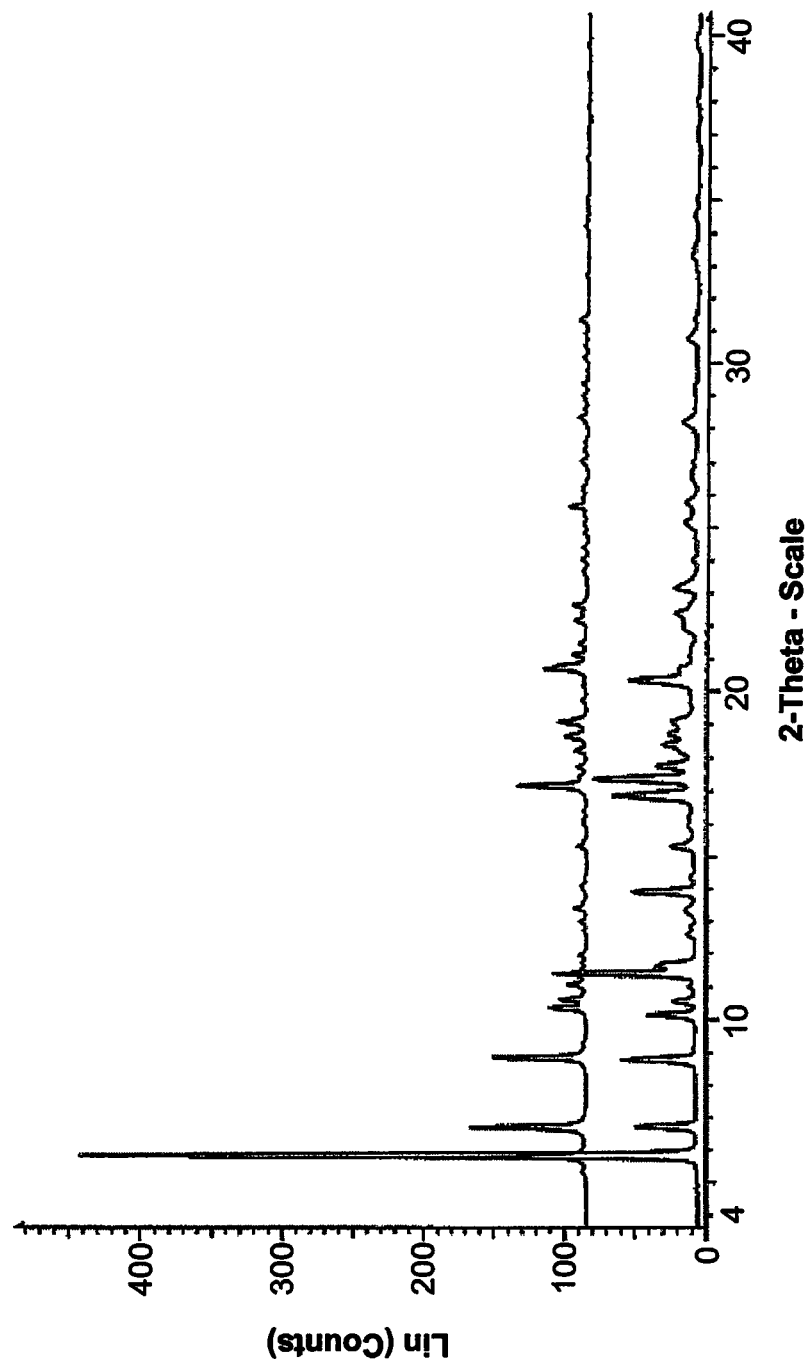
FIG. 1 is an experimental x-ray powder diffraction (XRPD) of Compound 1.2-methylbutyric acid. The upper trace is simulated from low temperature single crystal structure. The lower trace is an experimental pattern obtained at room temperature.
Figure 2:
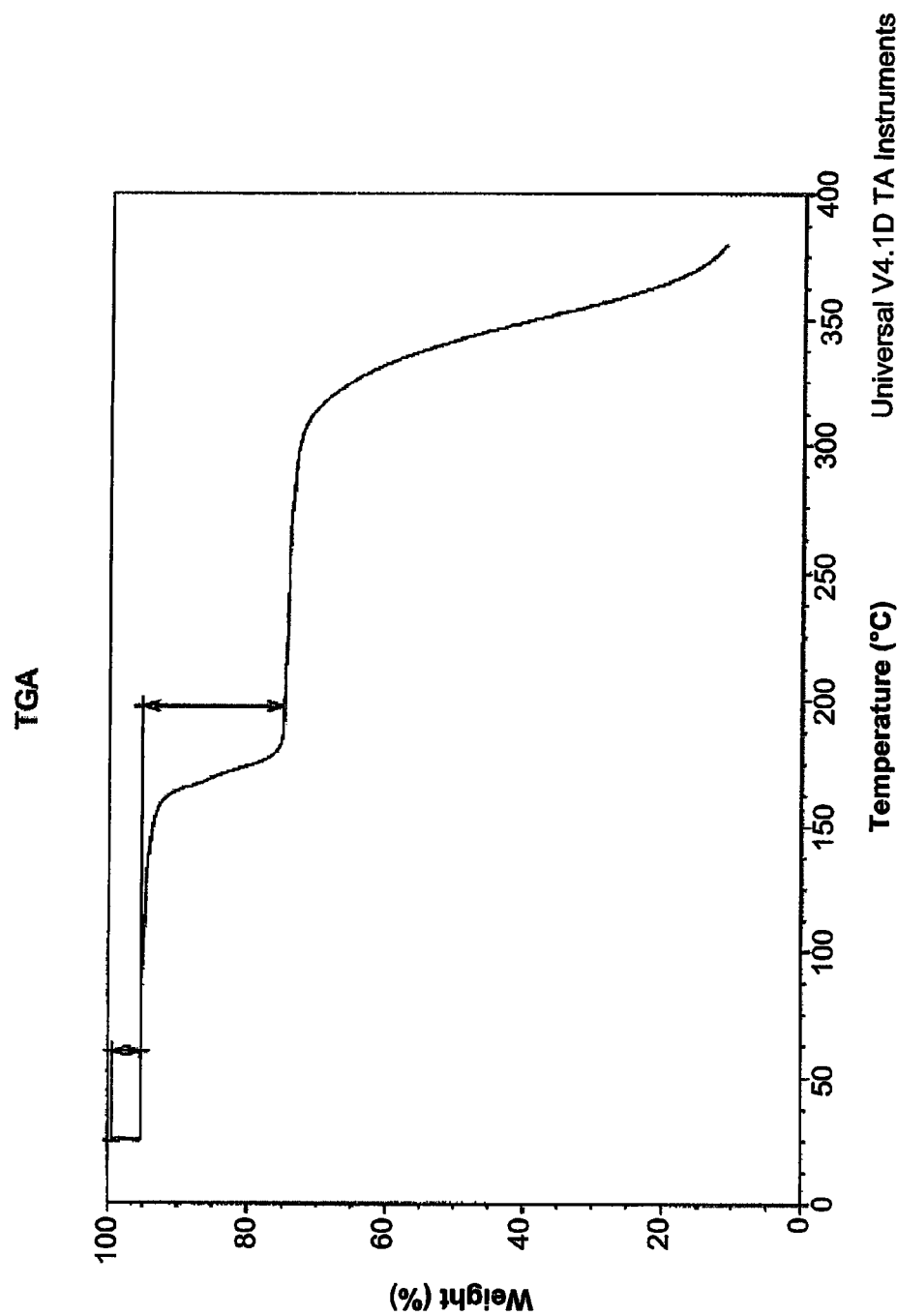
FIG. 2 is a TGA trace of Compound 1.2-methylbutyric acid.
Figure 3:
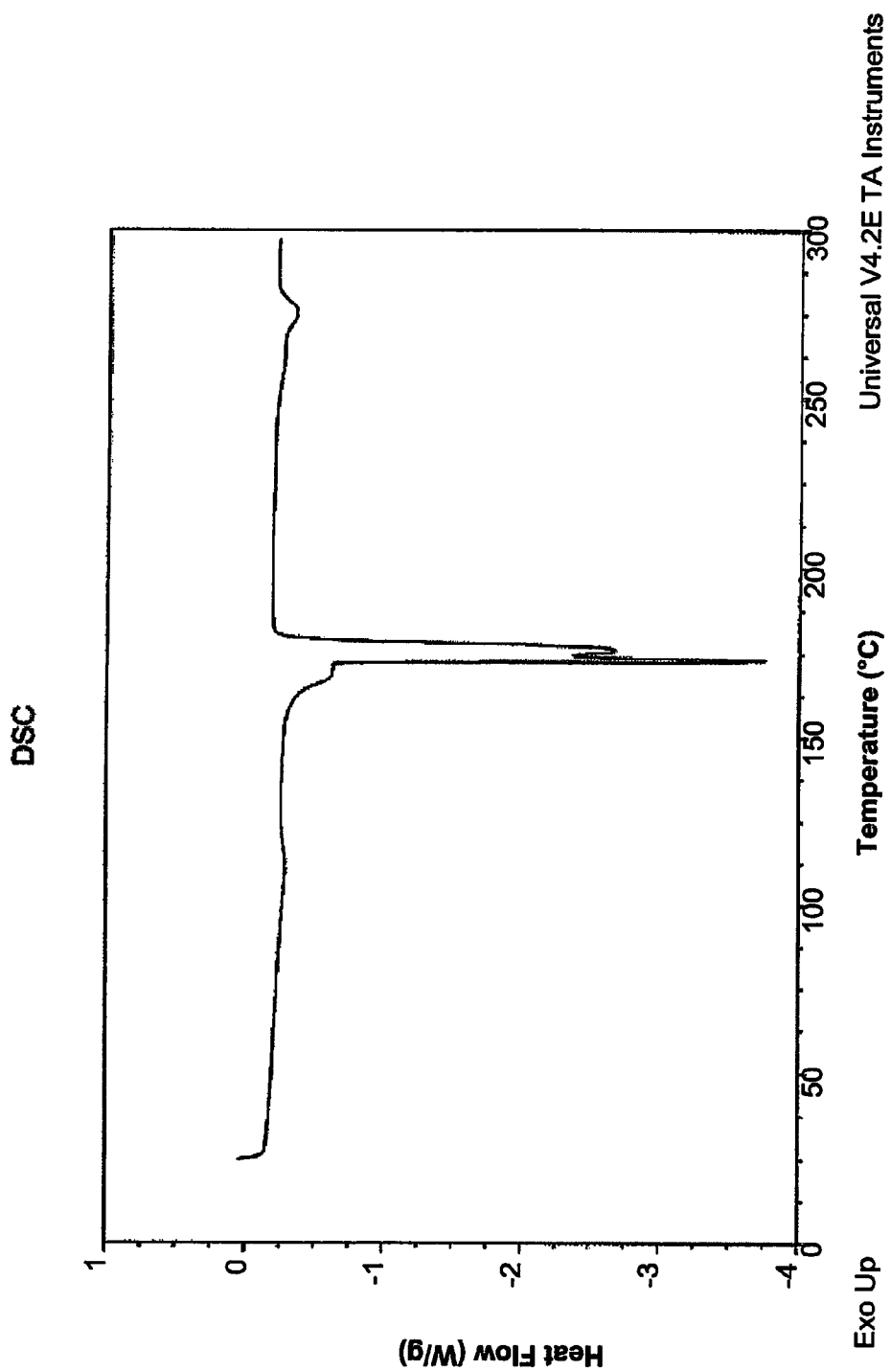
FIG. 3 is a DSC trace of Compound 1.2-methylbutyric acid.
Figure 4:
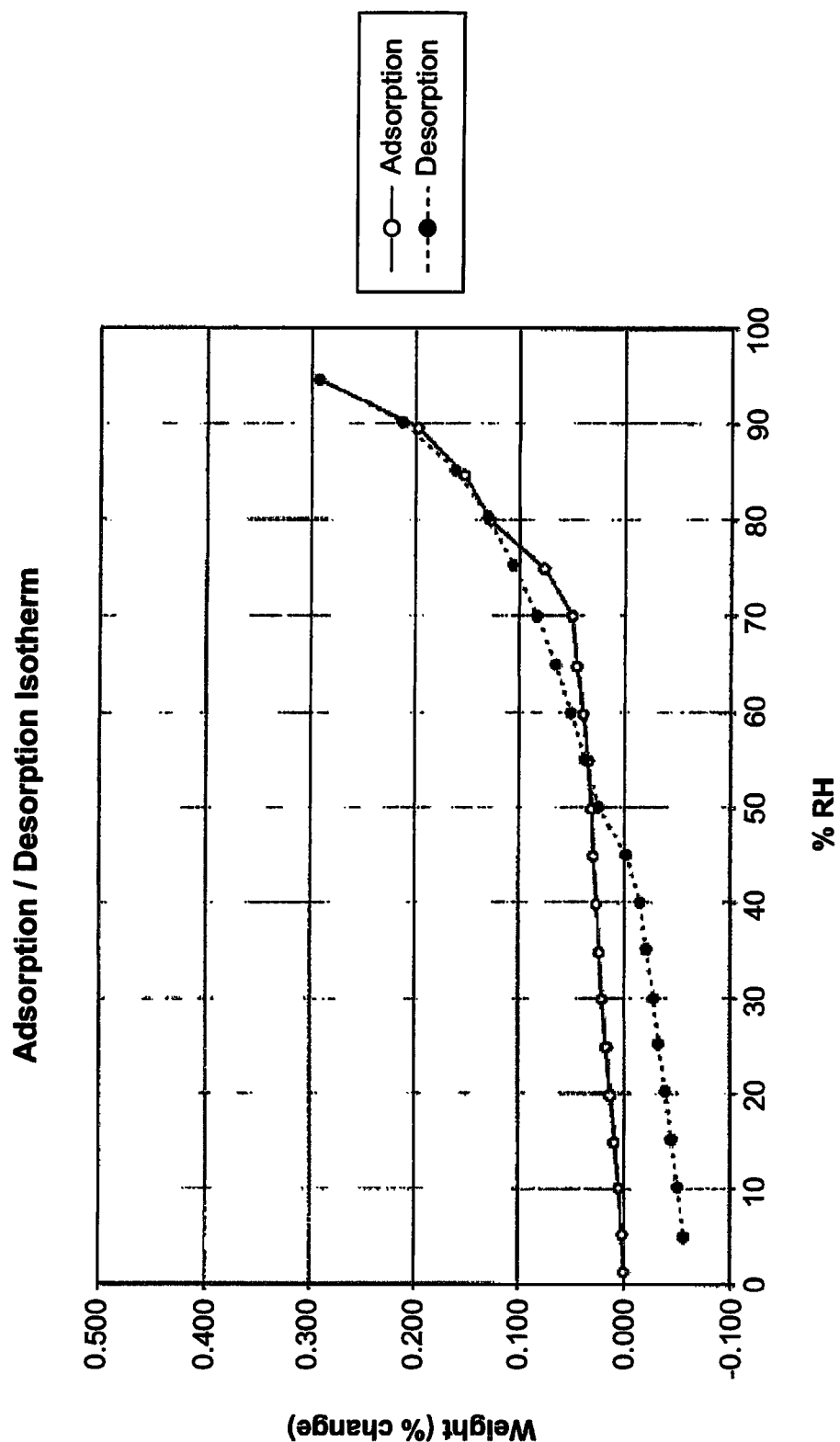
FIG. 4 is a DVS of Compound 1.2-methylbutyric acid.
Figure 5:
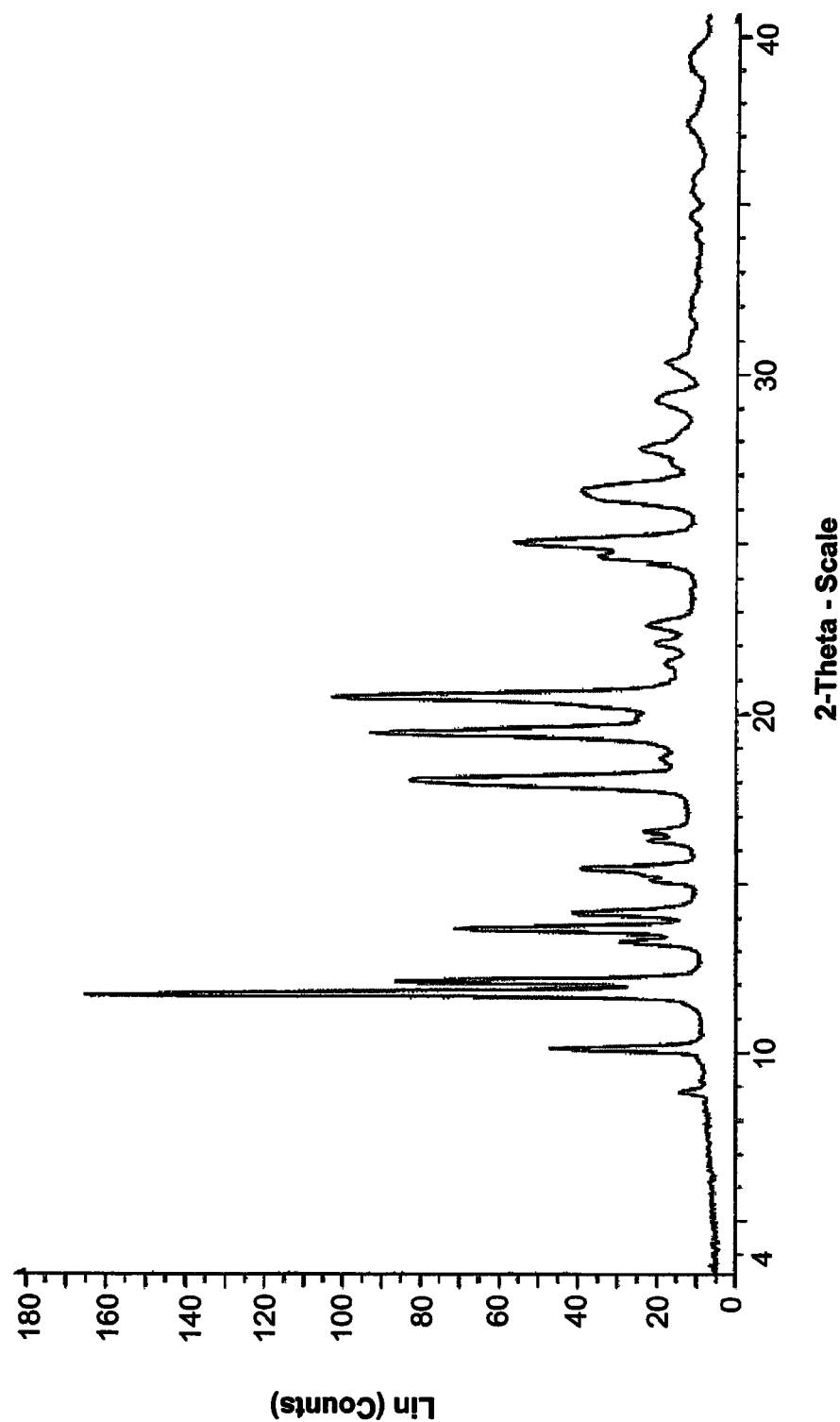
FIG. 5 is an experimental XRPD of Compound 1.propylene glycol.
Figure 6:
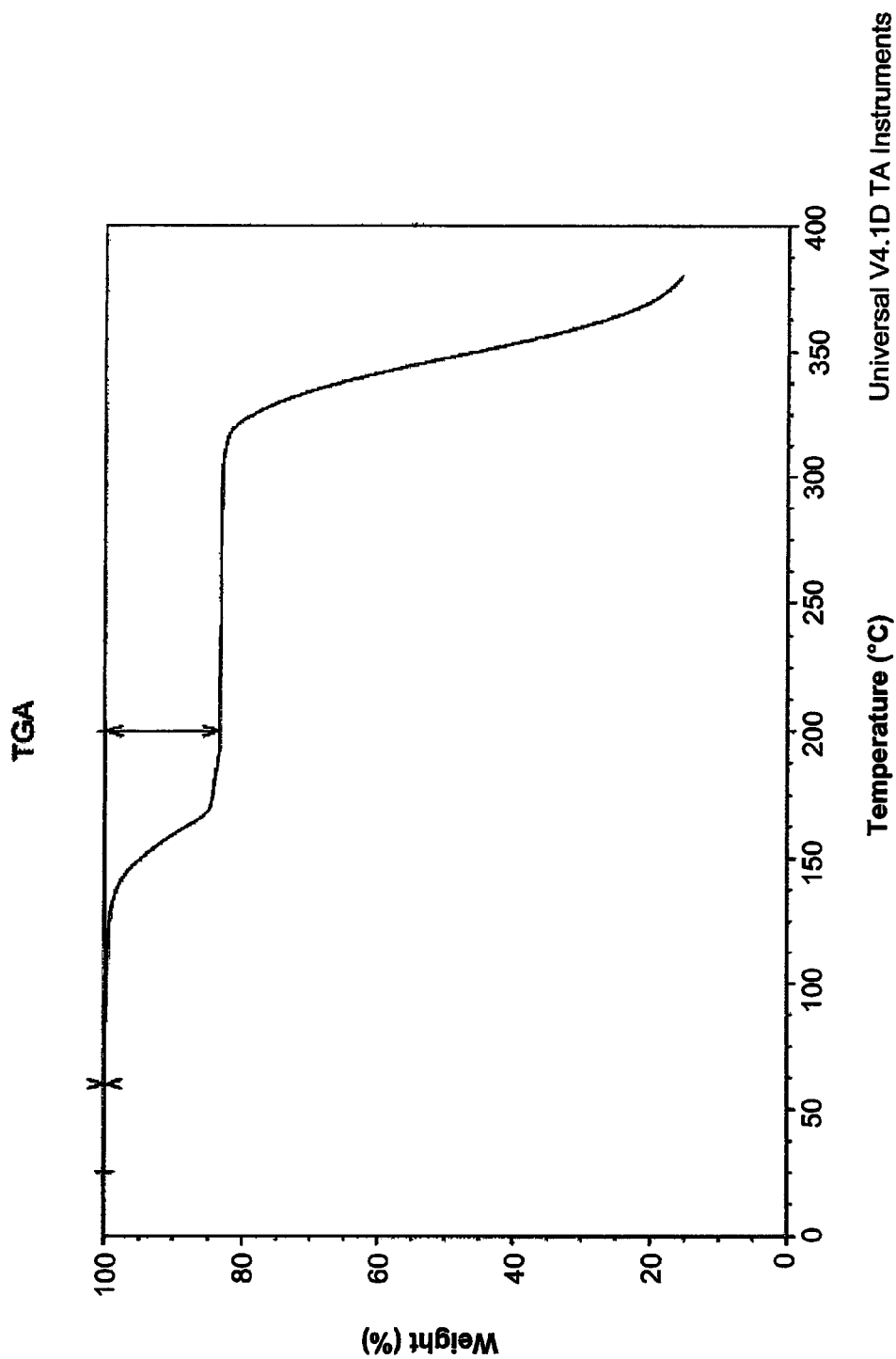
FIG. 6 is a TGA trace of Compound 1.propylene glycol.
Figure 7:
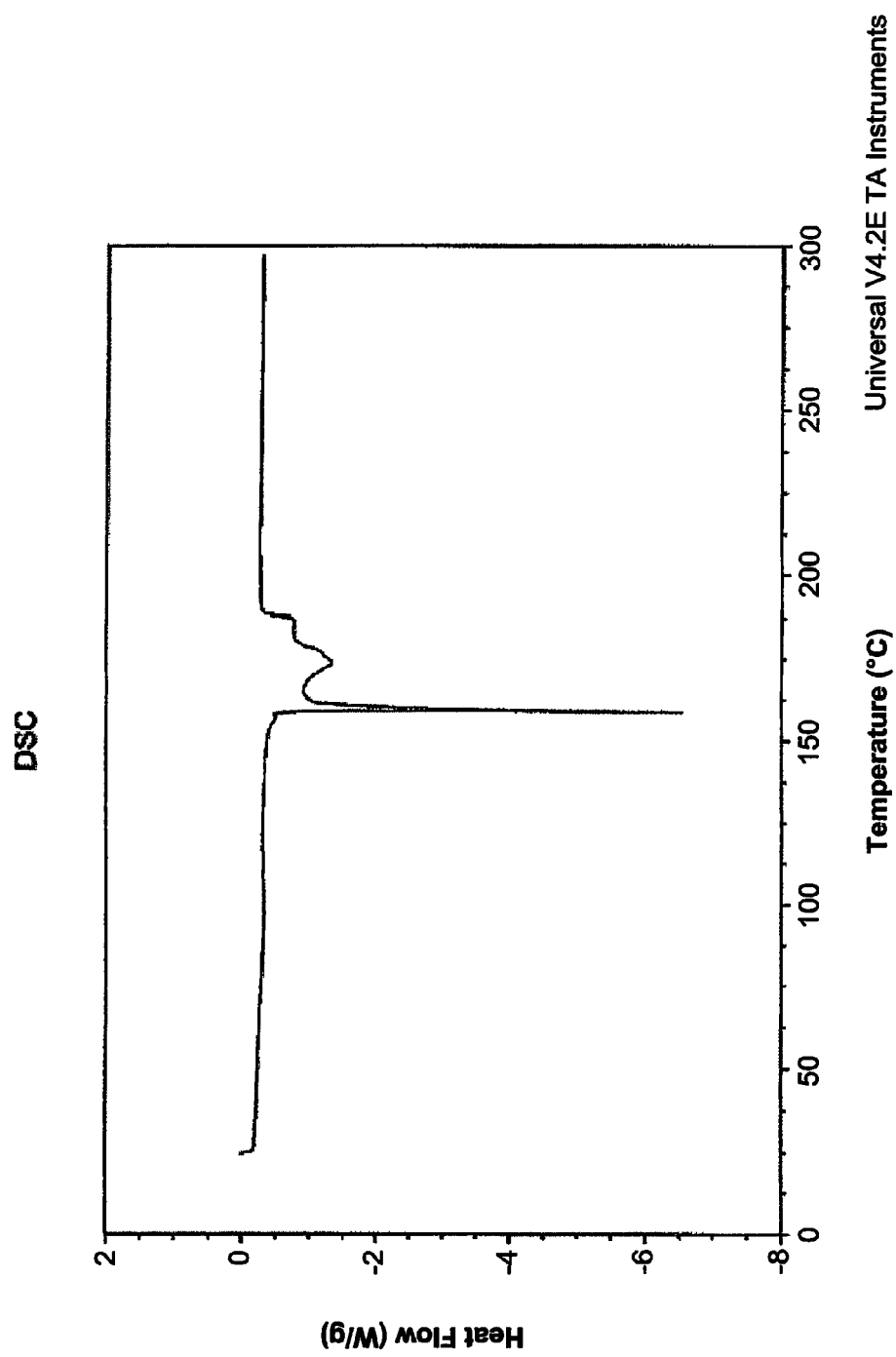
FIG. 7 is a DSC trace of Compound 1.propylene glycol.
Figure 8:
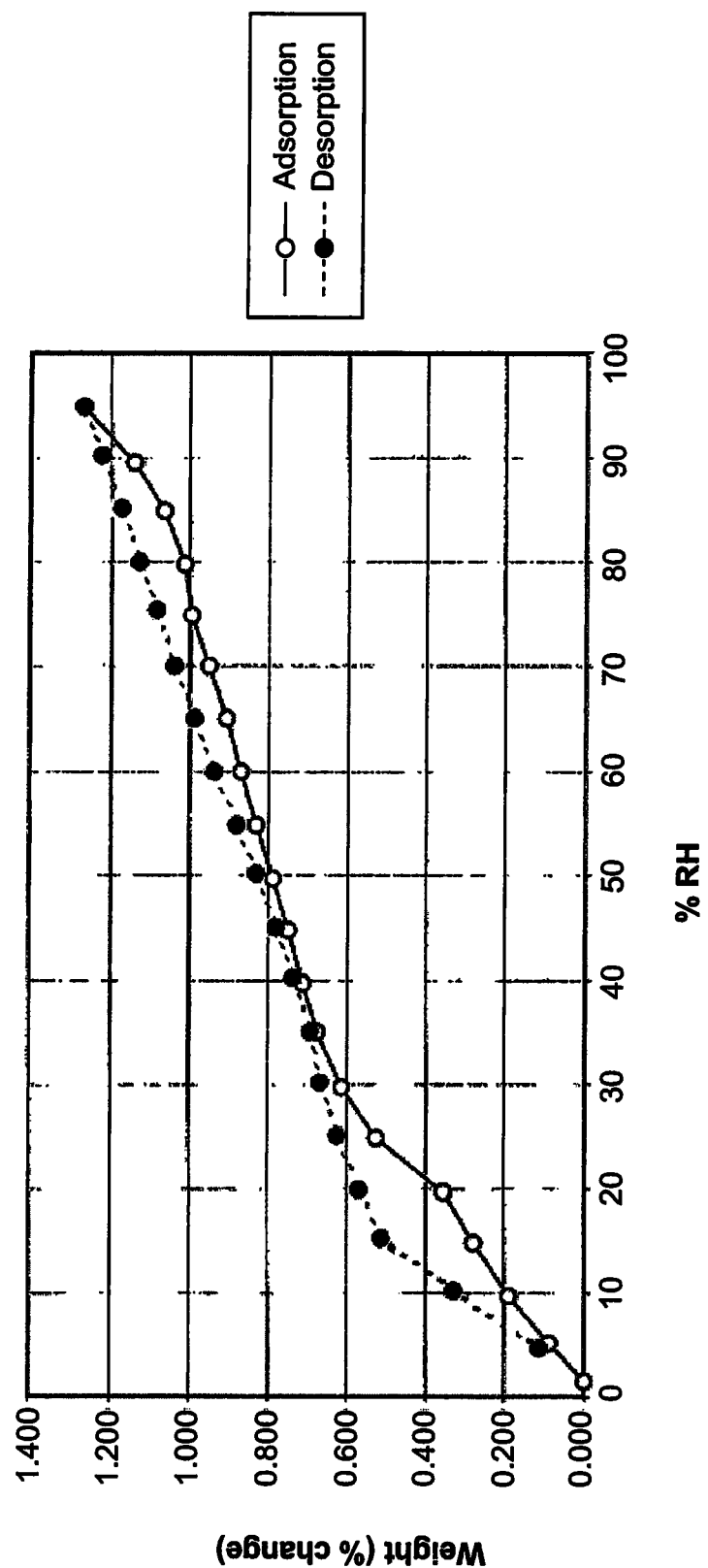
FIG. 8 is a DVS of Compound 1.propylene glycol.
Figure 9:
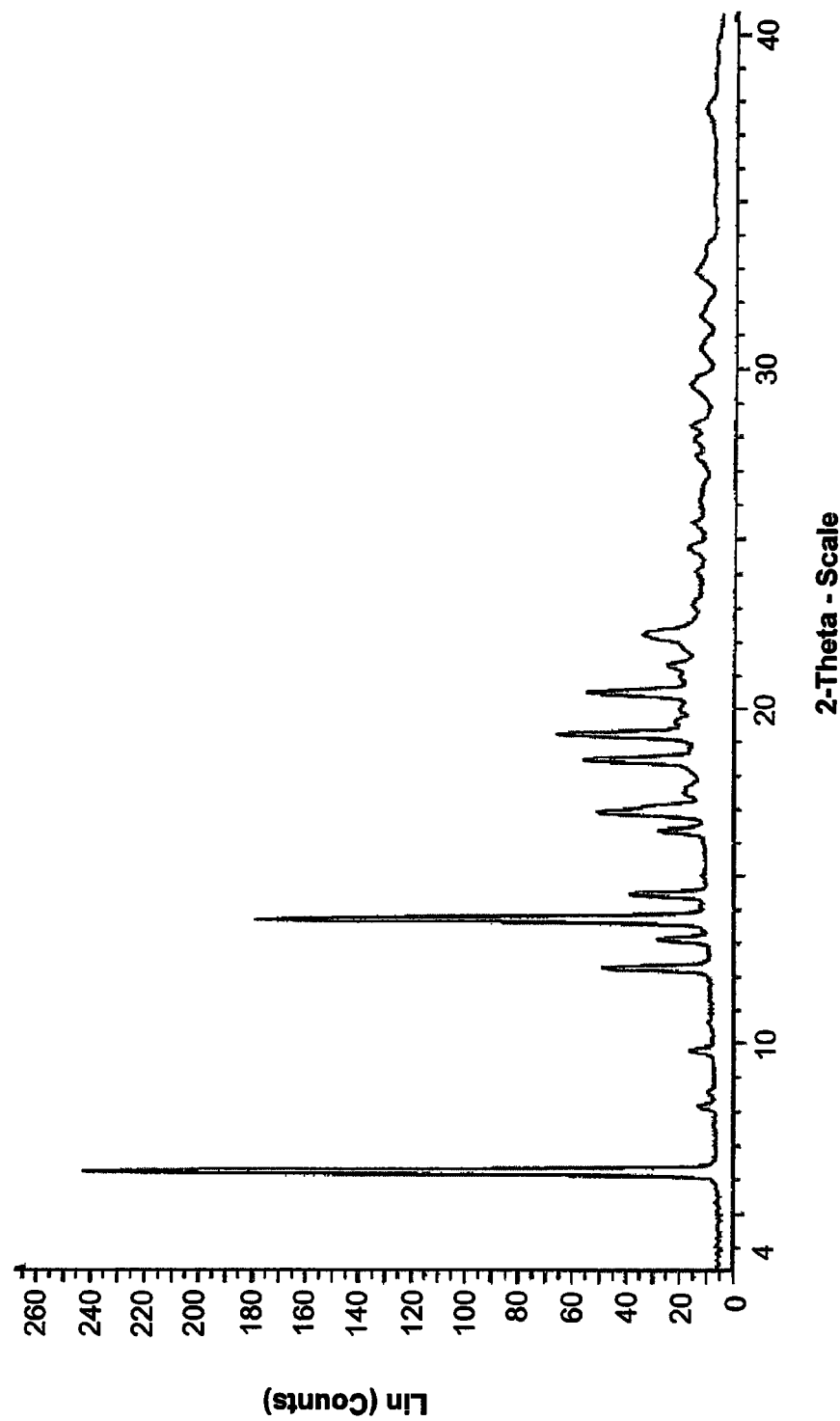
FIG. 9 is an experimental XRPD of Compound 1.PEG KOAc.
Figure 10:
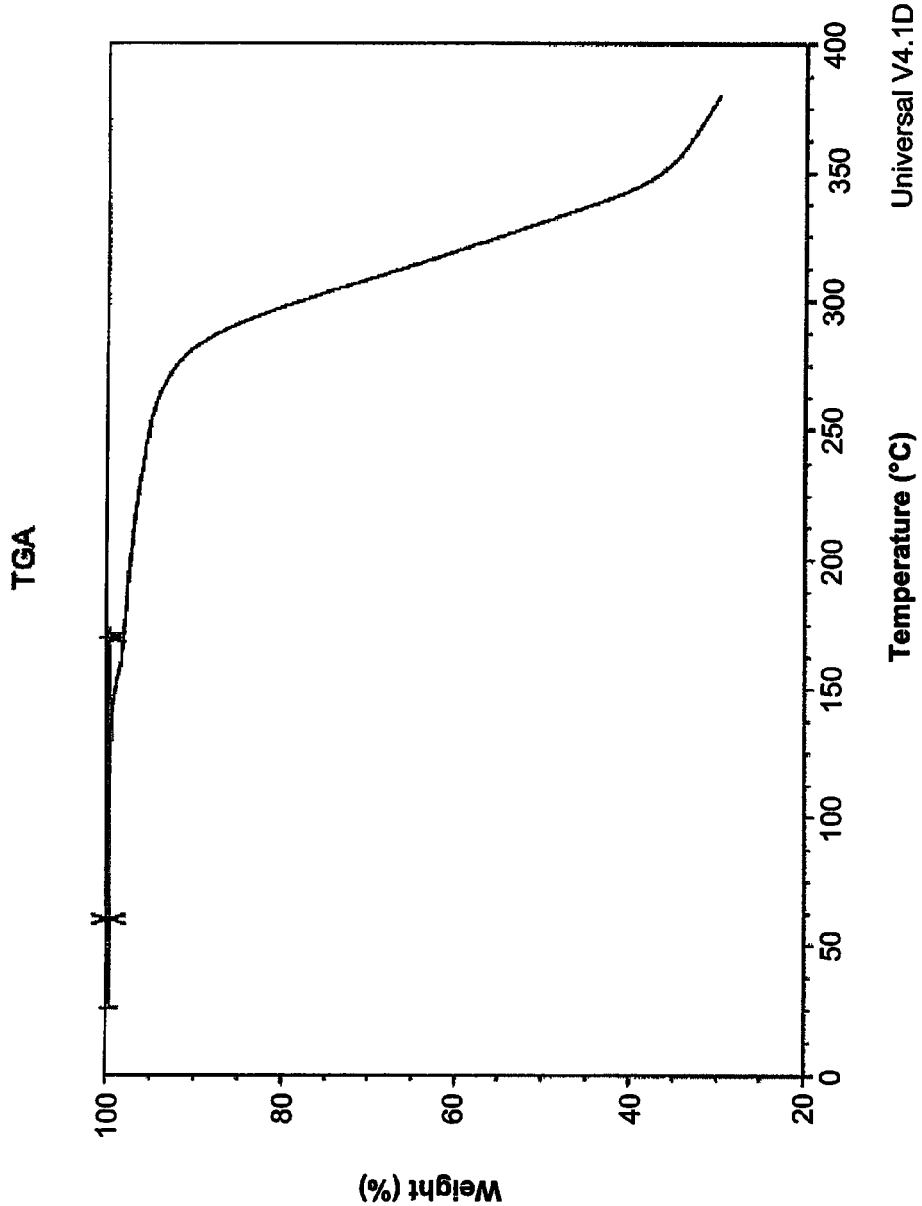
FIG. 10 is a TGA trace of Compound 1.PEG KOAc.
Figure 11:
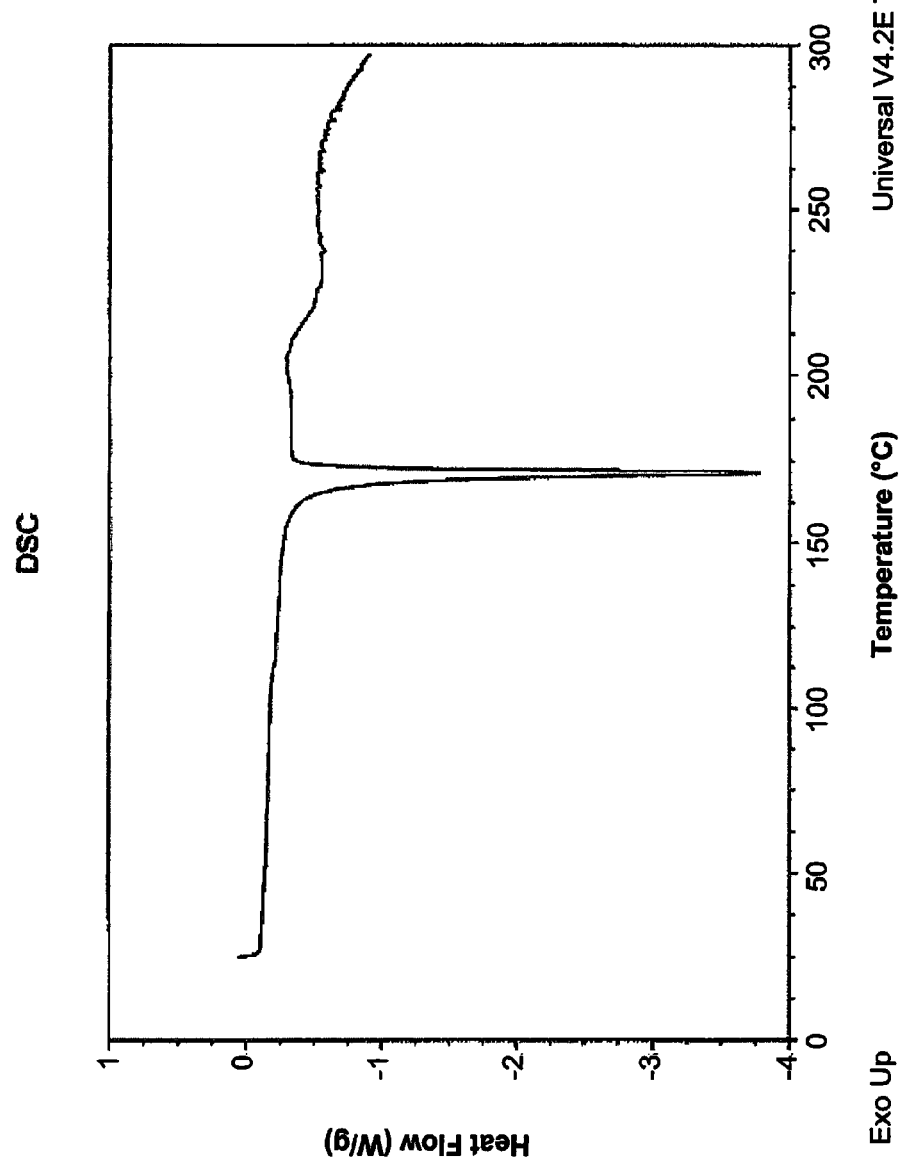
FIG. 11 is a DSC trace of Compound 1.PEG KOAc.
Figure 12:
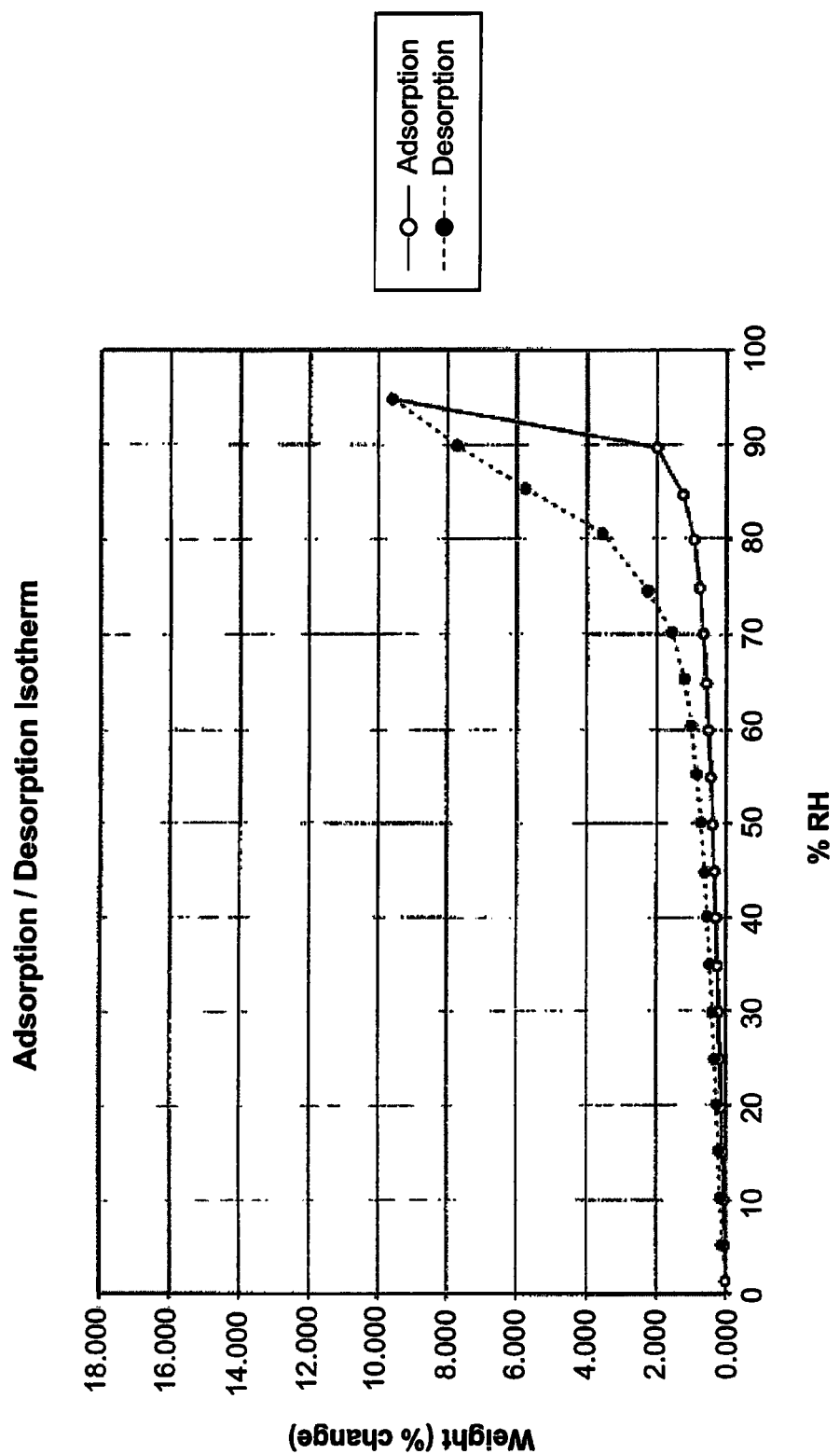
FIG. 12 is a DVS of Compound 1.PEG KOAc.
Figure 13:
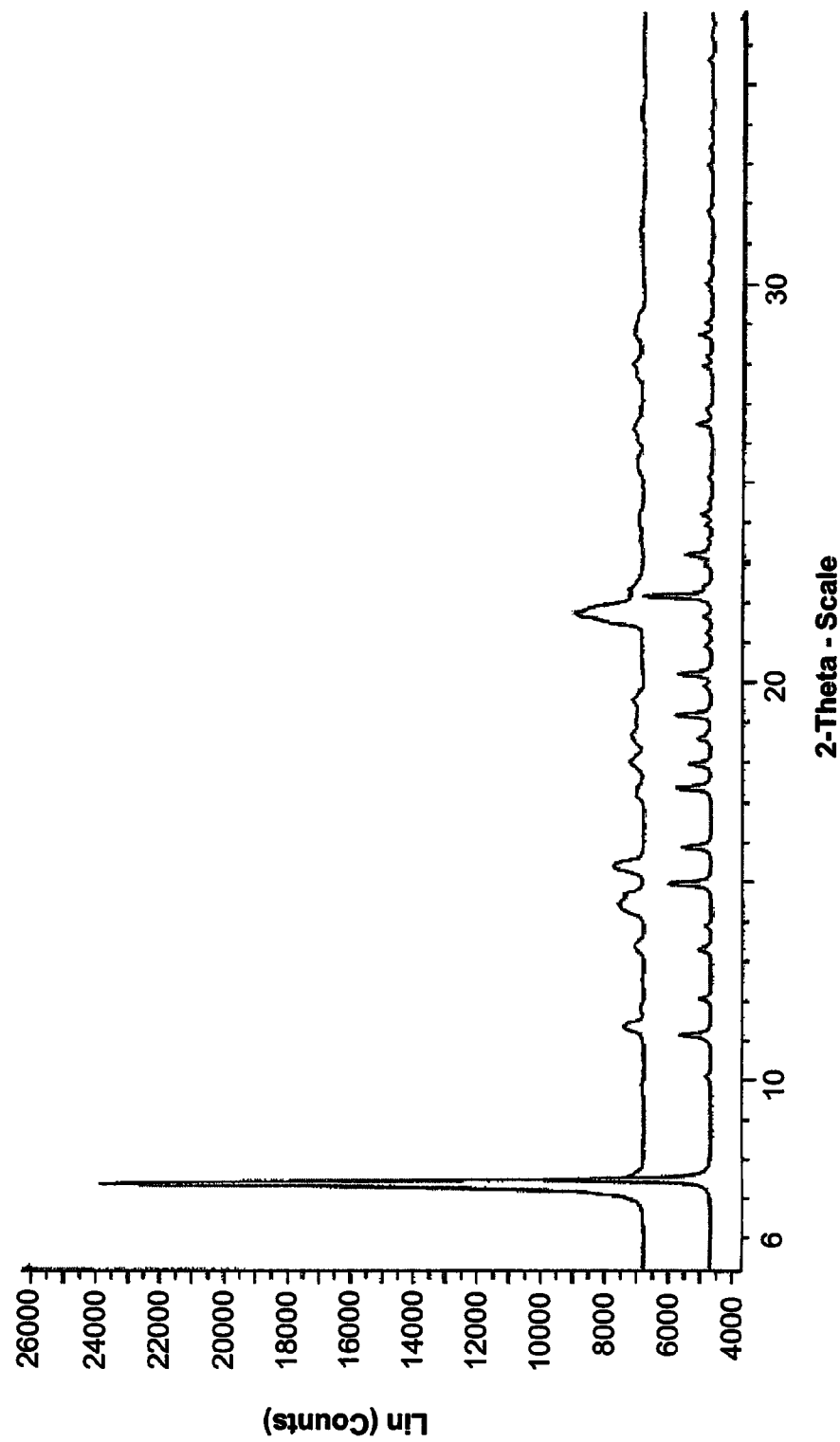
FIG. 13 is an experimental XRPD of Compound 1.lactic acid. The lower trace is simulated from low temperature single crystal structure. The upper trace is an experimental pattern obtained at room temperature.
Figure 14:
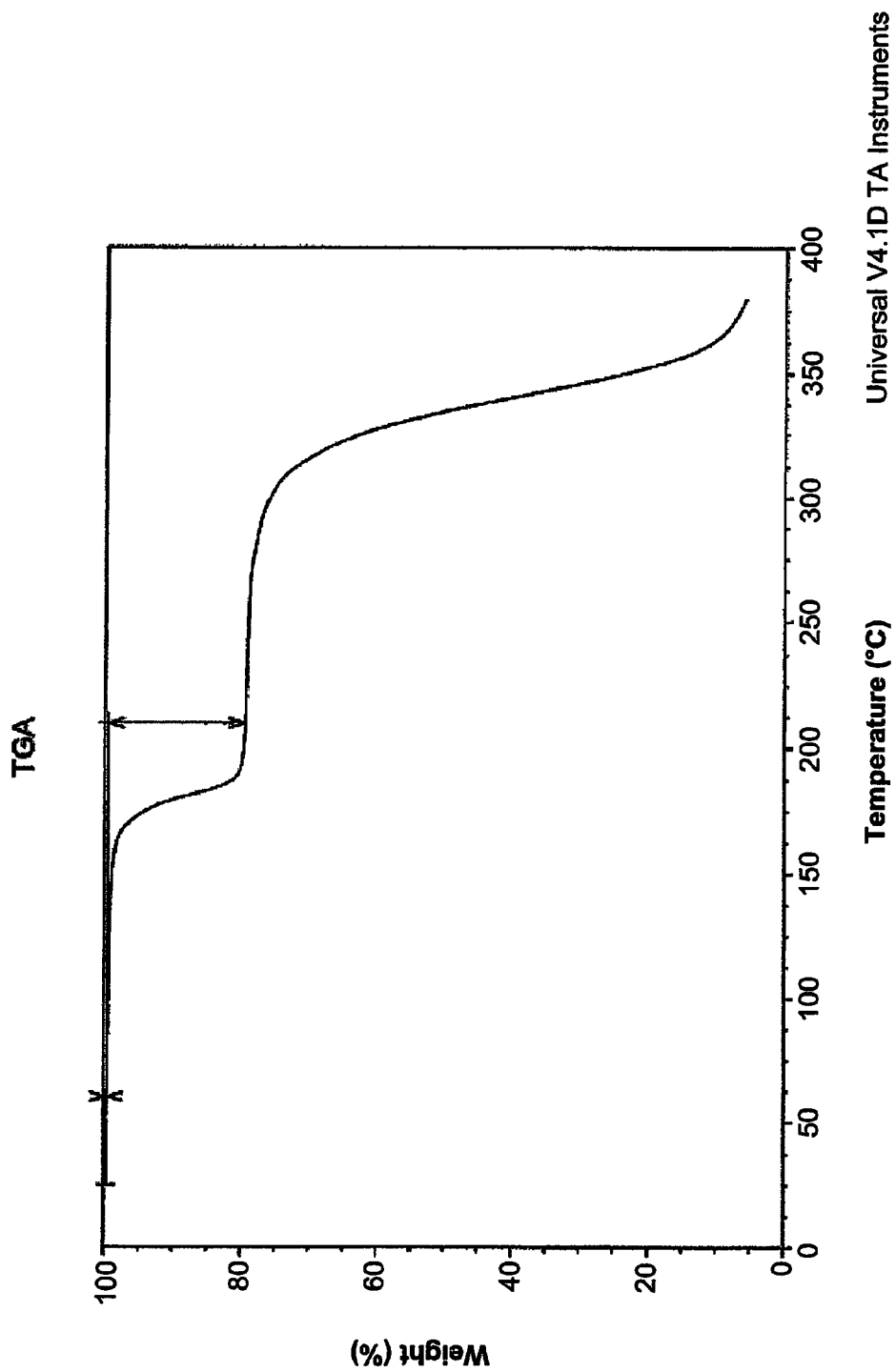
FIG. 14 is a TGA trace of Compound 1.lactic acid.
Figure 15:
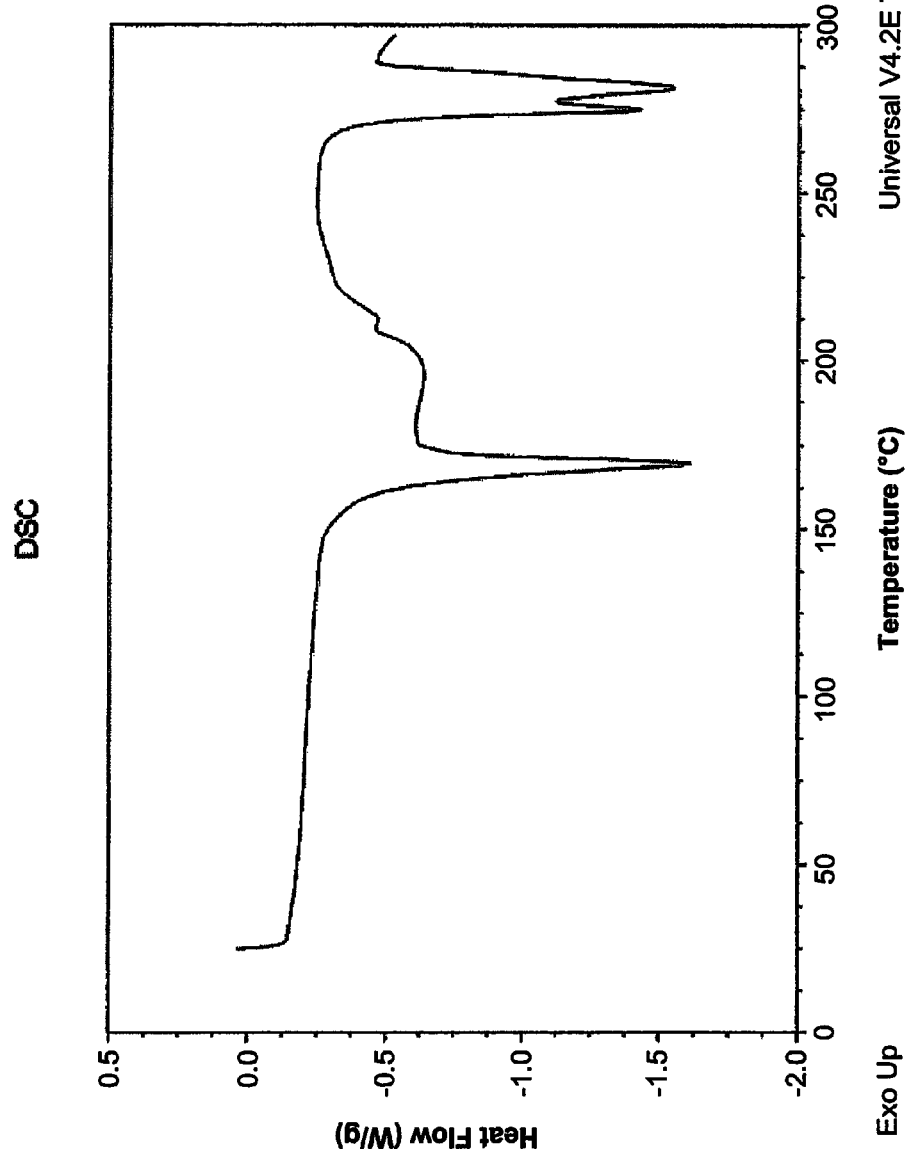
FIG. 15 is a DSC trace of Compound 1.lactic acid.
Figure 16:
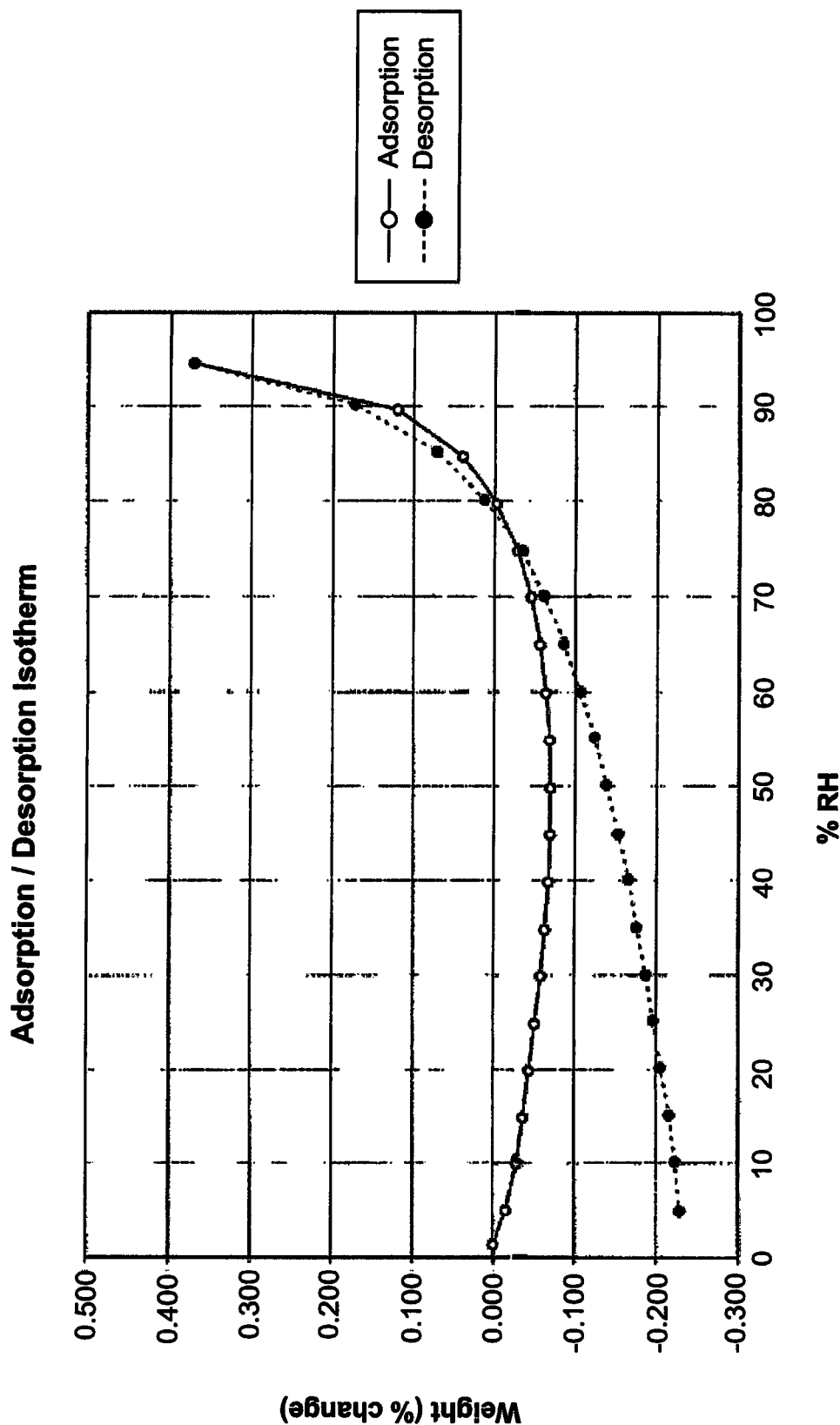
FIG. 16 is a DVS of Compound 1.lactic acid.
Figure 17:
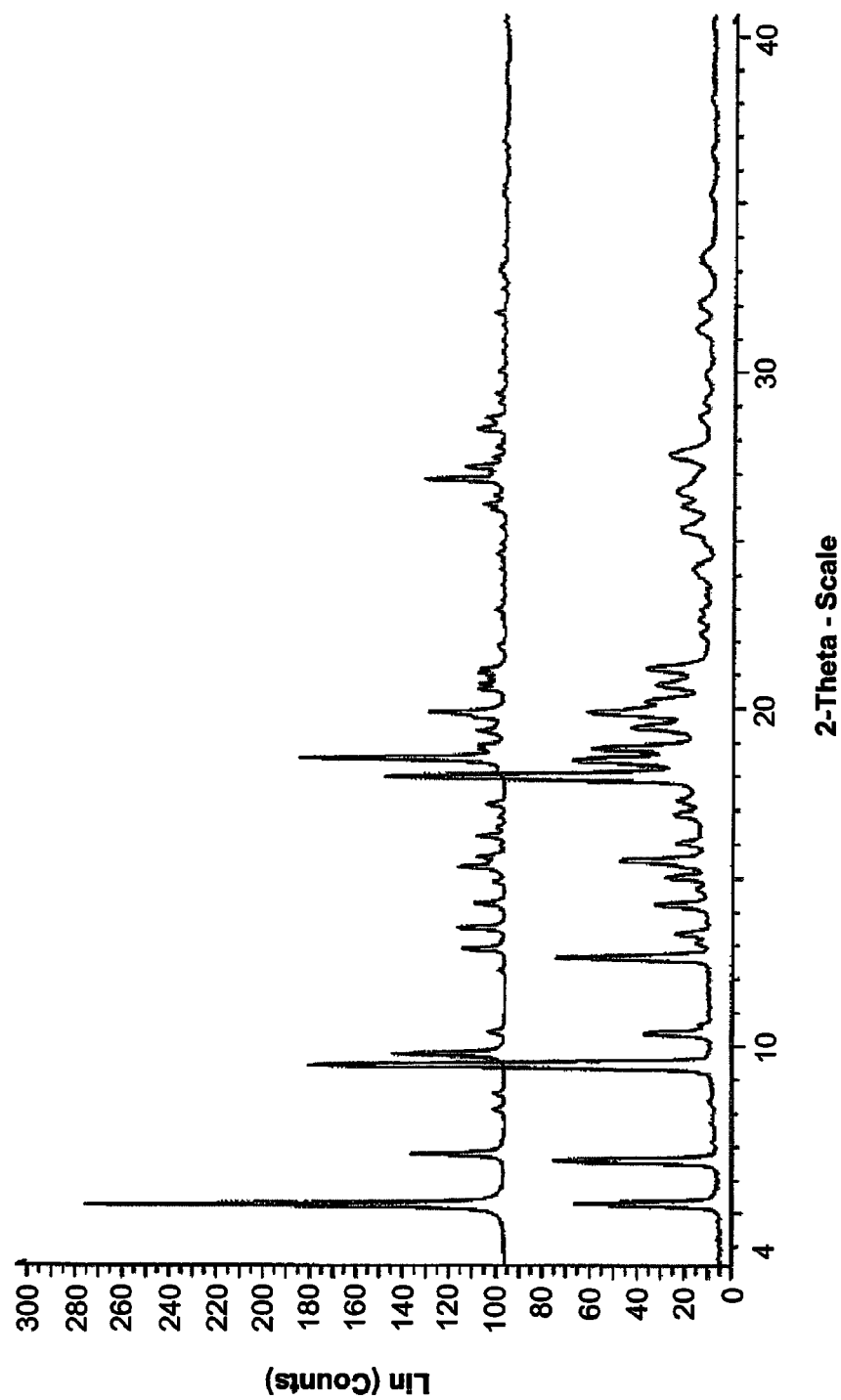
FIG. 17 is an experimental XRPD of Compound 1.isobutyric acid. The upper trace is simulated from low temperature single crystal structure. The lower trace is an experimental pattern obtained at room temperature.
Figure 18:
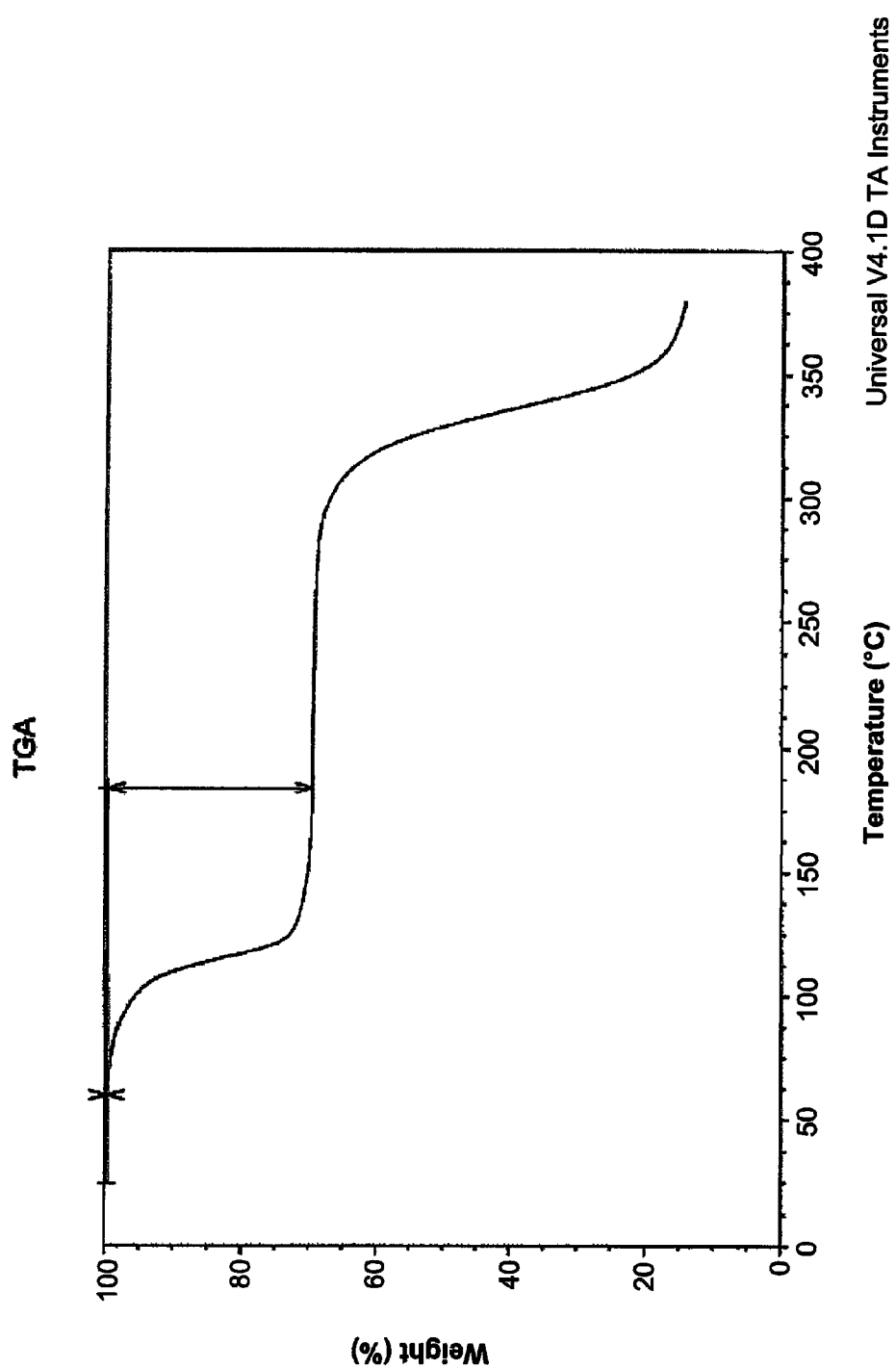
FIG. 18 is a TGA trace of Compound 1.isobutyric acid.
Figure 19:
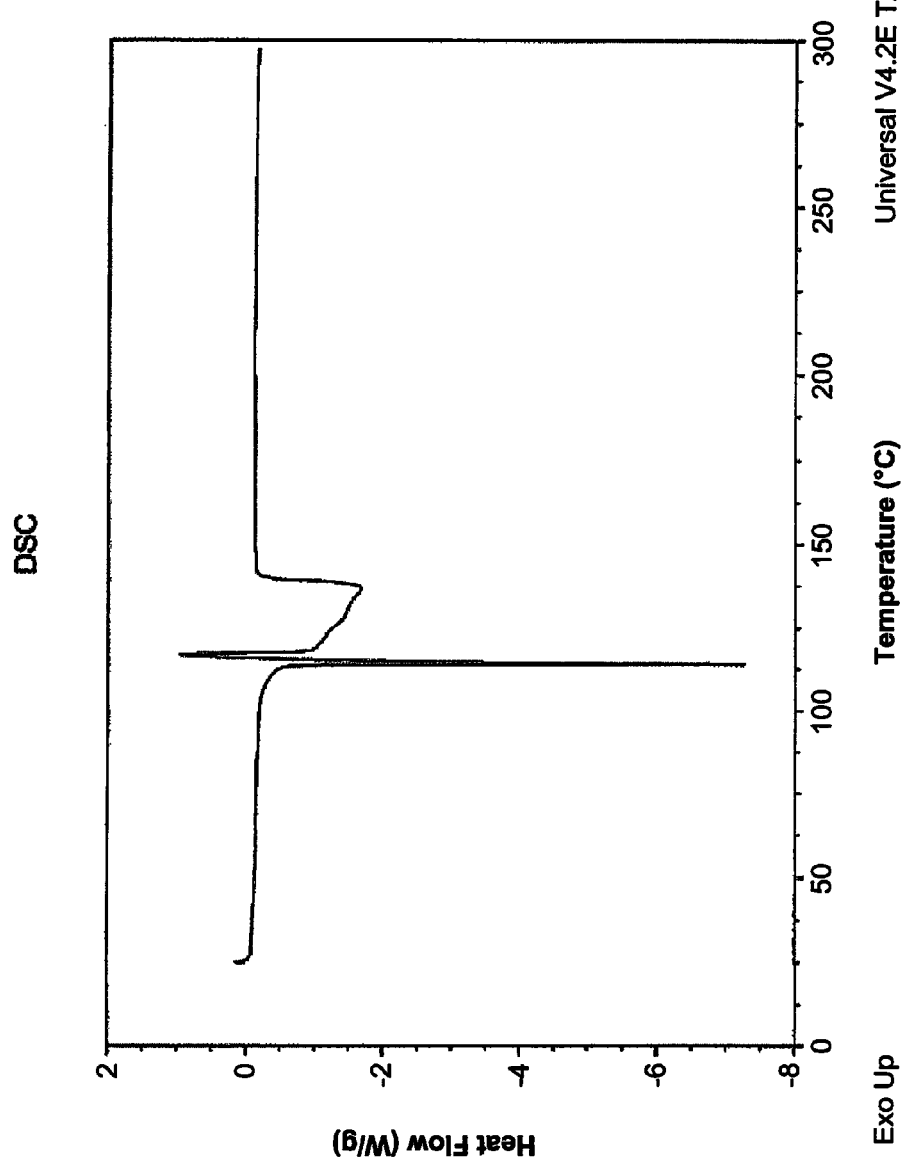
FIG. 19 is a DSC trace of Compound 1.isobutyric acid.
Figure 20:
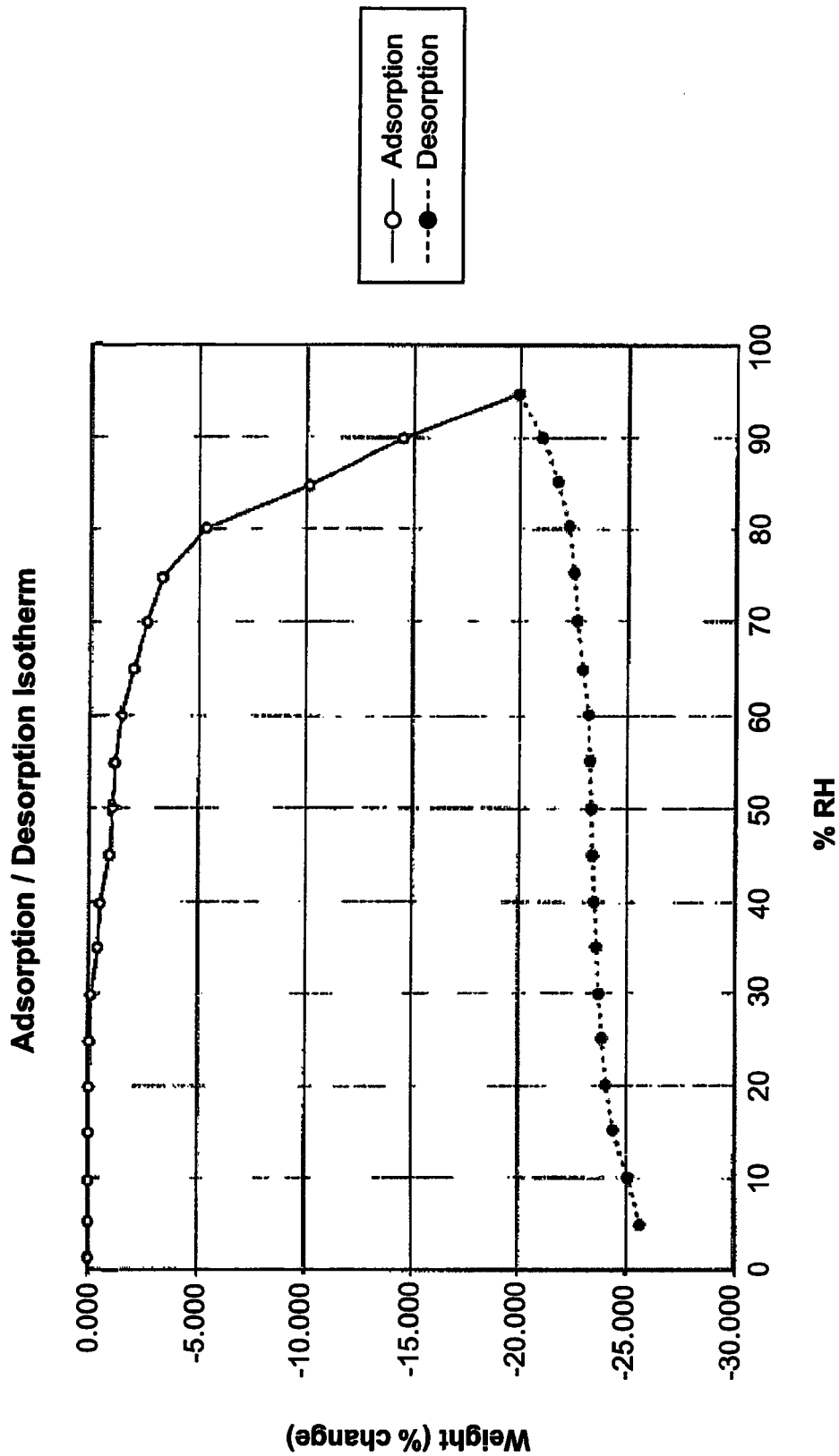
FIG. 20 is a DVS of Compound 1.isobutyric acid.
Figure 21:
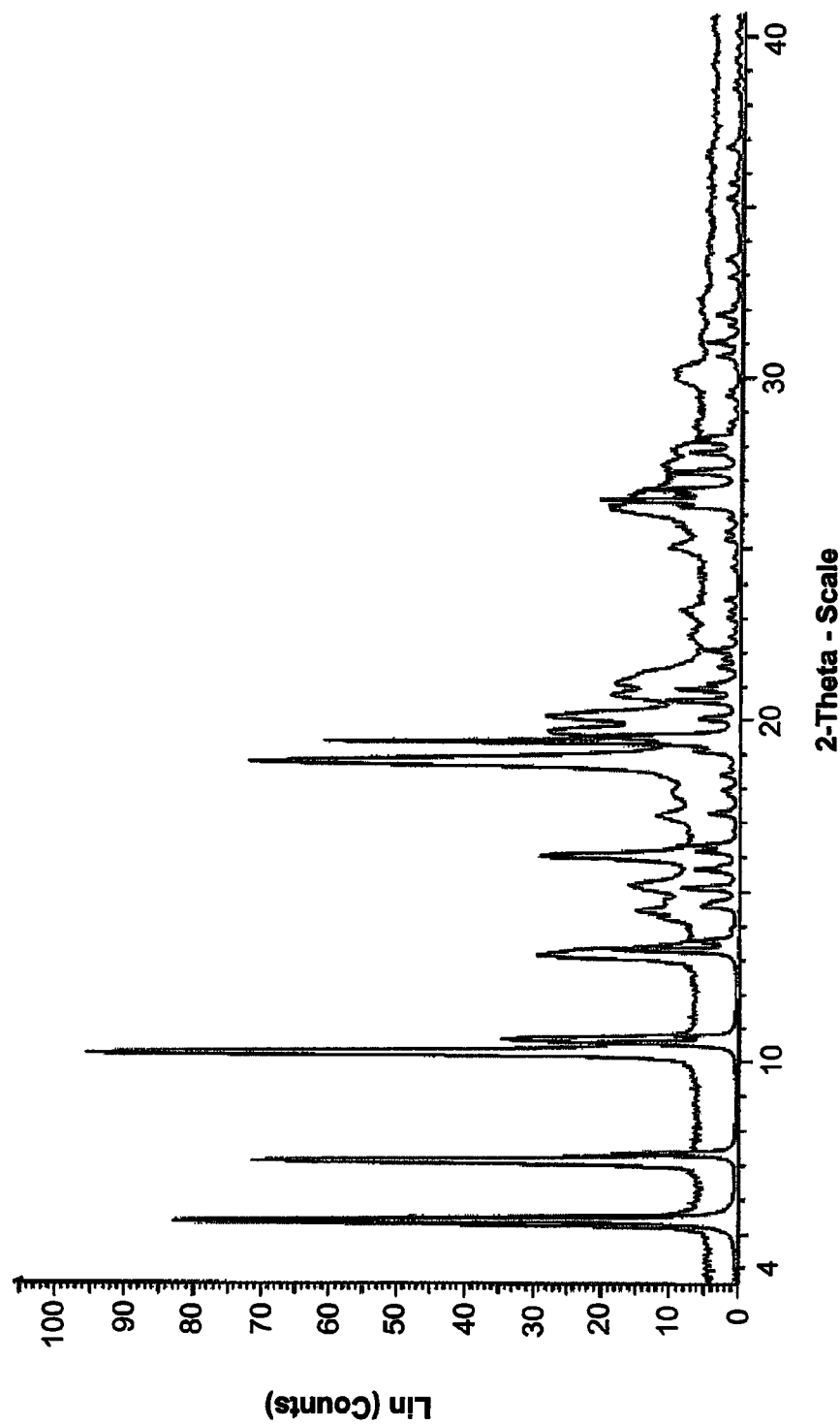
FIG. 21 is an experimental XRPD of Compound 1.propionic acid. The lower trace is simulated from low temperature single crystal structure. The upper trace is an experimental pattern obtained at room temperature.
Figure 22:
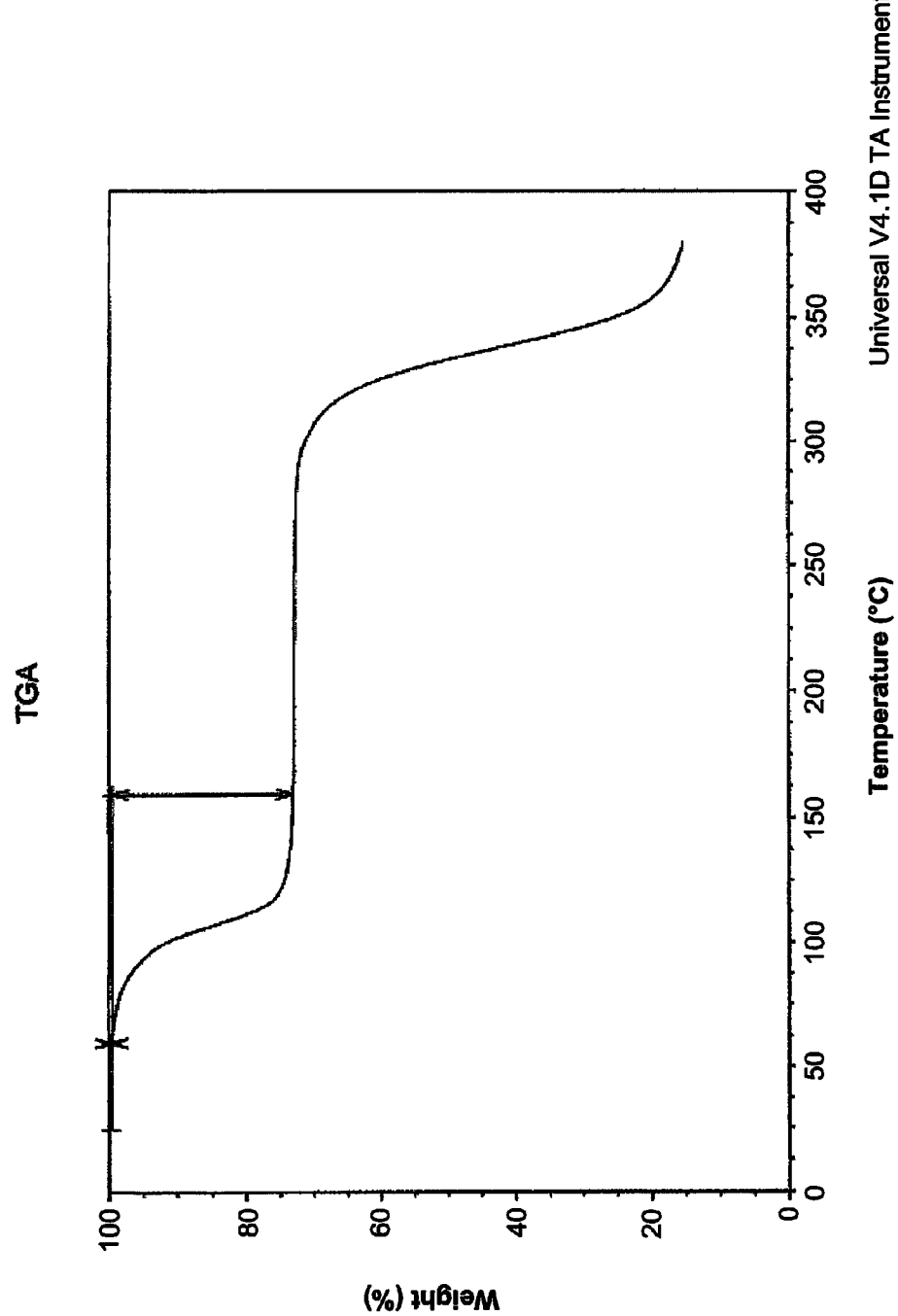
FIG. 22 is a TGA trace of Compound 1.propionic acid.
Figure 23:
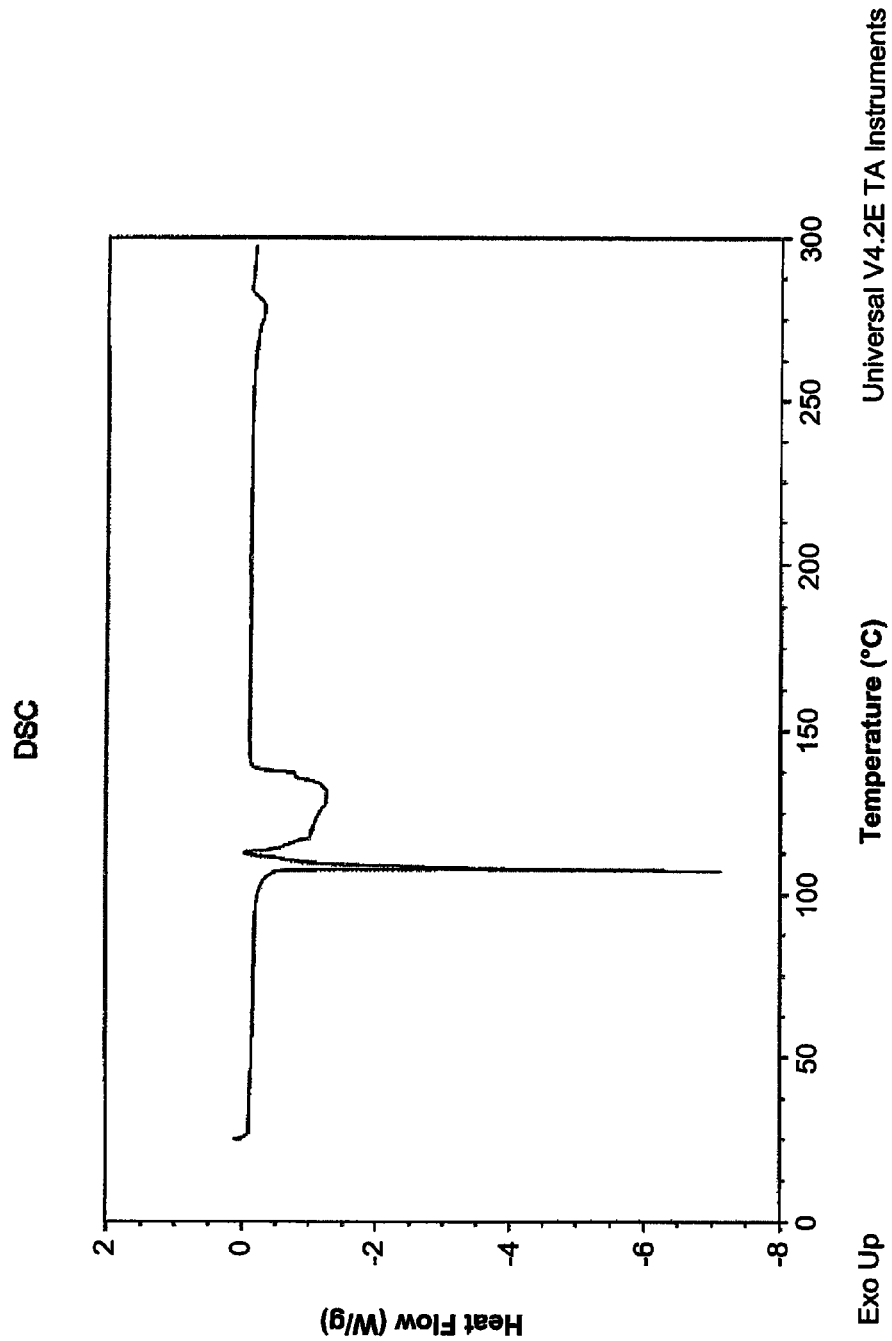
FIG. 23 is a DSC trace of Compound 1.propionic acid.
Figure 24:
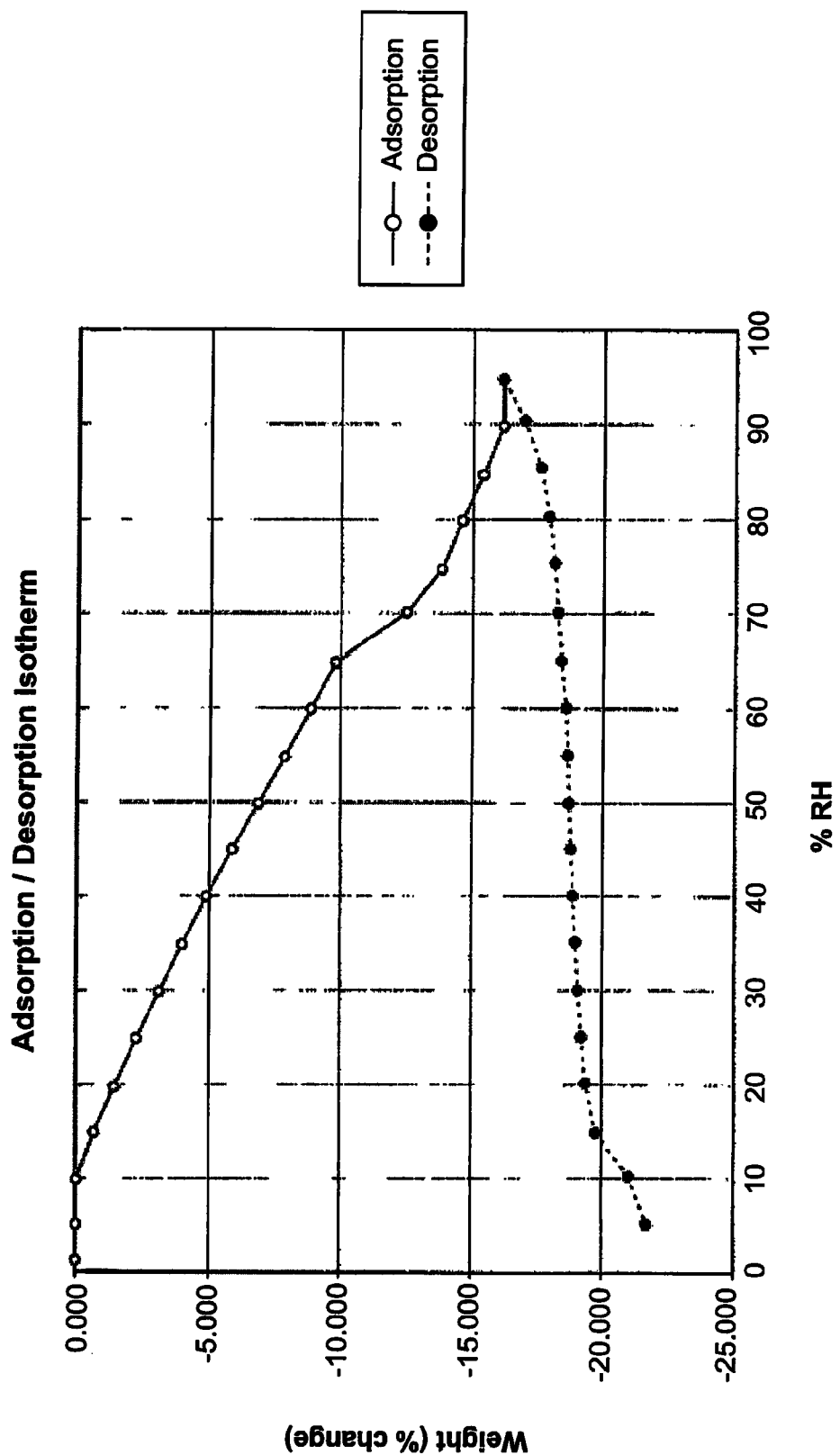
FIG. 24 is a DVS of Compound 1.propionic acid.
Figure 25:
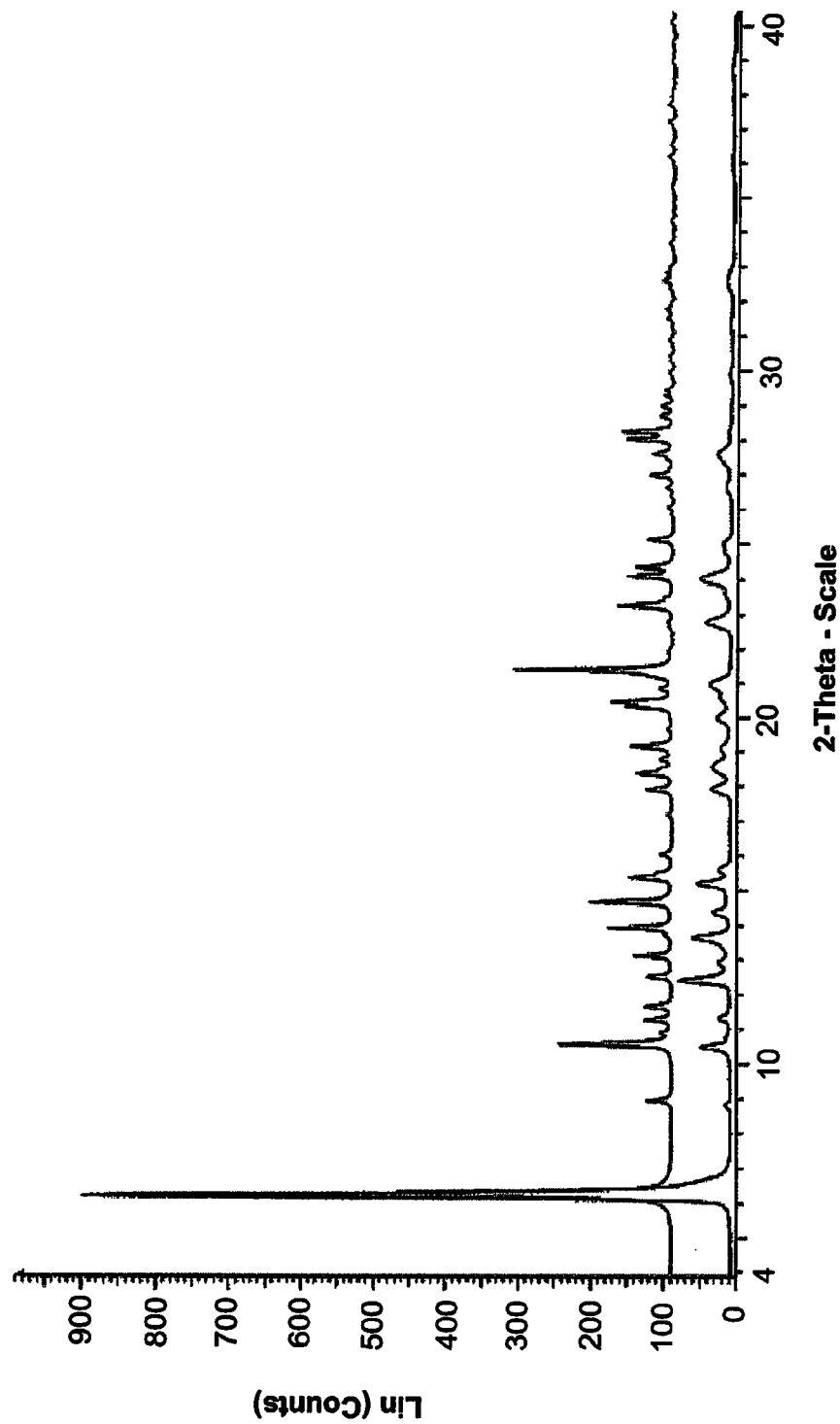
FIG. 25 is an experimental XRPD of Compound 1.ethanol. The upper trace is simulated from low temperature single crystal structure. The lower trace is an experimental pattern obtained at room temperature.
Figure 26:
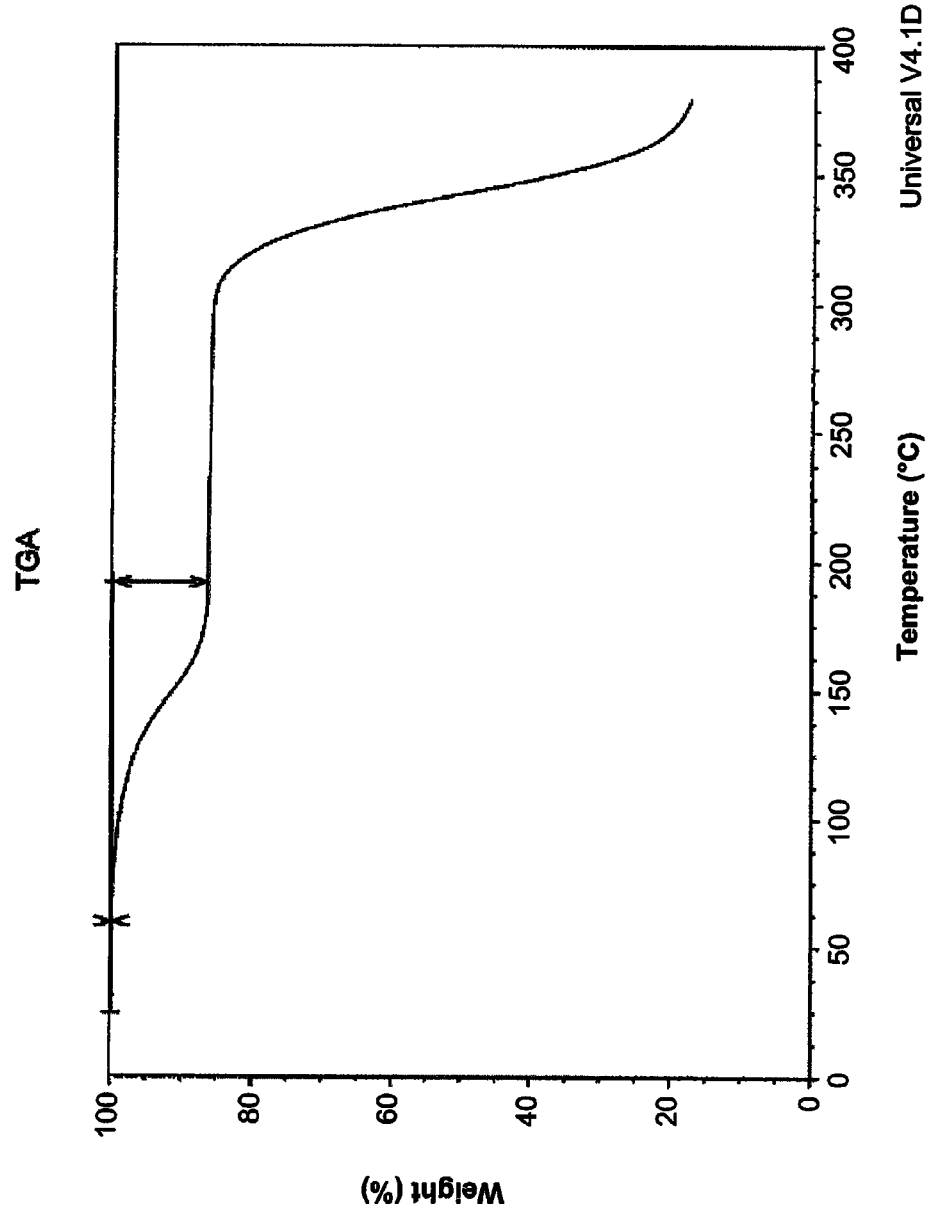
FIG. 26 is a TGA trace of Compound 1.ethanol.
Figure 27:
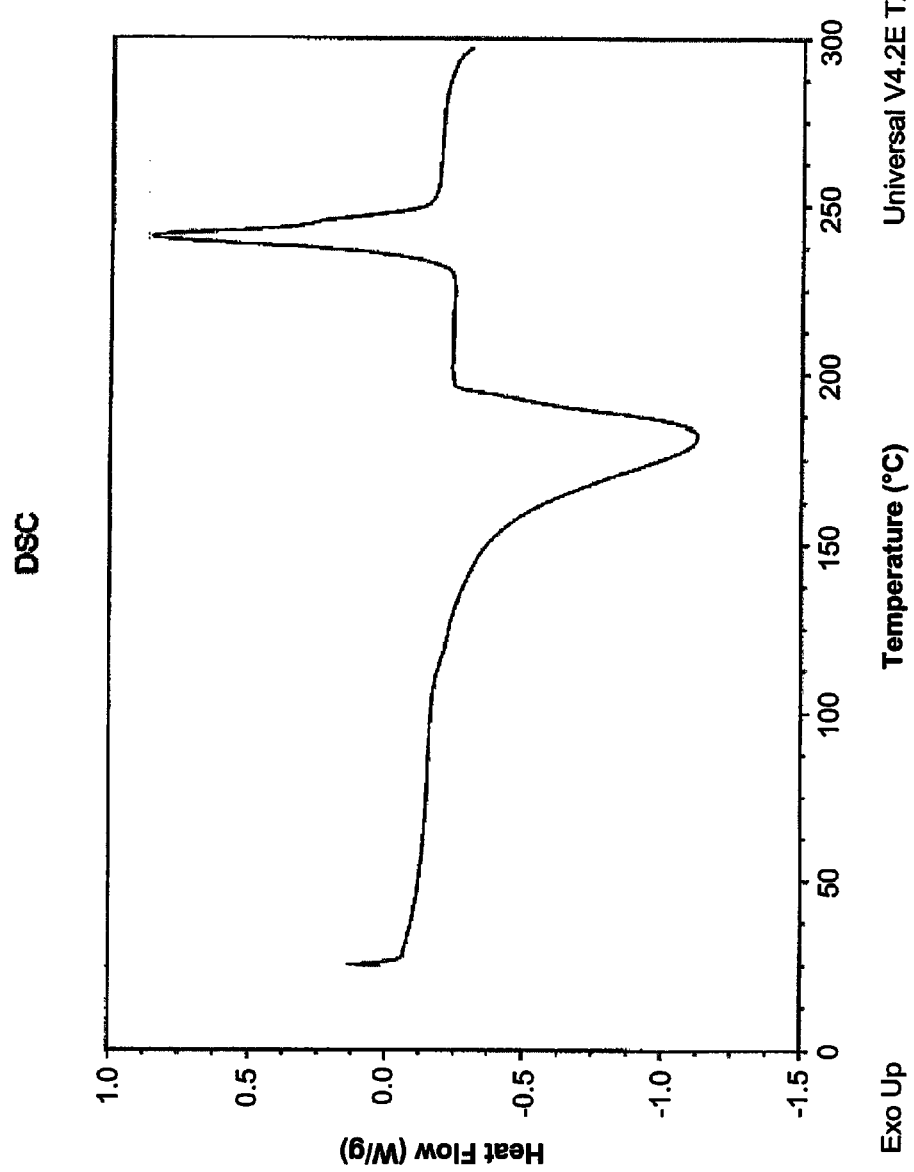
FIG. 27 is a DSC trace of Compound 1.ethanol.
Figure 28:
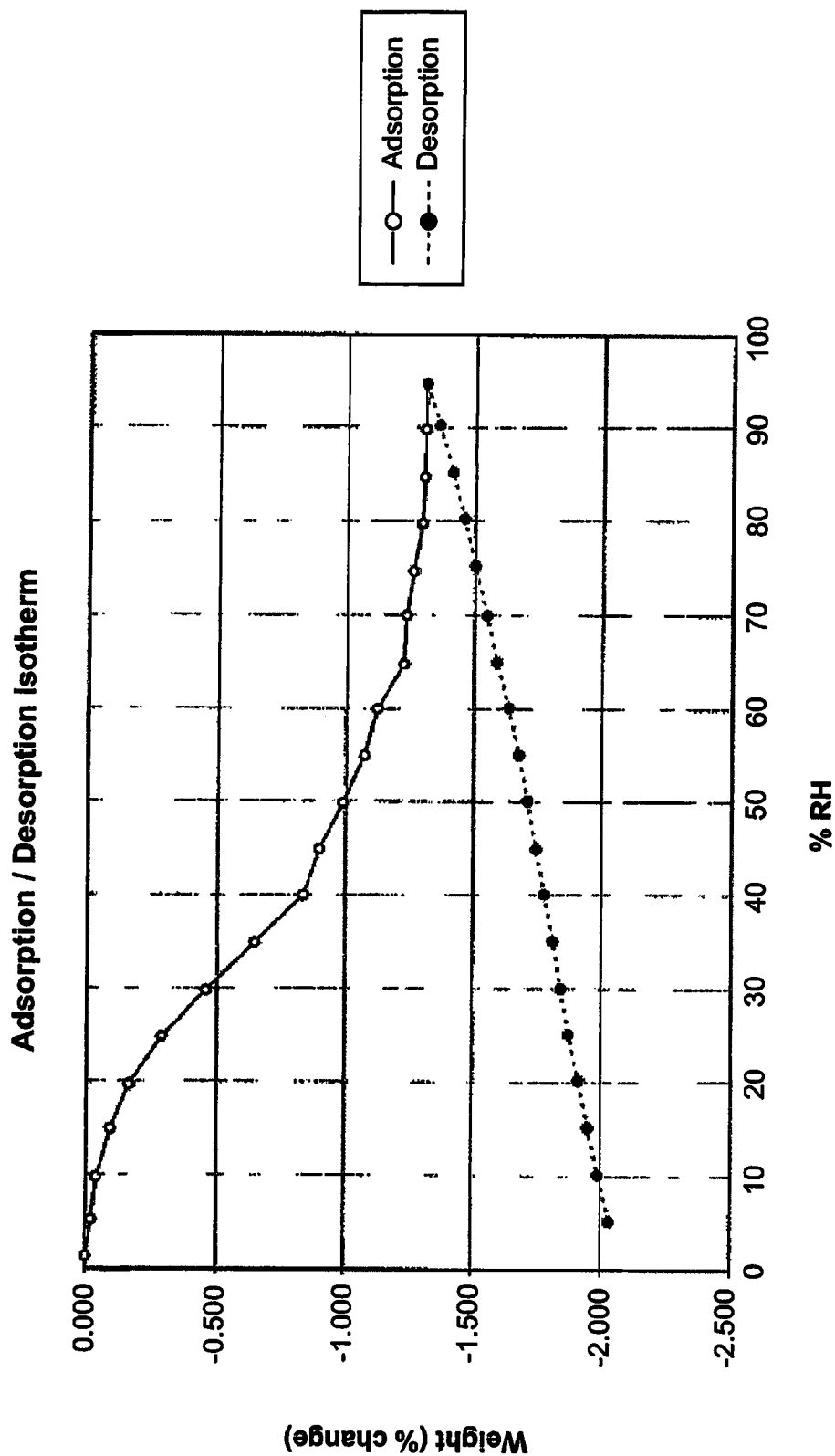
FIG. 28 is a DVS of Compound 1.ethanol.
Figure 29:
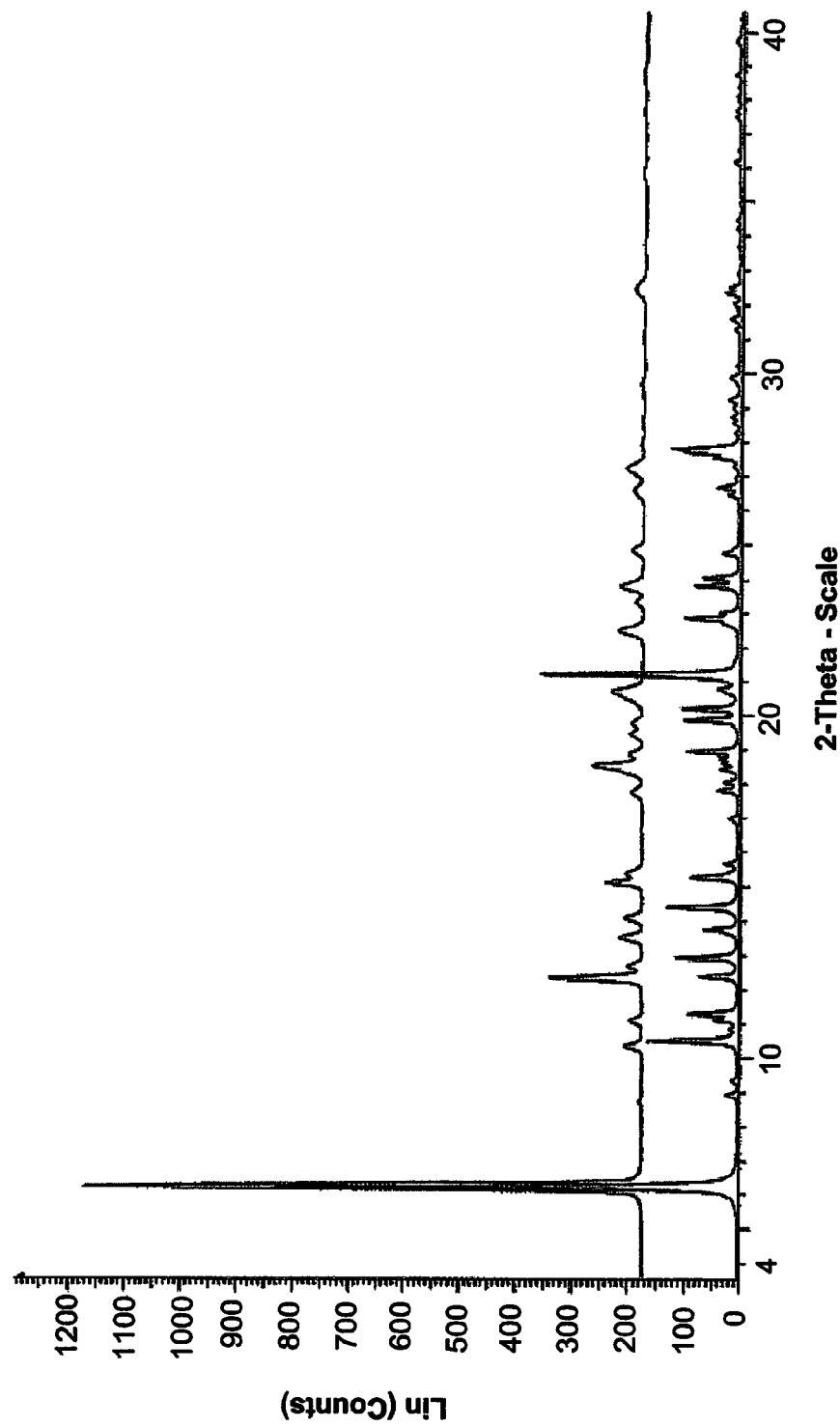
FIG. 29 is an experimental XRPD of Compound 1.2-propanol. The upper trace is simulated from low temperature single crystal structure. The lower trace is an experimental pattern obtained at room temperature.
Figure 30:
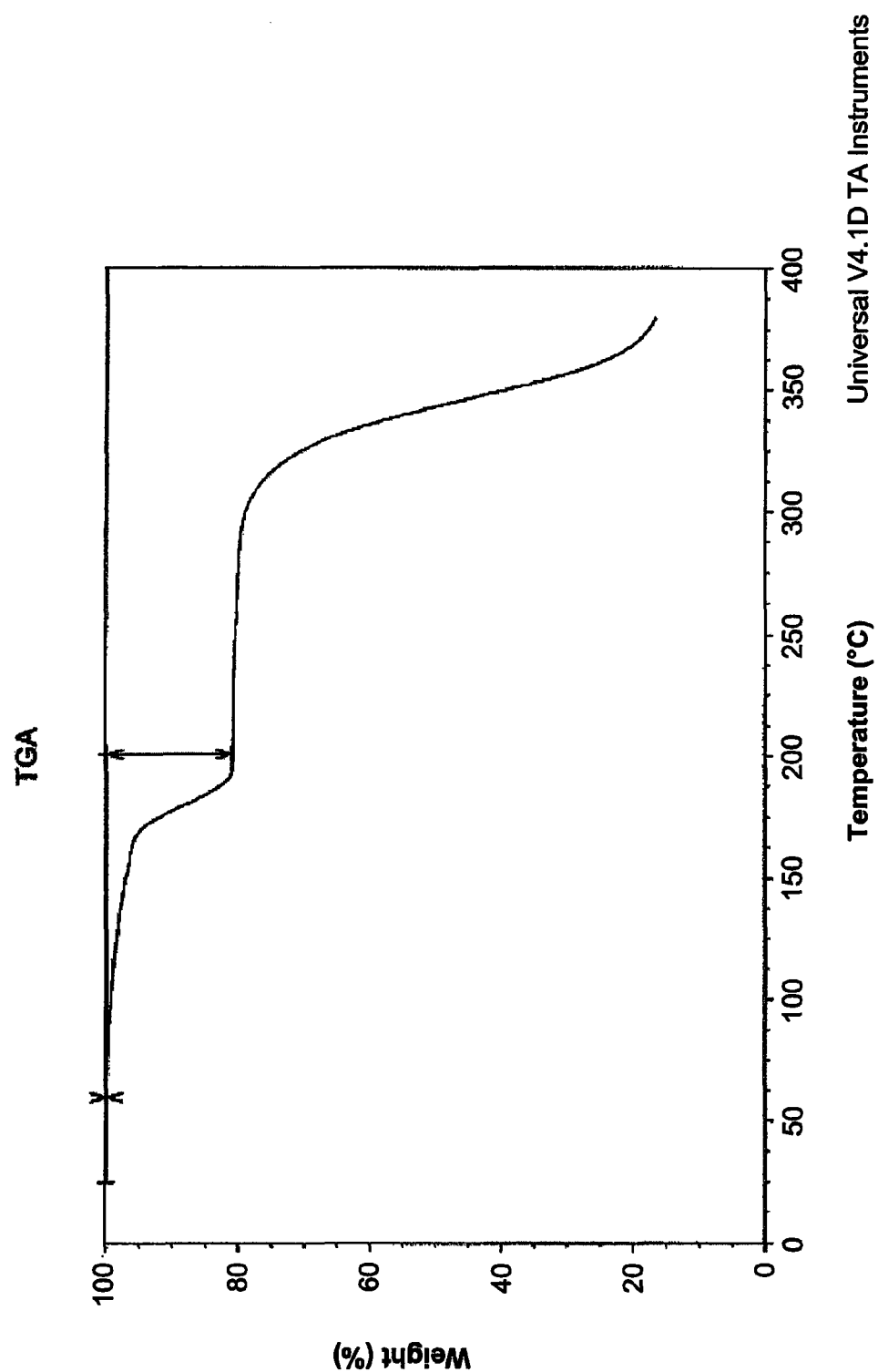
FIG. 30 is a TGA trace of Compound 1.2-propanol.
Figure 31:
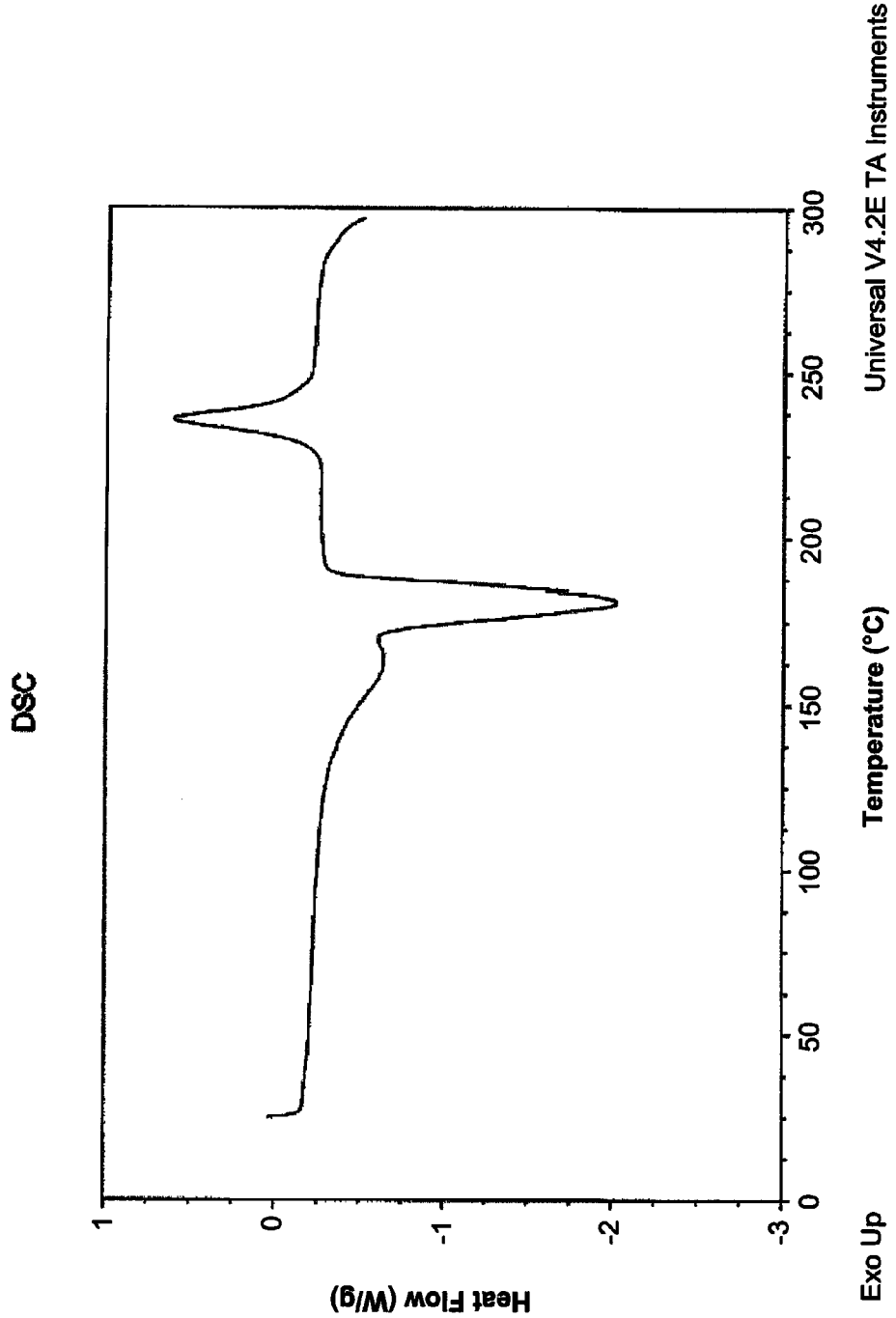
FIG. 31 is a DSC trace of Compound 1.2-propanol.
Figure 32:
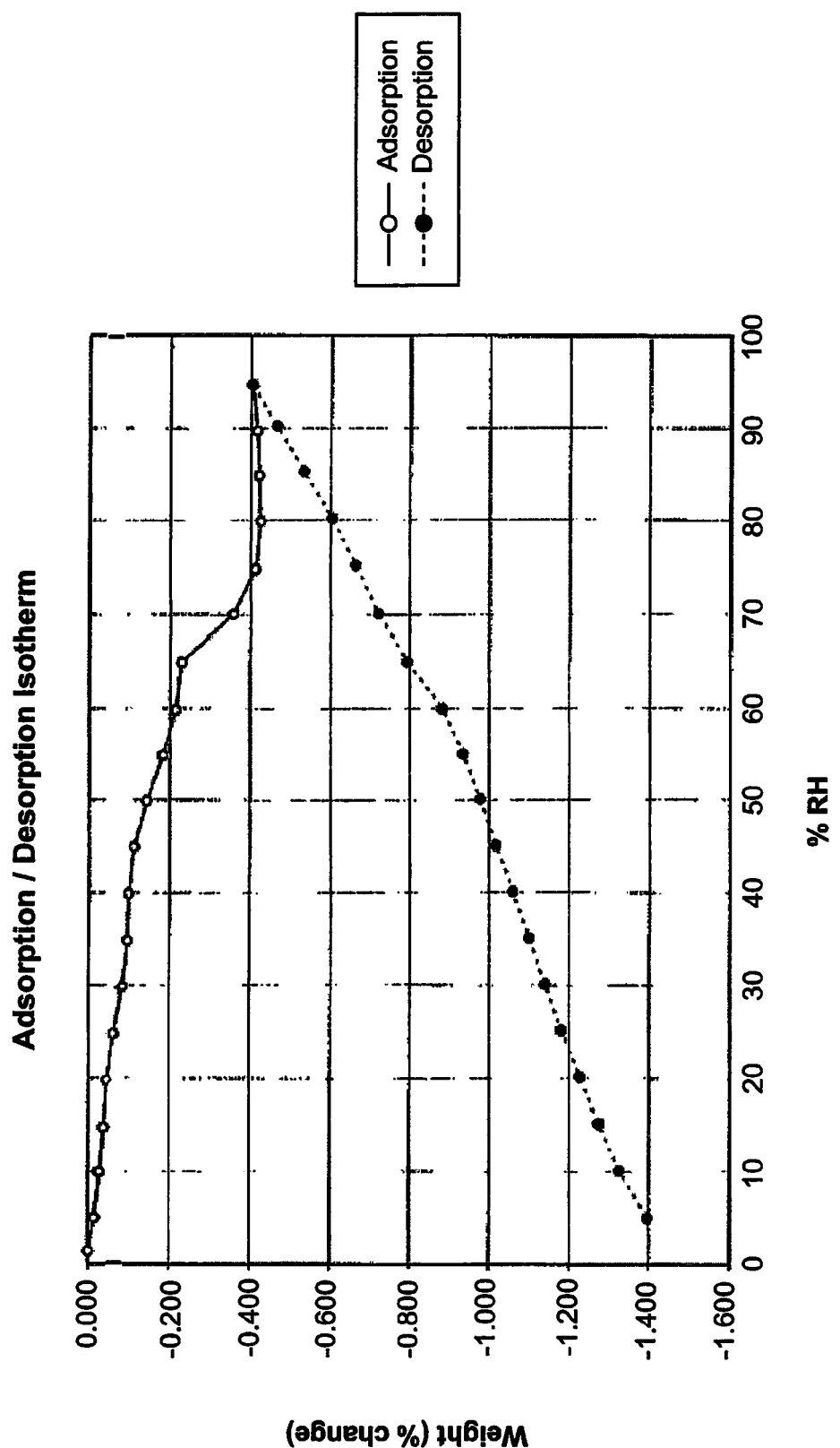
FIG. 32 is a DVS of Compound 1.2-propanol.

Solid forms of Compound 1 and Methods of Making the Same

Compound 1 has been prepared in various solid forms, including salts and co-solvates. Two crystalline forms of Compound 1, forms A and B are disclosed in U.S. application Ser. No. 11/647,505, filed on Dec. 28, 2006. Applicants describe herein 16 novel solid forms of Compound 1, including forms I, II, III, IV, V, VI, VII, VIII, IX, X, XI, XII, XIII, XIV, XV, and XVI. The reference form, name, and stoichiometry for each of these solid forms are provided in Table 1 below:

TABLE 1

| Solid forms of Compound 1. | | |
|---|---|---|
| Reference form | Name | Stoichiometry |
| I | Compound 1•2-methylbutyric acid | 1:1 |
| II | Compound 1•propylene glycol | 1:1 |

TABLE 1-continued

| Solid forms of Compound 1. | | |
|---|---|---|
| Reference form | Name | Stoichiometry |
| III | Compound 1•PEG 400•KOAc | 2:1:1:1 |
| IV | Compound 1•lactic•acid | 1:1 |
| V | Compound 1•isobutyric acid | 1:2 |
| VI | Compound 1•propionic acid | 1:2 |
| VII | Compound 1•ethanol | 1:1.5 |
| VIII | Compound 1•2-propanol | 1:1.5 |
| IX | Compound 1•H$_2$O | 1:1 |
| X | Compound 1•Besylate Form A | 1:1 |
| XI | Compound 1•Besylate Form B | 1:1 |
| XII | Compound 1•Besylate Form D | 1:1 |
| XIII | Compound 1•Besylate Form E | 1:1 |
| XIV | Compound 1•Besylate Form F | 1:1 |
| XV | Compound 1•Besylate | 2:1 |
| XVI | Compound 1•Besylate•H$_2$O | 1:2:1 |

Crystal structures of forms I, III, IV, V, VI, VII, VIII, X, XIII, XV, and XVI have been solved. The structural data of these crystal forms are given below: Data for each form was collected either on a Bruker 1000 SMART CCD diffractometer at 120K using Mo Kα radiation or on a Bruker APEX II CCD diffractometer at 100K using Cu Kα radiation. Single crystals were picked from mother liquors. The data were indexed, integrated, and scaled with the APEX software. The structures were solved and refined with the SHELX-TL package.

In some instances, Mercury software was used to simulate powder diffraction patterns from the single crystal structures.

TABLE 2

| Single crystal analysis of Forms I, III, IV, and V | | | |
|---|---|---|---|
| Reference form | I | III | IV |
| Empirical formula | C29 H38 N2 O5 | C66H93N4O17K1 | C27 H34 N2 O6 |
| Temperature | 120(2) K | 120(1) K | 100(2) K |
| Crystal system | Triclinic | Monoclinic | Triclinic |
| Space group | P-1 | P2/n | P-1 |
| Unit cell dimensions | a = 10.5124(7) Å | a = 14.550(4) Å | a = 9.0529(2) Å |
| | b = 16.1651(11) Å | b = 14.497(4) Å | b = 11.9426(2) Å |
| | c = 17.6665(11) Å | c = 16.524(4) Å | c = 12.2999(3) Å |
| | α = 102.858(2)°. | α = 90° | α = 95.6860(10)°. |
| | β = 101.656(2)°. | β = 95.922(9)° | β = 103.3120(10)°. |
| | γ = 101.066(2)°. | γ = 90° | γ = 93.1970(10)°. |
| Volume | 2776.9(3) Å$^3$ | 3466.8(15) Å$^3$ | 1283.46(5) Å$^3$ |
| Final R indices [I > 2sigma(I)] | R1 = 0.0554 wR2 = 0.1436 | R1 = 0.1285 wR2 = 0.3308 | R1 = 0.0775 wR2 = 0.1753 |

TABLE 3

| Single crystal analysis of Forms VI, VII, VIII, and IX | | | | |
|---|---|---|---|---|
| Reference form | V | VI | VII | VIII |
| Empirical formula | C32H44N2O7 | C30 H40 N2 O7 | C27 H37 N2 O4.5 | C28.50 H40 N2 O4.50 |
| Temperature | 100(2) K | 100(2) K | 100(2) K | 100(2) K |
| Crystal system | Triclinic | Triclinic | Monoclinic | Monoclinic |
| Space group | P-1 | P-1 | P 2/n | P 2/n |
| Unit cell dimensions | a = 13.3446(4) Å | a = 6.8113(6) Å | a = 16.6284(9) Å | a = 17.0032(7) Å |
| | b = 14.7878(5) Å | b = 13.1794(10) Å | b = 9.9069(6) Å | b = 9.9160(4) Å |
| | c = 18.2007(6) Å | c = 17.7558(18) Å | c = 17.1755(9) Å | c = 17.2918(7) Å |
| | α = 69.328(2)°. | α = 110.188(5)°. | α = 90°. | α = 90°. |
| | β = 79.570(2)°. | β = 95.547(6)°. | β = 113.932(2)°. | β = 113.017(2)°. |
| | γ = 68.757(2)°. | γ = 98.168(4)°. | γ = 90°. | γ = 90°. |
| Volume | 3126.28(17) Å$^3$ | 1462.5(2) Å$^3$ | 2586.2(2) Å$^3$ | 2683.36(19) Å$^3$ |
| Final R indices [I > 2sigma(I)] | R1 = 0.0448 wR2 = 0.1102 | R1 = 0.0554 wR2 = 0.1390 | R1 = 0.0313 wR2 = 0.0885 | R1 = 0.0607 wR2 = 0.1799 |

TABLE 4

Single crystal analysis of Forms X, XIII, XV and XVI

| Reference | | X | XIII | XV | XVI |
|---|---|---|---|---|---|
| Empirical formula | | C30H34N2O6S | $C_{30}H_{34}N_2O_6S$ | $C_{54}H_{62}N_4O_9S$ | $C_{36}H_{42}N_2O_{10}S_2$ |
| Temperature | | 295 K | 100 K | 295 K | 295 K |
| Crystal system | | triclinic | monoclinic | monoclinic | triclinic |
| Space group | | P1bar | $P2_1/n$ | $P2_1/c$ | P1bar |
| Unit | a | 13.507(3) Å | 10.880(2) Å | 17.579(7) Å | 10.337(4) Å |
| cell | b | 14.248(3) Å | 53.160(11) Å | 17.6686(6) Å | 10.597(4) Å |
| dimensions | c | 15.713(3) Å | 11.310(2) Å | 18.8730(6) Å | 17.606(6) Å |
| | α | 88.64(3)° | 90.0° | 90.0° | 91.385(2)° |
| | β | 70.69(3)° | 116.49(3)° | 91.334(2)° | 93.536(2)° |
| | γ | 73.07(3)° | 90.0° | 90.0° | 103.098(2)° |
| Volume | | 2721.4(9) Å3 | 5855(2) Å³ | 5860.3(4) Å³ | 1873.35(12) Å³ |
| [I > 2sigma(I)] | | 3.68 | 9.98 | 19.77 | 3.83 |

Form I

Form I can be crystallized by dissolving Compound 1 into hot 2-methyl butyric acid and subsequently cooling the solution to provide crystalline Compound 1.2-methyl butyric acid having a ratio of 1:1 Compound 1:2-methyl butyric acid, as determined by single crystal diffraction.

Form I can be characterized by having an initial weight loss of about 4.0% that is observed during the isothermal hold at 25° C. In some embodiments, Form I can be further characterized by an initial ramp from 25° C. to 60° C., likely due to residual processing solvents and/or adsorbed water. A weight loss of about 20.4% is observed in the temperature range of 60° C. to 198° C., which corresponds with the theoretical solvent weight in the stoichiometric crystal (~21%). Endothermic events(s) were observed between the temperatures of 171° C. and 176° C.

Form I is a triclinic crystal system having a P-1 space group. Form I includes one or more of the peaks provided in Table 5 below, as determined by XRPD.

TABLE 5

Representative XRPD peaks of form I

| Angle 2-Theta ° | Intensity % |
|---|---|
| 5.8 | 100.0 |
| 6.7 | 11.0 |
| 8.8 | 13.3 |
| 10.1 | 9.1 |
| 10.5 | 5.0 |
| 11.4 | 24.3 |
| 13.9 | 11.5 |
| 15.3 | 5.5 |
| 16.9 | 14.6 |
| 17.4 | 17.7 |
| 20.4 | 12.1 |

Form II

Form II can be crystallized by dissolving Compound 1 in warm/hot propylene glycol and subsequently cooling the solution to provide crystalline Compound 1.propylene glycol having a ratio of 1:1 Compound 1:propylene glycol. Form II can be characterized by a weight loss of about 16.5% as shown by TGA with an onset temperature of about 144° C., which corresponds with the theoretical solvent weight in the stoichiometric crystal (~16%). An endothermic event was observed at about 159° C., as shown by DSC.

Form II includes one or more of the peaks provided in Table 6 below, as determined by XRPD.

TABLE 6

Representative XRPD peaks of form II

| Angle 2-Theta ° | Intensity % |
|---|---|
| 10.1 | 28.2 |
| 11.7 | 100.0 |
| 12.1 | 52.2 |
| 13.3 | 17.5 |
| 13.7 | 43.2 |
| 14.2 | 24.8 |
| 15.5 | 23.4 |
| 18.1 | 50.2 |
| 19.4 | 56.4 |
| 20.5 | 62.3 |
| 22.6 | 13.4 |
| 24.6 | 21.0 |
| 25.0 | 34.0 |

Form III

Form III can be prepared using a plurality of methods. In one example, Form III is prepared by dissolving PEG and potassium acetate together and then adding PVP, once dissolved, Compound 1 was added, the solution heated, and then cooled. A seed of Compound 1.PEG 400.KOAc is added to aid crystallization of Compound 1.PEG 400.KOAc, having a 2:1:1:1 ratio of Compound 1:PEG 400:K:OAc. Form III was can also be prepared by mixing PEG and KOAc together and heating, then adding Compound 1 and EtOAc, stirring and heating the resulting mixture and then cooling to room temperature to provide crystalline Compound 1.PEG 400.KOAc. In some embodiments, PEG, KOAc, Compound 1, and EtOAc are slurried either at elevated temperature or at ambient temperature, the resulting mixture being allowed to age overnight to provide Compound 1.PEG 400.KOAc. In some embodiments, PEG, KOAc, and PVP are mixed together and heated until dissolution, Compound 1 and EtOAc are then added and stirred until dissolution, the resulting solution of which is left to age overnight to provide Compound 1.PEG 400.KOAc.

Form III can be characterized by a weight loss of about 1.7% observed between the temperature range of 140° C. to 170° C., as determined by TGA. An endotherm generally was observed at about 172° C., as determined by DSC.

Form III is characterized as having a monoclinic crystal system and a P2/n space group. Form III includes one or more of the peaks provided in Table 7 below, as determined by XRPD.

TABLE 7

Representative XRPD peaks of form III

| 2-Theta ° | Intensity % |
|---|---|
| 6.2 | 100.0 |
| 8.1 | 5.4 |
| 9.7 | 6.6 |
| 12.2 | 20.1 |
| 13.1 | 11.7 |
| 13.7 | 73.6 |
| 14.4 | 15.9 |
| 16.3 | 11.5 |
| 16.9 | 20.8 |
| 18.5 | 23.0 |
| 19.2 | 27.1 |
| 20.5 | 22.6 |

Form IV

Form IV was crystallized by dissolving Compound 1 and lactic acid into acetonitrile while heating. The solvent was slowly evaporated to provide Compound 1 lactic.acid having a 1:1 ratio of Compound 1:lactic acid. Form IV can be characterized by a sigmoidal weight loss of approximately 20.2%, as observed by TGA, with an onset temperature of approximately 173° C. This corresponds with the theoretical solvent weight in the stoichiometric crystal (~19%). An endothermic event generally was observed at approximately 170° C. was followed by endothermic event(s) in the temperature range of 275° C. to 282° C., as determined by DSC.

Form IV is characterized as having a triclinic crystal system and a P-1 space grouping. Form IV includes one or more of the peaks provided in Table 9 below, as determined by XRPD.

TABLE 8

Representative XRPD peaks of form IV

| Angle 2-Theta ° | Intensity % |
|---|---|
| 7.3 | 100.0 |
| 11.3 | 16.0 |
| 13.4 | 14.1 |
| 14.4 | 16.7 |
| 15.4 | 17.5 |
| 17.2 | 13.8 |
| 18.0 | 14.8 |
| 18.7 | 14.7 |
| 19.5 | 14.4 |
| 21.7 | 23.9 |

Form V

Form V was crystallized by dissolving Compound 1 into hot isobutyric acid and cooling the resulting solution to provide Compound 1.isobutyric acid having a ratio of 1:1 Compound 1:isobutyric acid. Form V can be characterized by a sigmoidal weight loss of approximately 30.1% as observed between the temperature range of 60° C. to 184° C., using TGA. This corresponds with the theoretical solvent weight in the stoichiometric crystal (~21%). An endothermic event was observed with a DSC thermogram, at approximately 117° C.

Form V can be characterized as having a triclinic crystal system and a P-1 space group. Form V includes one or more of the peaks provided in Table 10 below, as determined by XRPD.

TABLE 9

Representative XRPD peaks of form V

| Angle 2-Theta ° | Intensity % |
|---|---|
| 5.2 | 36.5 |
| 6.5 | 41.5 |
| 9.4 | 100.0 |
| 10.3 | 20.3 |
| 12.6 | 41.1 |
| 13.3 | 13.1 |
| 14.2 | 17.9 |
| 15.0 | 15.6 |
| 15.5 | 26.1 |
| 16.0 | 12.8 |
| 18.0 | 81.8 |
| 18.4 | 37.1 |
| 18.8 | 32.8 |
| 19.4 | 23.6 |
| 19.9 | 33.7 |
| 20.7 | 17.5 |
| 21.2 | 19.9 |
| 25.3 | 12.1 |
| 27.6 | 15.0 |

Form VI

Form VI was crystallized by dissolving Compound 1 into propionic acid, warming the solution, and then cooling to provide Compound 1.propionic acid having a ratio of 1:2 Compound 1:propionic acid. Form VI can be characterized as having a sigmoidal weight loss of approximately 26.5%, observed between the temperature range of 60° C. to 160° C. using TGA. This corresponds to the theoretical solvent weight in the stoichiometric crystal (~21%). An endothermic event generally was observed in a DSC thermogram at approximately 107° C.

Form VI can be characterized as having a triclinic crystal system and a P-1 space group. Form VI includes one or more of the peaks provided in Table 11 below, as determined by XRPD.

TABLE 10

Representative XRPD peaks of form VI

| Angle 2-Theta ° | Intensity % |
|---|---|
| 5.3 | 84.9 |
| 7.1 | 74.7 |
| 10.3 | 100.0 |
| 10.7 | 36.0 |
| 13.1 | 30.8 |
| 16.0 | 30.3 |
| 18.8 | 75.3 |
| 19.7 | 28.9 |
| 20.1 | 29.6 |

Form VII

Form VII was crystallized by dissolving Compound 1 into ethanol, warming the solution, and then cooling to provide Compound 1-ethanol, having a ratio of 1:1.5 Compound 1:ethanol. Form VII can be characterized as having a weight loss of approximately 13.4% observed in the temperature range of 60° C. to 121° C., using TGA. A broad endothermic event generally was observed in a DSC thermogram, at approximately 180° C. An exothermic event generally was observed at approximately 241° C.

Form VII can be characterized as having a monoclinic crystal system and a P2/n space group. Form VII includes one or more of the peaks provided in Table 12 below, as determined by XRPD.

TABLE 11

Representative XRPD peaks of form VII

| Angle 2-Theta ° | Intensity % |
|---|---|
| 6.2 | 100.0 |
| 10.4 | 5.2 |
| 11.3 | 2.5 |
| 12.4 | 8.6 |
| 13.6 | 6.5 |
| 14.3 | 3.4 |
| 15.1 | 5.8 |
| 15.6 | 2.7 |
| 17.9 | 3.7 |
| 18.6 | 3.6 |
| 20.0 | 2.8 |
| 21.0 | 4.0 |
| 22.8 | 4.7 |
| 24.0 | 5.5 |
| 25.0 | 2.0 |
| 27.6 | 2.9 |
| 32.6 | 1.5 |

Form VIII

Form VIII was crystallized by dissolving Compound 1 into 2-propanol, warming the solution, and then cooling to provide Compound 1.2-propanol having a ratio of 1:1.5 Compound 1:2-propanol. Form VIII can be characterized as having a weight loss of approximately 18.9% as observed between the temperature range of 60° C. to 201° C., using TGA. This corresponds with the theoretical solvent weight in the stoichiometric crystal (~19%). An endothermic event generally was observed at approximately 181° C. as determined by DSC. An exothermic event generally was observed at approximately 236° C.

Form VIII can be characterized as having a monoclinic crystal system and a P2/n space group. Form VIII includes one or more of the peaks provided in Table 13 below, as determined by XRPD.

TABLE 12

Representative XRPD peaks of form VIII

| Angle 2-Theta ° | Intensity % |
|---|---|
| 6.2 | 100.0 |
| 10.3 | 17.4 |
| 12.3 | 28.7 |
| 13.5 | 18.2 |
| 14.0 | 17.4 |
| 15.1 | 20.3 |
| 18.5 | 22.2 |
| 20.7 | 19.4 |
| 22.5 | 18.4 |
| 23.8 | 18.2 |

Form IX

Form IX was prepared by adding an excess of amorphous Compound 1 to water to form a suspension, stirring the suspension at room temperature. The solid was separated from the liquid and dried at room temperature to provide Compound 1.H$_2$O, having a ratio of 1:1 Compound 1:H$_2$O.

Form IX has a 5.9% loss between 60 and 185° C., as determined by TGA to provide for 1.37 eq. Water. Constant weight loss before melt. No sharp step at melt suggests a solvate. Form IX also is characterized by endotherms at 87 and 187° C.; re-crystallization onset 240° C.; and melt/degradation at 305° C., as determined by DSC.

Form IX includes one or more of the peaks at 2Θ, as determined by XRPD: 6.17, 7.61, 8.40, 11.02, 12.33, 14.83, 16.14, 17.11, 17.96, 18.55, 19.43, 21.05, 22.56, 23.37, 23.94, 24.86, 25.50, 26.72, 27.51, 29.60, 33.48, and 36.78.

Form X

Figure 37:
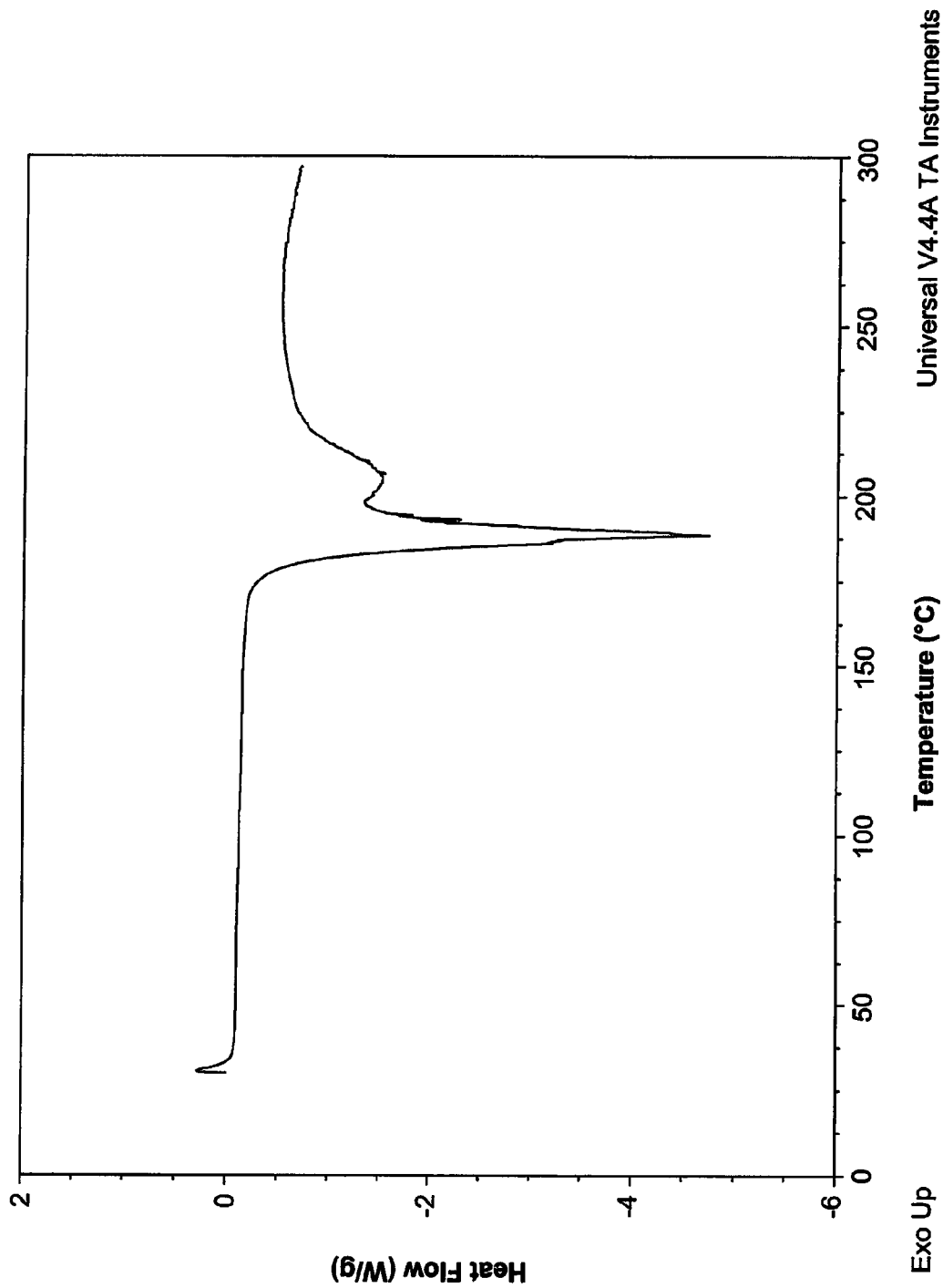
FIG. 37 is a DSC trace of Compound 1.Besylate Form A.

Form X was prepared by stirring a slurry of Compound 1, benzene sulfonic acid, and isopropyl acetate. The resulting slurry was stirred at room temperature, and filtered to provide Compound 1.besylate, having a ratio of 1:1 Compound 1:besylate. An endotherm can generally be observed by DSC at about 179° C. as shown in FIG. 37.

Form X includes one or more of the peaks provided in Table 14 below, as determined by XRPD.

TABLE 14

Representative XRPD peaks of Form X

| 2θ Angle Degree | Intensity % |
|---|---|
| 7.0 | 96 |
| 12.9 | 14 |
| 13.8 | 38 |
| 15.6 | 17 |
| 16.4 | 33 |
| 17.0 | 10 |
| 17.5 | 10 |
| 18.4 | 16 |
| 18.7 | 100 |
| 18.9 | 17 |
| 19.9 | 11 |
| 20.2 | 19 |
| 21.1 | 83 |
| 22.0 | 47 |
| 22.3 | 12 |
| 22.7 | 23 |
| 23.3 | 21 |
| 25.3 | 21 |
| 26.1 | 30 |
| 26.3 | 21 |
| 26.6 | 17 |
| 26.9 | 25 |
| 27.2 | 15 |
| 28.0 | 22 |

Form XI

Figure 39:
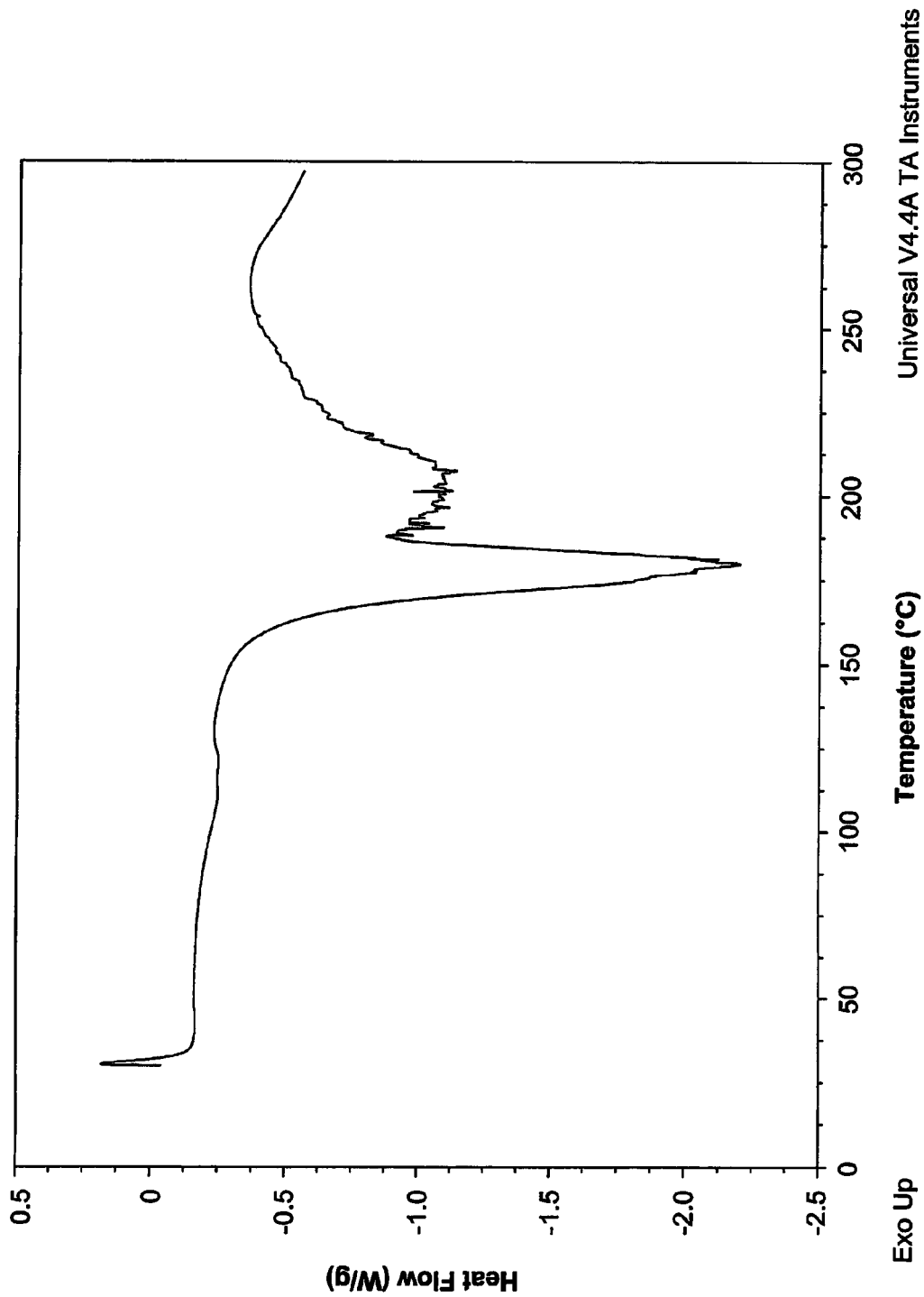
FIG. 39 is a DSC trace of Compound 1.Besylate Form B.

Form XI was prepared by stirring a slurry of Compound 1, benzene sulfonic acid, and acetonitrile. The resulting slurry was heated, allowed to cool, and filtered and dried to provide Compound 1.besylate, having a ratio of 1:1 Compound 1:besylate. An endotherm can generally be observed by DSC at about 160° C. as shown in FIG. 39.

Form XI includes one or more of the peaks provided in Table 15 below, as determined by XRPD.

TABLE 15

Representative XRPD peaks of Form XI

| 2θ angle | Intensity % |
|---|---|
| 6.2 | 100 |
| 9.4 | 11 |
| 10.7 | 15 |
| 12.5 | 12 |
| 12.8 | 17 |
| 13.6 | 11 |
| 15.2 | 48 |
| 16.5 | 17 |
| 16.7 | 19 |
| 16.9 | 19 |
| 17.5 | 31 |
| 18.0 | 12 |
| 19.1 | 24 |
| 19.4 | 12 |

TABLE 15-continued

Representative XRPD peaks of Form XI

| 2θ angle | Intensity % |
|---|---|
| 20.0 | 18 |
| 20.4 | 16 |
| 21.0 | 28 |
| 21.5 | 13 |
| 22.8 | 16 |
| 24.4 | 16 |
| 24.9 | 15 |
| 26.6 | 14 |
| 27.4 | 15 |
| 28.9 | 26 |

Form XII

Figure 41:
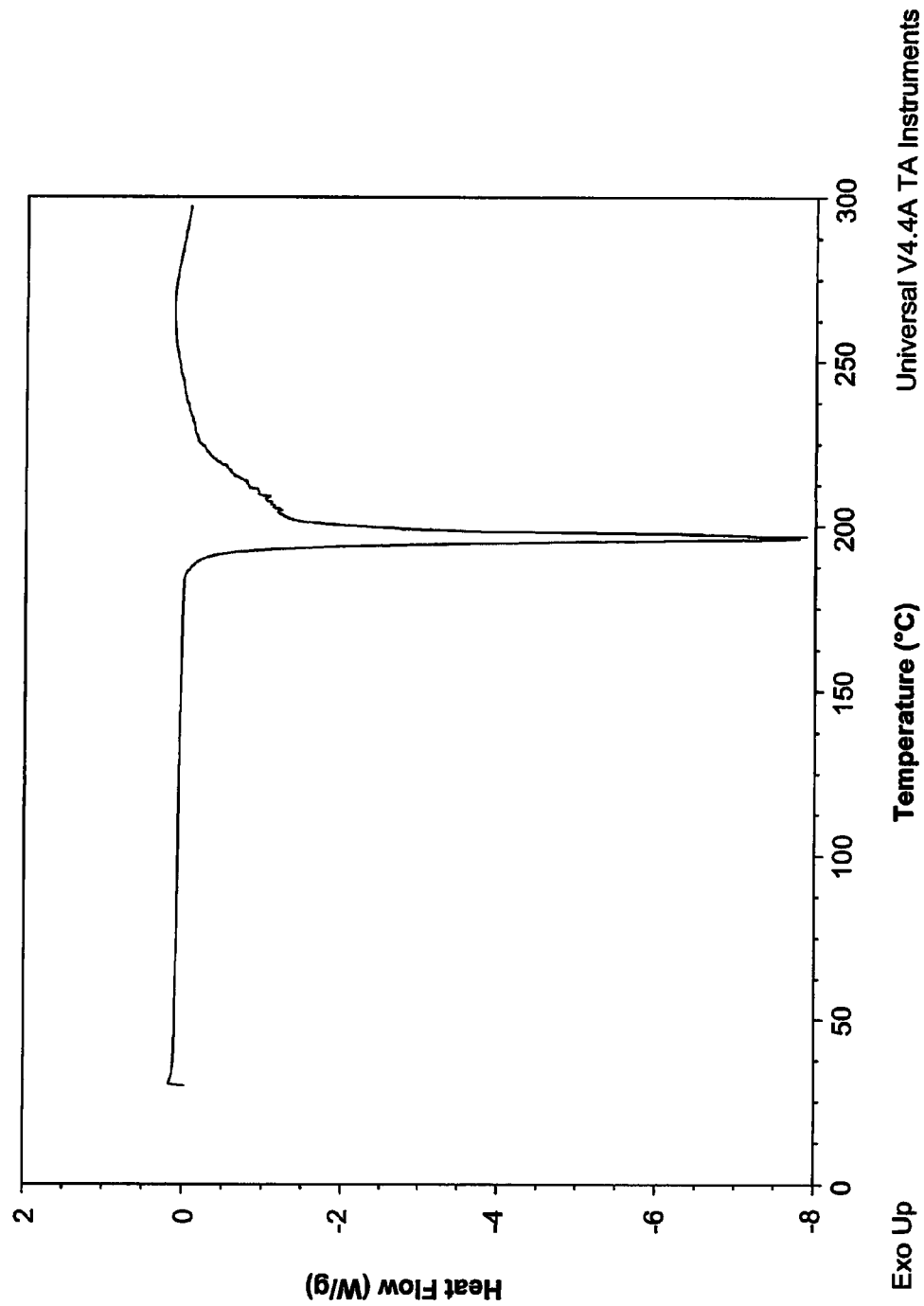
FIG. 41 is a DSC trace of Compound 1.Besylate Form D.

Form XII was prepared by stirring a slurry of Compound 1, benzene sulfonic acid, and toluene. The resulting slurry was heated, allowed to cool, and filtered to provide Compound 1.besylate, having a ratio of 1:1 Compound 1:besylate Form D. Form XII can be characterized by the onset of the first weight loss at about 183° C., as determined by TGA. An endotherm can generally be observed by DSC at about 191° C. as shown in FIG. 41.

Form XII includes one or more of the peaks provided in Table 16 below, as determined by XRPD.

TABLE 16

Representative XRPD peaks of Form XII

| 2θ angle ° | Intensity % |
|---|---|
| 6.8 | 100 |
| 12.6 | 13 |
| 13.4 | 17 |
| 15.0 | 17 |
| 16.0 | 16 |
| 16.3 | 11 |
| 16.8 | 11 |
| 17.8 | 14 |
| 18.9 | 58 |
| 19.5 | 11 |
| 21.2 | 13 |
| 21.6 | 10 |
| 23.5 | 17 |
| 26.8 | 10 |
| 29.9 | 14 |

Form XIII

Figure 44:
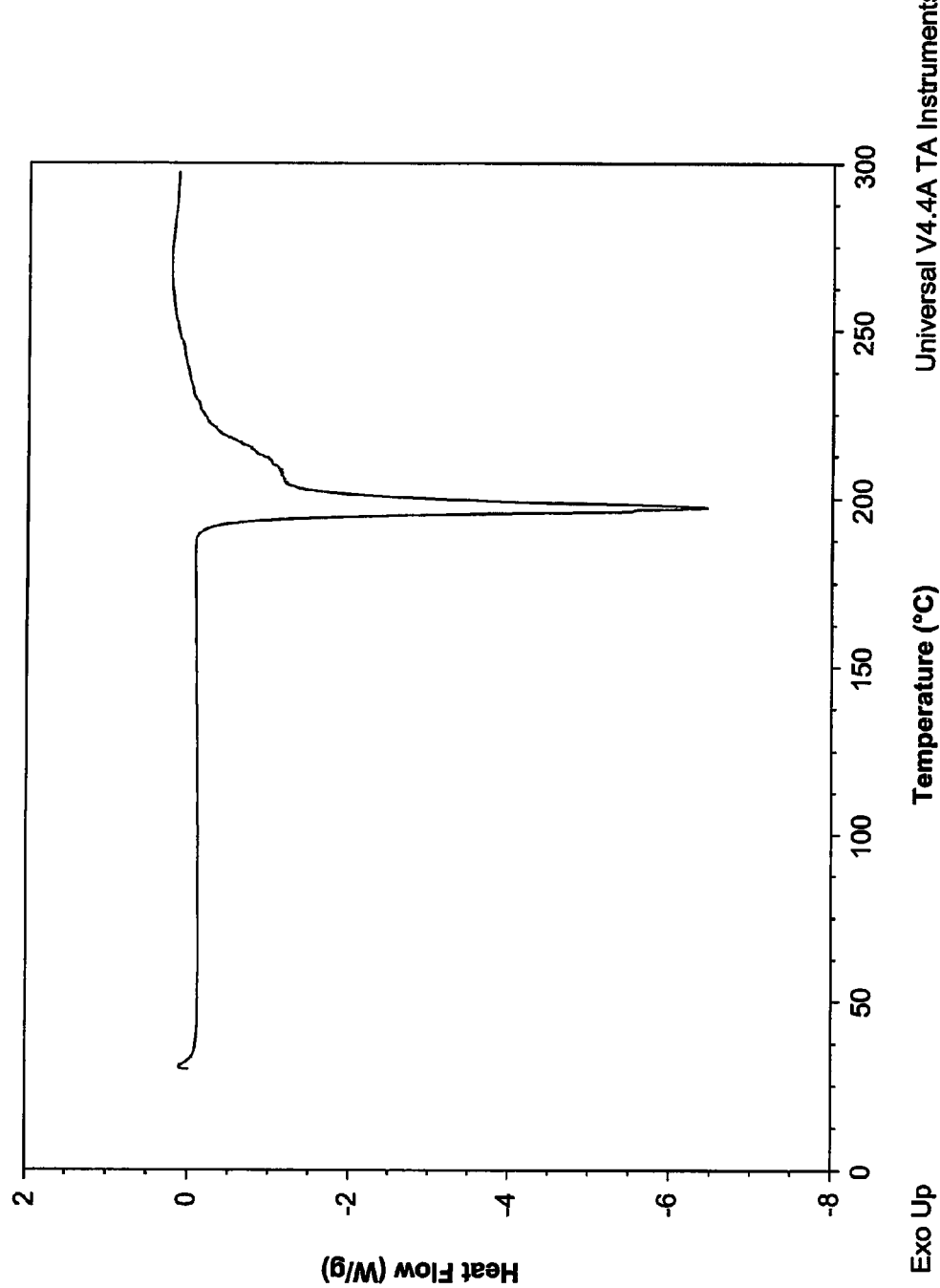
FIG. 44 is a DSC trace of Compound 1.Besylate Form E.

Form XIII was prepared by stirring a slurry of Compound 1, benzene sulfonic acid, and isopropyl acetate. The resulting slurry was heated, allowed to cool, and filtered to provide Compound 1.besylate, having a ratio of 1:1 Compound 1:besylate. Form XIII can be characterized by the onset of the first weight loss at about 184° C., as determined by TGA. An endotherm can generally be observed by DSC at about 193° C. as shown in FIG. 44.

Form XIII includes one or more of the peaks provided in Table 17 below, as determined by XRPD.

TABLE 17

Representative XRPD peaks of Form XIII

| 2θ angle 2-Theta ° | Intensity % |
|---|---|
| 3.4 | 19 |
| 6.7 | 100 |

TABLE 17-continued

Representative XRPD peaks of Form XIII

| 2θ angle 2-Theta ° | Intensity % |
|---|---|
| 9.3 | 5 |
| 10.1 | 4 |
| 11.0 | 6 |
| 11.6 | 3 |
| 12.4 | 18 |
| 12.6 | 12 |
| 13.3 | 16 |
| 14.8 | 19 |
| 15.5 | 5 |
| 16.0 | 10 |
| 16.7 | 15 |
| 17.4 | 22 |
| 17.7 | 15 |
| 18.2 | 16 |
| 18.8 | 39 |
| 19.6 | 9 |
| 20.2 | 16 |
| 20.7 | 11 |
| 21.1 | 15 |
| 21.8 | 8 |
| 22.1 | 7 |
| 22.6 | 13 |
| 23.1 | 7 |
| 23.5 | 16 |
| 23.9 | 8 |
| 24.7 | 15 |
| 25.2 | 12 |
| 25.9 | 8 |
| 26.5 | 6 |
| 27.1 | 6 |
| 27.6 | 8 |
| 28.5 | 12 |
| 29.6 | 10 |
| 30.1 | 8 |
| 30.7 | 5 |
| 31.3 | 7 |
| 31.7 | 5 |
| 32.3 | 6 |
| 33.3 | 6 |
| 34.3 | 10 |
| 34.8 | 6 |
| 35.4 | 5 |
| 35.9 | 5 |
| 36.3 | 4 |
| 36.8 | 4 |
| 37.4 | 4 |
| 38.4 | 6 |
| 39.7 | 5 |

Form XIV

Figure 47:
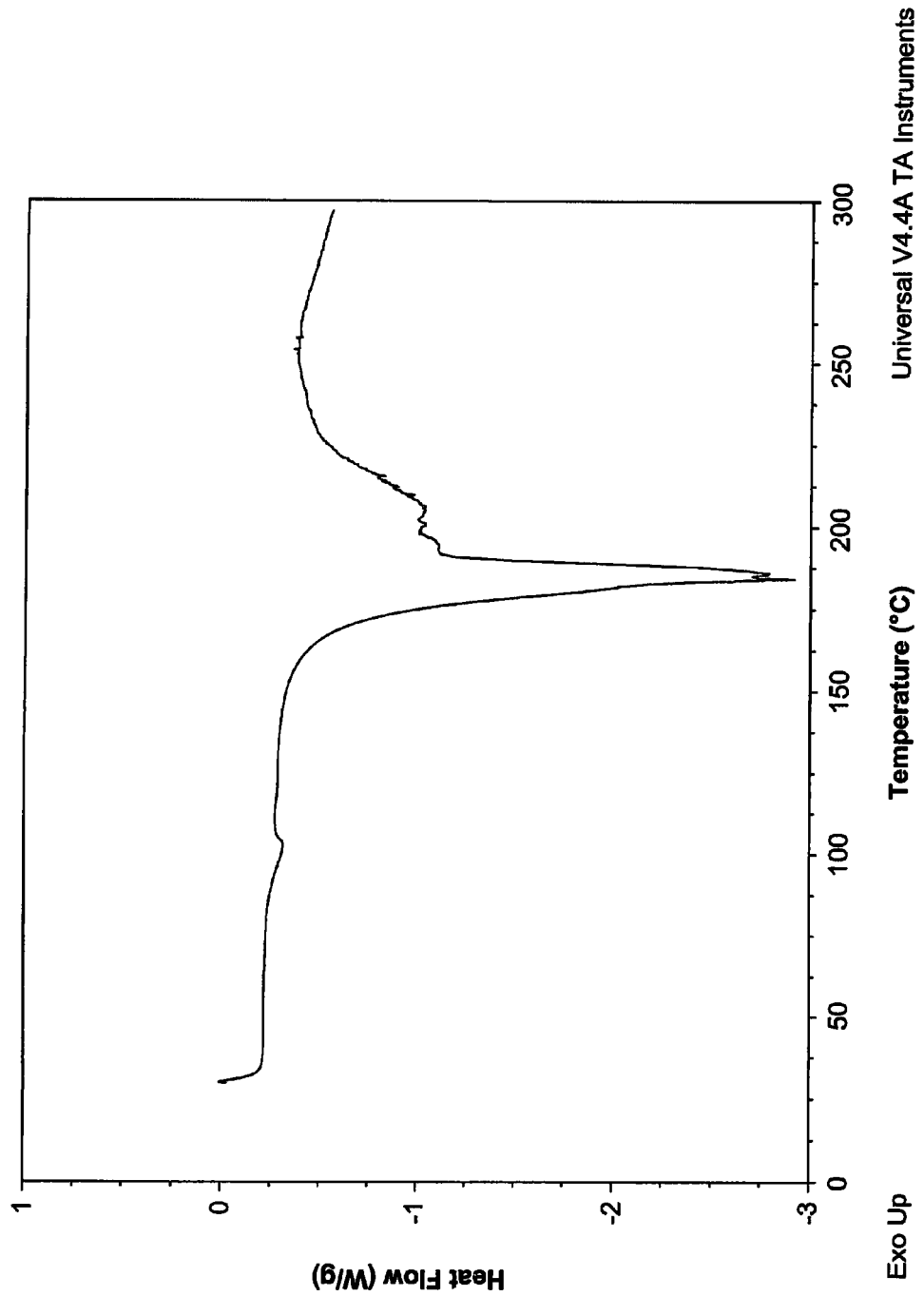
FIG. 47 is a DSC trace of Compound 1.Besylate Form F.

Form XIV was prepared by stirring a slurry of Compound 1, benzene sulfonic acid, and a mixture of 2-methyltetrahydrofuran and isopropyl acetate. The resulting slurry was heated, allowed to cool, and filtered to provide Compound 1.besylate, having a ratio of 1:1 Compound 1:besylate. An endotherm can generally be observed by DSC at about 168° C. as shown in FIG. 47.

Form XIV includes one or more of the peaks provided in Table 18 below, as determined by XRPD.

TABLE 18

Representative XRPD peaks of Form XIV

| 2θ angle ° | Intensity % |
|---|---|
| 5.0 | 10 |
| 6.5 | 93 |
| 9.4 | 19 |
| 12.0 | 22 |

TABLE 18-continued

Representative XRPD peaks of Form XIV

| 2θ angle ° | Intensity % |
|---|---|
| 12.4 | 13 |
| 12.7 | 37 |
| 13.2 | 31 |
| 14.7 | 12 |
| 15.2 | 15 |
| 15.7 | 35 |
| 16.2 | 30 |
| 16.5 | 61 |
| 16.9 | 21 |
| 17.3 | 30 |
| 17.7 | 28 |
| 17.9 | 40 |
| 18.6 | 100 |
| 18.8 | 62 |
| 19.1 | 27 |
| 19.7 | 59 |
| 20.2 | 20 |
| 20.5 | 19 |
| 20.8 | 25 |
| 21.0 | 28 |
| 21.6 | 23 |
| 21.9 | 18 |
| 22.1 | 15 |
| 22.7 | 11 |
| 23.4 | 20 |
| 24.0 | 59 |
| 24.9 | 17 |
| 25.2 | 14 |
| 25.7 | 21 |
| 26.0 | 16 |
| 26.6 | 24 |
| 26.9 | 16 |
| 27.6 | 24 |
| 28.1 | 19 |
| 28.7 | 20 |
| 29.3 | 21 |
| 30.0 | 15 |

Form XV

Form XV was prepared by stirring a slurry of Compound 1, 0.6 equivalents benzene sulfonic acid, and isopropyl acetate. The resulting slurry was stirred at room temperature, and filtered to provide Compound 1.besylate, having a ratio of 2:1 Compound 1:besylate.

Form XV includes one or more of the peaks provided below in Table 19, as determined by XRPD.

TABLE 19

Representative XRPD peaks of Form XV

| 2θ angle Obs | Intensity % |
|---|---|
| 5.2 | 76 |
| 8.7 | 32 |
| 10.2 | 31 |
| 10.7 | 35 |
| 11.2 | 74 |
| 12.4 | 71 |
| 13.9 | 43 |
| 14.9 | 100 |
| 15.2 | 68 |
| 16.1 | 40 |
| 17.4 | 61 |
| 18.0 | 43 |
| 18.6 | 96 |
| 19.0 | 26 |
| 19.6 | 30 |
| 20.5 | 20 |
| 20.9 | 35 |

TABLE 19-continued

Representative XRPD peaks of Form XV

| 2θ angle Obs | Intensity % |
|---|---|
| 21.4 | 31 |
| 22.9 | 33 |
| 23.3 | 45 |
| 23.7 | 29 |
| 24.0 | 20 |
| 24.7 | 65 |
| 26.1 | 24 |
| 26.6 | 29 |
| 27.6 | 26 |
| 28.7 | 22 |
| 29.5 | 21 |

Form XVI

Figure 51:
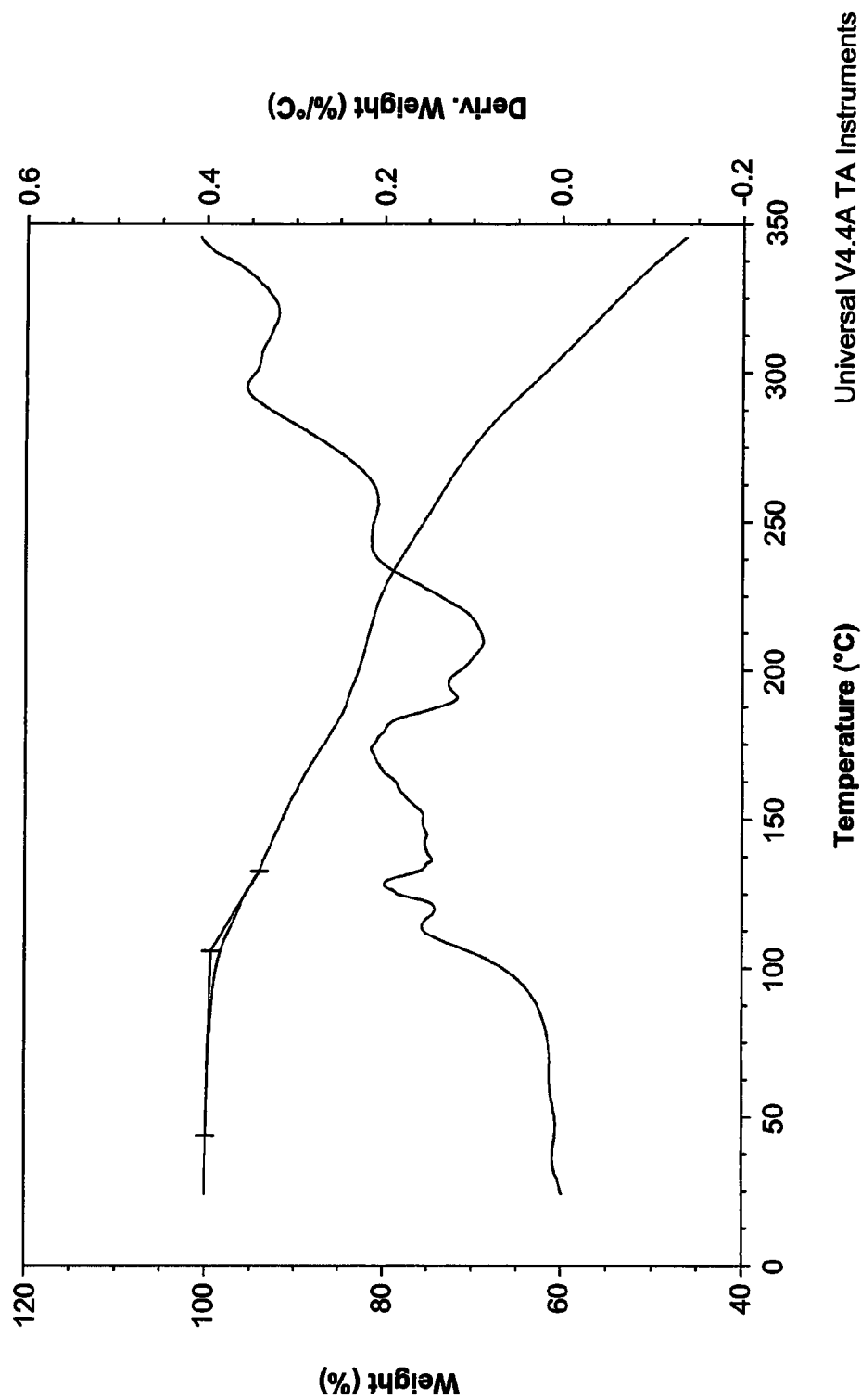
FIG. 51 is a TGA trace of Compound 1.Besylate.H$_2$O.

Form XVI was prepared by stirring a slurry of Compound 1.besylate (1:1), benzene sulfonic acid, ethyl acetate, and isopropyl acetate. The resulting slurry was stirred at room temperature, and filtered to provide Compound 1.besylate, having a ratio of 1:2:1 Compound 1:besylate:$H_2O$. Form XVI can be characterized by the onset of the first weight loss at about 106° C., as determined by TGA. An endotherm can generally be observed by DSC at about 103° C. as shown in FIG. 51.

Form XVI includes one or more of the peaks provided below in Table 20, as determined by XRPD.

TABLE 20

Representative XRPD peaks of Form XVI

| 2θ angle Obs | Intensity % |
|---|---|
| 5.1 | 100 |
| 8.7 | 1 |
| 10.2 | 2 |
| 12.1 | 1 |
| 13.1 | 3 |
| 13.6 | 1 |
| 14.0 | 1 |
| 17.8 | 4 |
| 18.2 | 3 |
| 18.5 | 1 |
| 19.8 | 1 |
| 20.3 | 5 |
| 21.1 | 2 |
| 21.8 | 4 |
| 22.6 | 2 |
| 22.9 | 2 |
| 23.3 | 1 |
| 23.6 | 1 |
| 24.2 | 3 |
| 24.5 | 2 |
| 25.4 | 7 |
| 26.1 | 3 |
| 26.5 | 2 |
| 26.9 | 1 |
| 27.3 | 3 |
| 27.6 | 2 |

Methods of Using Compound 1 and Solid Forms Thereof

In yet another aspect, the present invention provides a method of treating a condition, disease, or disorder implicated by CFTR. In certain embodiments, the present invention provides a method of treating a condition, disease, or disorder implicated by a deficiency of CFTR activity, the method comprising administering a composition comprising a solid state form of Compound 1 described herein to a subject, preferably a mammal, in need thereof (e.g., one of Forms I through XVI).

A "CFTR-mediated disease" as used herein is a disease selected from cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

In certain embodiments, the present invention provides a method of treating cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, comprising the step of administering to said mammal an effective amount of a composition comprising a solid state form of Compound 1 described herein (e.g., one of Forms I through XVI).

According to an alternative preferred embodiment, the present invention provides a method of treating cystic fibrosis comprising the step of administering to said mammal a composition comprising a solid state form of Compound 1 described herein (e.g., one of Forms I through XVI).

According to the invention an "effective amount" of a solid state form of Compound 1 or a pharmaceutically acceptable composition thereof is that amount effective for treating or lessening the severity of any of the diseases recited above.

A solid state form of Compound 1 or a pharmaceutically acceptable composition thereof (e.g., one of Forms I through XVI) may be administered using any amount and any route of administration effective for treating or lessening the severity of one or more of the diseases recited above.

In certain embodiments, a solid state form of Compound 1 described herein (e.g., one of Forms I through XVI) or a pharmaceutically acceptable composition thereof is useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl$^-$ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In one embodiment, a solid state form of Compound 1 described herein (e.g., one of Forms I through XVI) or a pharmaceutically acceptable composition thereof is useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Transmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, a solid state form of Compound 1 described herein (e.g., one of Forms I through XVI) or a pharmaceutically acceptable composition thereof is useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar--agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the solid state form of Compound 1 described herein (e.g., one of Forms I through XVI) or a pharmaceutically acceptable composition thereof can be employed in combination therapies, that is, a solid form described herein or a pharmaceutically acceptable composition thereof can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

A solid state form of Compound 1 described herein (e.g., one of Forms I through XVI) or a pharmaceutically acceptable composition thereof may also be incorporated into compositions for coating an implantable medical device, such as prostheses, artificial valves, vascular grafts, stents and catheters. Accordingly, the present invention, in another aspect, includes a composition for coating an implantable device comprising a solid state form of Compound 1 described herein or a pharmaceutically acceptable composition thereof, and in classes and subclasses herein, and a carrier suitable for coating said implantable device. In still another aspect, the present invention includes an implantable device coated with a composition comprising a solid state form of Compound 1 described herein (e.g., one of Forms I through XVI) or a pharmaceutically acceptable composition thereof, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

EXAMPLES

Unless otherwise noted, the XRD data were collected on a Bruker D8 Discover powder diffractometer with Highstar area detector. Cu Kα seal tube radiation was used at 40 kV, 35 mA. The samples were placed on zero-background silicon wafers at room temperature. For each sample, two data frames were collected at 120 seconds each at 2 different 2θ angles: 8° and 26°. The frames data were integrated with GADDS software and merged with EVA software.

Form V data were collected on an Inel Equinox 1000 diffractometer with Cu Kα1 radiation. Sample was placed on an aluminum plate. Thermal gravimetric analysis (TGA) was performed with a TGA Q500 V6.3 Build 189 (TA Instruments, New Castle, Del.) was used for TGA measurement. Temperature was equilibrated by Curie point with nickel. Samples of 10-20 mg were equilibrated and held at 25° C. for 60 min and then scanned from 25° C. to 300° C. at a heating rate of 10° C./min. A nitrogen gas balance purge of 10 ml/min and a sample purge of 90 ml/min were used. Data were collected by Thermal Advantage Q Series™ software version 2.2.0.248 and analyzed by Universal Analysis software version 4.1D (TA Instruments, New Castle, Del.). The reported numbers represent single analyses.

Differential scanning calorimetry (DSC) was performed using a DSC Q100 V9.6 Build 290 (TA Instruments, New Castle, Del.). Temperature was calibrated with indium and heat capacity was calibrated with sapphire. Samples of 3-6 mg were weighed into aluminum pans that were crimped using lids with 1 pin hole. The samples were equilibrated at 30° C. and scanned from 25° C. to 300° C. at a heating rate of 10° C./min and with a nitrogen gas purge of 50 ml/min. Data were collected by Thermal Advantage Q Series™ version 2.2.0.248 software and analyzed by Universal Analysis software version 4.1D (TA Instruments, New Castle, Del.). The reported numbers represent analysis performed in triplicate.

Isothermal sorption-desorption (DVS) was performed at 25° C. using a VTI symmetric vapor sorption analyzer, model SGA-100. The temperature was 25° C. The relative humidity (RH) range studied was 5% to 95% RH with 5% RH steps, an equilibrium criterion of 0.01 wt % and a maximum equilibration time of 180 min.

Example 1

Form I 70 g of Compound 1 is dissolved in 4500 ml of hot (110° C.) 2 Methyl Butyric acid, the solution is then cooled to −5° C. and aged overnight. A sample of Form I was analyzed using a plurality of analytical techniques. FIGS. 1, 2, 3, and 4 respectively depict an experimental XRPD of Form C, a TGA trace of Form C, a DSC of Form I, and a DVS of Form I, each of which were obtained using the methods described above.

Example 2

Form II

Form II was prepared using the two methods described below.
1. 54.58 g of Compound 1 was dissolved in 4500 ml of propylene glycol at 100° C. The solution was slow cooled to −5° C. over 24 hrs, and the solid was then filtered.

2. 40 g of Compound 1 dissolved in 4500 ml of propylene glycol at +85° C., solution cooled to −5° C. and aged overnight. Solids filtered and washed with approximately 60 ml acetone to remove excess propylene glycol and then vacuum dried to remove excess acetone.

A sample of Form II was analyzed using a plurality of analytical techniques. FIGS. 5, 6, 7, and 8 respectively depict an experimental XRPD of Form D, a TGA trace of Form II, a DSC of Form II, and a DVS of Form II, each of which were obtained using the methods described above.

Example 3

Form III

Form III was prepared using the five methods described below.
1. 510 g PEG was heated to 75° C., 30 g of Potassium acetate was added and stirred to dissolution, and 12 g of PVP slowly added and stirred to dissolution. 48 g Compound 1 was added and stirred to dissolution with heating to 85° C. The solution was then cooled to RT and 1% w/w Compound 1 PEG/KOAc co-form added was as a seed. The mixture was aged overnight to provide Form III.
2. PEG 22.91 g and KOAc 8.70 g were heated to +80C, 10 g of Compound 1 was added, 20.548 g of EtOAc, and the system stirred at +85° C. The system was then cooled to room temperature to provide Form III.
3. PEG (3.10 g), KOAc (0.6 g), 2.5 g Compound 1 and 9.25 g EtOAc were slurried at 75 C for 4 hrs, then cooled to RT and aged overnight to provide Form III.
4. 3.1 g of PEG, 0.6 g KOAc, 2.56 g Compound 1 and 9.25 g of EtOAc were slurried at ambient conditions overnight to provide Form III.
5. 22.5 g PEG, KOAc 1.36 g, PVP 6 g where heated until dissolution, approx 80° C. 24 g Compound 1 and 240 g EtOAc were then added and stirred until dissolution. The resulting solution was cooled to room temperature and aged overnight. 0.5 g seed added at RT to provide form III.

A sample of Form III was analyzed using a plurality of analytical techniques. FIGS. 9, 10, 11, and 12 respectively depict an experimental XRPD of Form III, a TGA trace of Form III, a DSC of Form III, and a DVS of Form III, each of which were obtained using the methods described above.

Example 4

Form IV

Compound 1, 100 mg, lactic acid 2 ml, acetonitrile 120 ml were heated to dissolve the mixture, slow evaporation of the solvent provided solids of Form IV.

A sample of Form V was analyzed using a plurality of analytical techniques. FIGS. 13, 14, 15, and 16 respectively depict an experimental XRPD of Form IV, a TGA trace of Form IV, a DSC of Form IV, and a DVS of Form IV, each of which were obtained using the methods described above.

Example 5

Form V 50 g of Compound 1 was dissolved in hot Isobutyric acid 90-100° C., cooled to 5° C. over several hours, and aged overnight. The resulting slurry was filtered and dried using a rotavap to provide Form V.

A sample of Form V was analyzed using a plurality of analytical techniques. FIGS. 17, 18, 19, and 20 respectively depict an experimental XRPD of Form V, a TGA trace of Form V, a DSC of Form V, and a DVS of Form V, each of which were obtained using the methods described above.

Example 6

Form VI 40 g of Compound 1 was dissolved in 4000 ml of propionic acid at 65° C., the resulting solution was cooled to −5° C. and aged overnight. The resulting solid was vacuum filtered to dryness to provide Form VI.

A sample of Form VI was analyzed using a plurality of analytical techniques. FIGS. 21, 22, 23, and 24 respectively depict an experimental XRPD of Form VI, a TGA trace of Form VI, a DSC of Form VI, and a DVS of Form VI, each of which were obtained using the methods described above.

Example 7

Form VII 40-50 g Compound 1 was dissolved in ethanol at a temperature of from about 60° C. to about 80° C., and the solution was then cooled to −5° C. and aged overnight. The product was isolated by filtration and vacuum dried at 40° C. for 1 hour to provide Form VII.

A sample of Form VII was analyzed using a plurality of analytical techniques. FIGS. 25, 26, 27, and 28 respectively depict an experimental XRPD of Form VII, a TGA trace of Form VII, a DSC of Form VII, and a DVS of Form VII, each of which were obtained using the methods described above.

Example 8

Form VIII 40-50 g of Compound 1 was dissolved in hot 2-propanol and cooled to −5° C. The resulting slurry was aged overnight. The product was isolated by filtration after 1 hour to provide Form VIII.

A sample of Form VIII was analyzed using a plurality of analytical techniques. FIGS. 29, 30, 31, and 32 respectively depict an experimental XRPD of Form VIII, a TGA trace of Form VIII, a DSC of Form VIII, and a DVS of Form VIII, each of which were obtained using the methods described above.

Example 9

Form IX

An excess of amorphous Compound 1 was added to water to form a suspension and the suspension was stirred for two hours at room temperature. The solid was separated from the liquid and dried at room temperature to provide Form IX.

Figure 33:
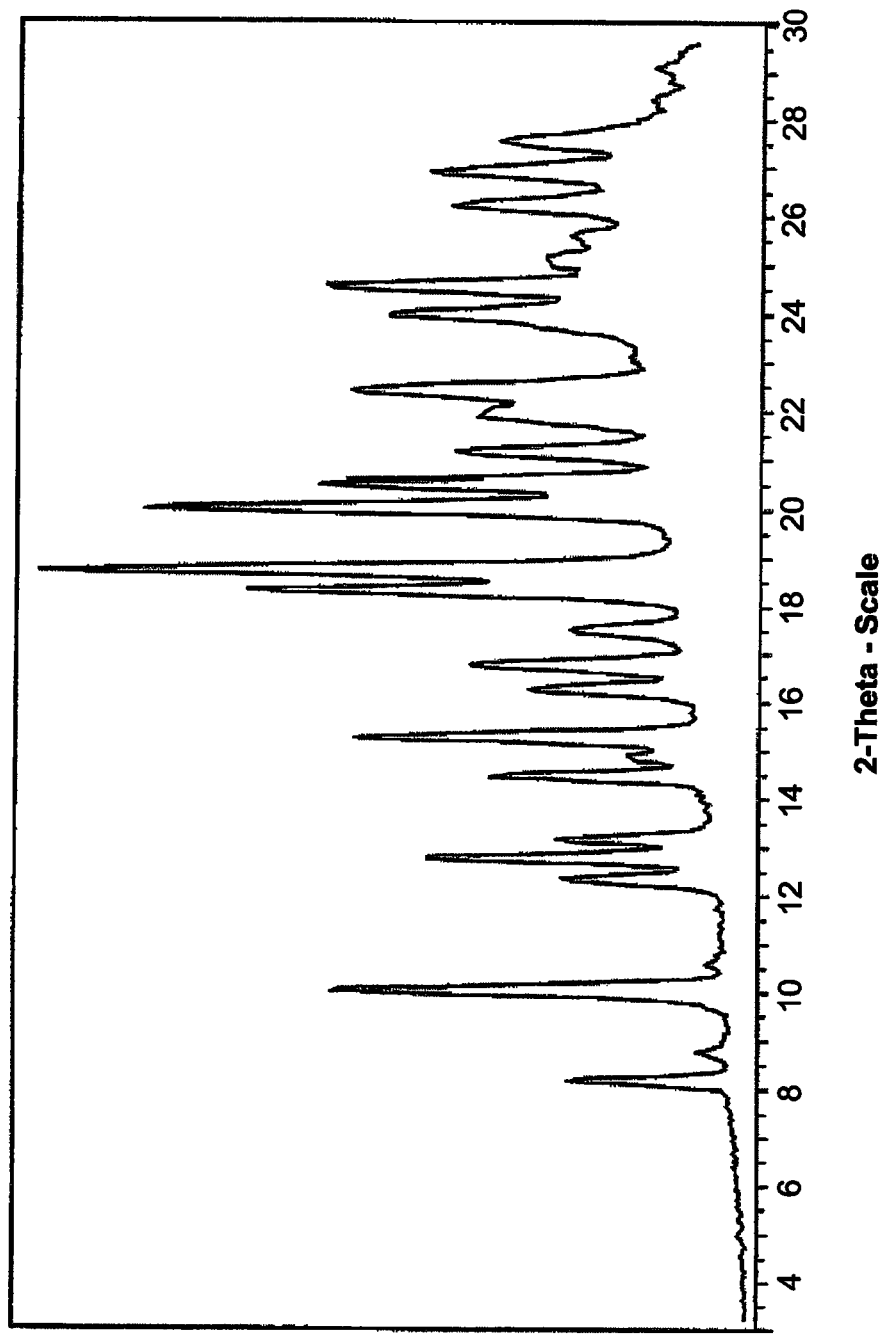
FIG. 33 is an experimental XRPD of Compound $1.H_2O$.
Figure 34:
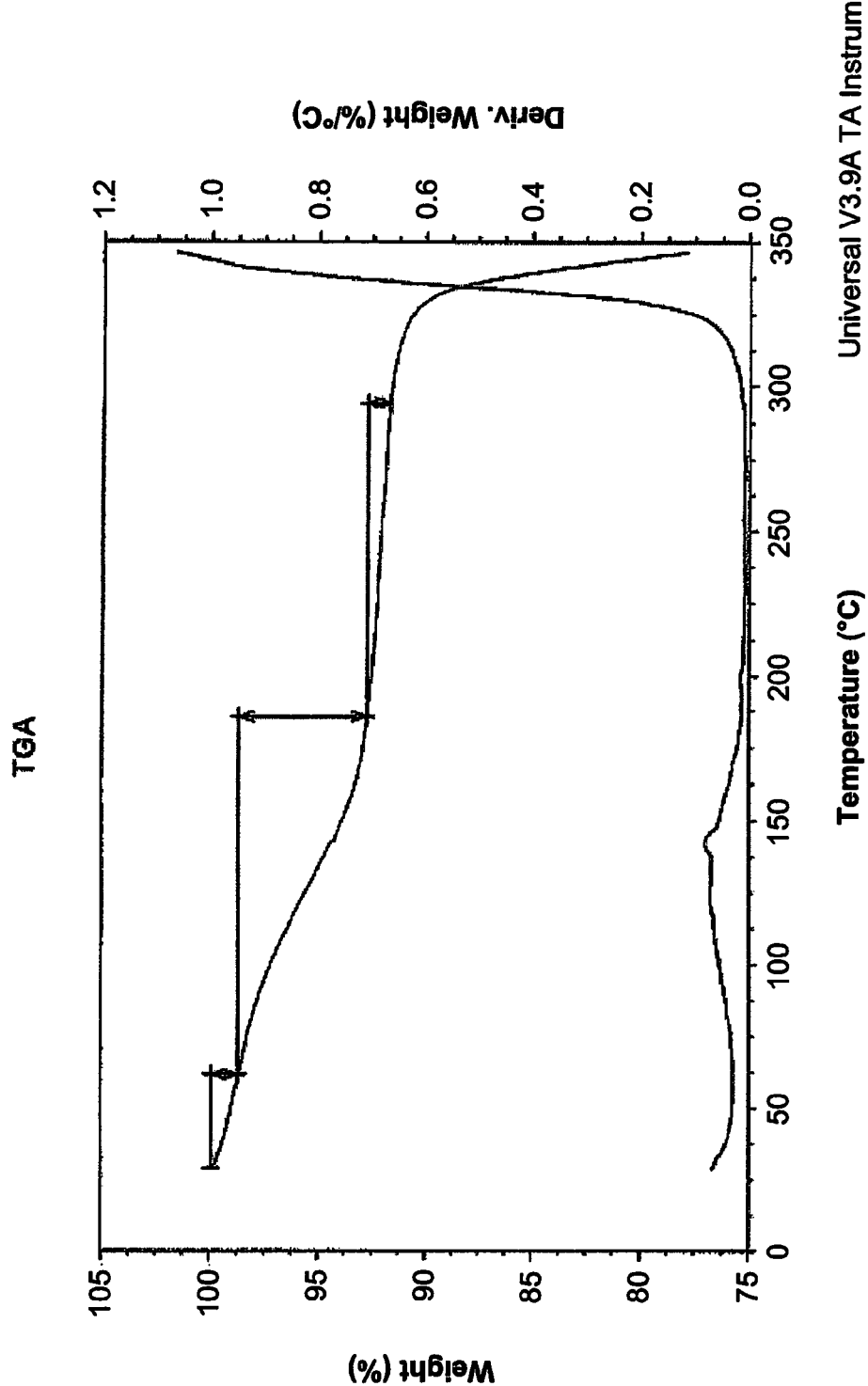
FIG. 34 is a TGA trace of Compound $1.H_2O$.
Figure 35:
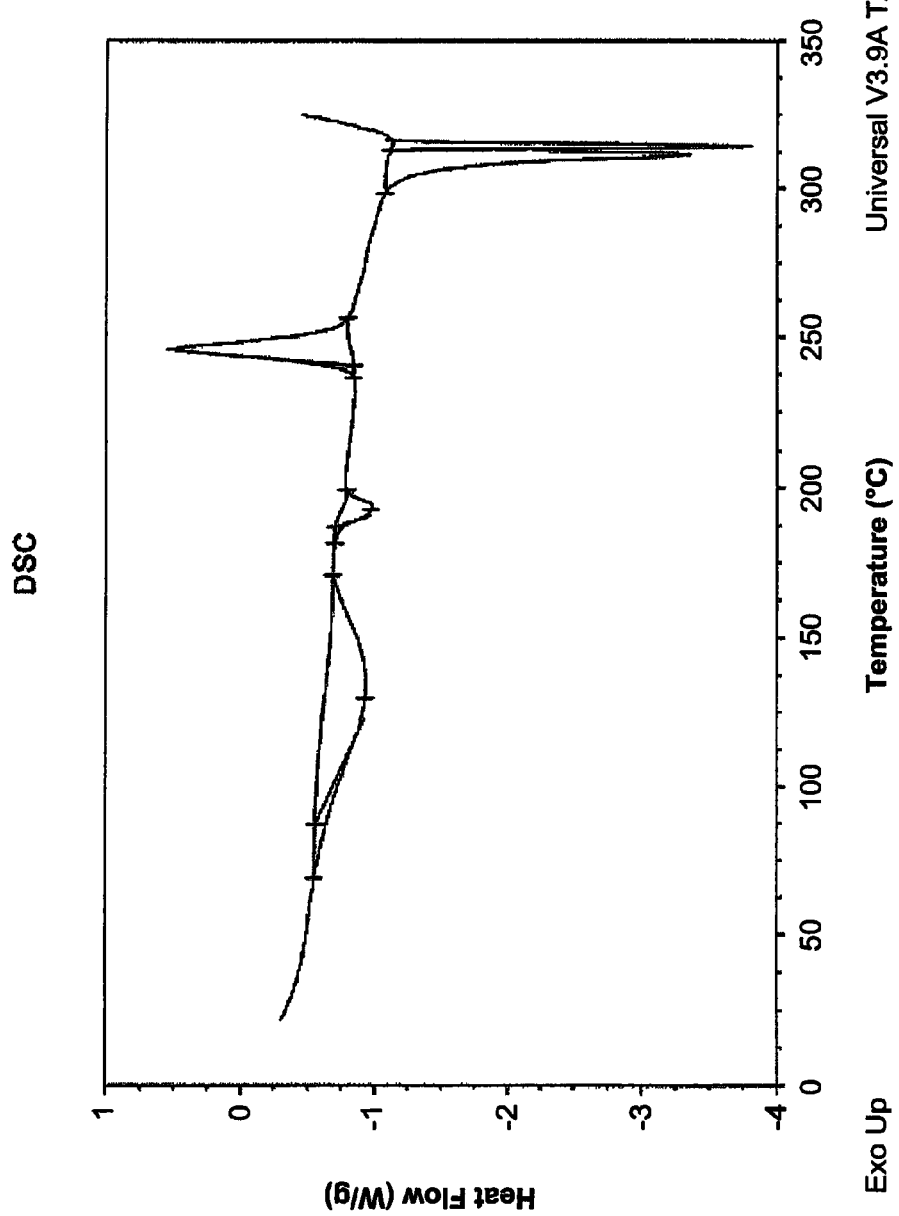
FIG. 35 is a DSC trace of Compound $1.H_2O$.

A sample of Form IX was analyzed using a plurality of analytical techniques. FIGS. 33, 34, and 35, respectively depict an experimental XRPD of Form IX, a TGA trace of Form IX, a DSC of form IX, each of which were obtained using the methods described above.

Example 10

Form X 10.0 g of Compound 1 and 70 ml isopropyl acetate were charged into a reactor. 5.25 g anhydrous benzenesulfonic acid was dissolved into 30 ml of isopropyl acetate using a 2$^{nd}$ reactor. The solution of benzenesulfonic acid was charged into the slurry of Compound 1. The resulting slurry was stirred at room temperature for 23 hrs and isolated by filtration. The cake was washed with isopropyl acetate and dried in a vacuum oven at 45° C.+/−5° C. to provide Form X.

Figure 36:
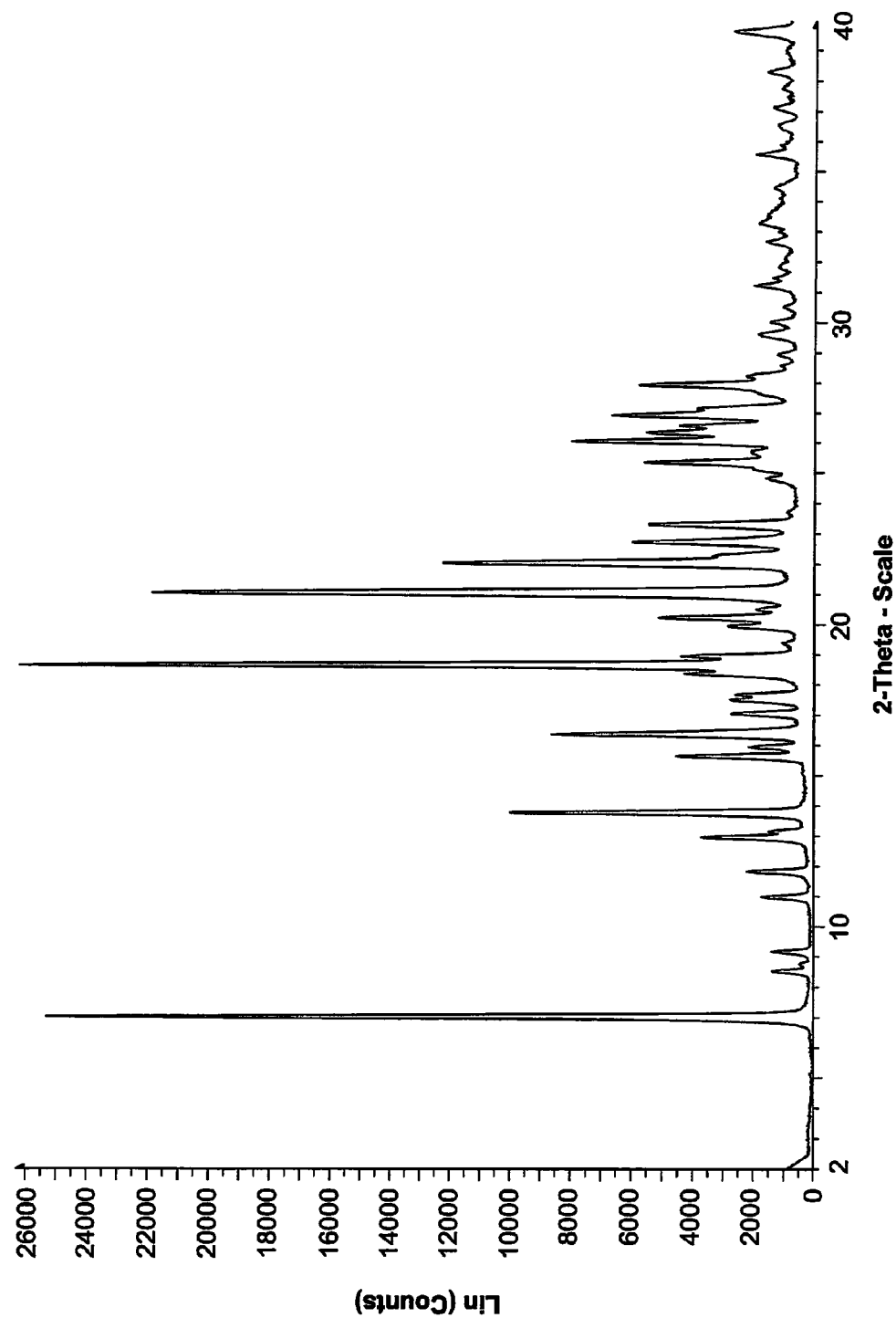
FIG. 36 is an experimental XRPD of Compound 1.Besylate Form A.

A sample of Form X was analyzed using a plurality of analytical techniques. FIGS. 36 and 37 depict an experimental XRPD of Form X and a DSC of Form X. The XRPD was recorded on a Corundum calibrated Bruker D8 Advance diffractometer with a Vantac line detector. The 2 Theta range was approximately 2 degrees to 40 degrees, with a step size of 0.014 degrees. The time per step was approximately 105 milliseconds. Cu Kα seal tube radiation was used at 40 kV, 40 mA under ambient conditions.

Example 11

Form XI 12.1 g of anhydrous Benzenesulfonic acid and 24.92 g Compound 1 was charged into reactor. 250 ml Acetonitrile was added. The resulting slurry was heated to 60° C. for 3 hrs. This mixture was cooled to room temperature. The slurry was filtered, and washed with acetonitrile. The material was re-suspended in the filtrate, and heated to 85° C. for 2 hrs, then cooled to room temperature and isolated by filtration. The wet cake was again re-suspended in 250 ml acetonitrile this time, and 12.0 g anhydrous benzenesulfonic acid was charged into the reactor. The resulting slurry was heated to 60° C. for 4 hrs followed by cooling to 40° C. for 2 hrs and then cooling to room temperature, and isolated by filtration. The cake was washed with acetonitrile and dried in a vacuum oven at 45° C.+/−5° C. to provide Form XI.

Figure 38:
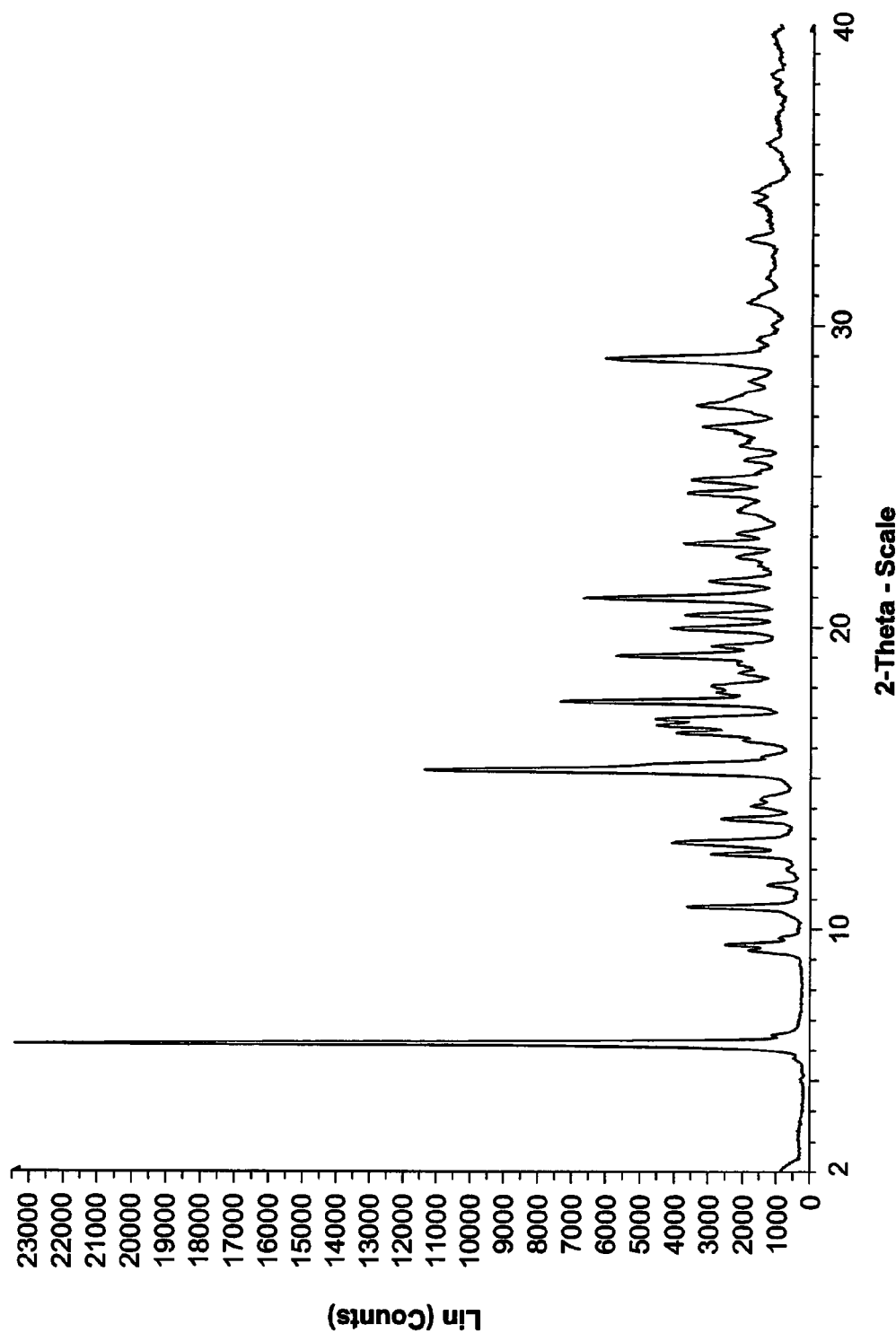
FIG. 38 is an experimental XRPD of Compound 1.Besylate Form B.

A sample of Form XI was analyzed using a plurality of analytical techniques. FIGS. 38 and 39 depict an experimental XRPD of Form XI and a DSC of Form XI, respectively. The XRPD was recorded on a Corundum calibrated Bruker D8 Advance diffractometer with Vantac line detector. The 2 Theta range was approximately 2 degrees to 40 degrees, with a step size of 0.014 degrees. The time per step was approximately 105 milliseconds. Cu Kα seal tube radiation was used at 40 kV, 40 mA under ambient conditions.

Example 12

Form XII 43.6 g of Benzenesulfonic acid monohydrate was charged into reactor A. 2.00 L of Toluene (20.0 vol) was added to reactor A. The resulting mixture was heated to reflux, and concentrated to ½ volume (1.00 L). The concentrated mixture was cooled to 75° C.+/−2.5° C., followed by the addition of 1.00 L Toluene (10.0 vol). This mixture was cooled to 40° C.+/−2.5° C. 100 g of Compound 1 (1.0 eq) was added to reactor B followed by the addition of the Benzenesulfonic acid/Toluene solution from reactor A. The resulting slurry was heated to 85° C.+/−2.5° C. and stirred for a total of 18 hours at 85° C.+/−2.5° C. The slurry was cooled to 20.0° C.+/−5° C., solids were filtered, and washed with Toluene (1.00 L, 10 vol). The material was dried in a vacuum oven at 45° C.+/−5° C. to provide Form XII.

Figure 40:
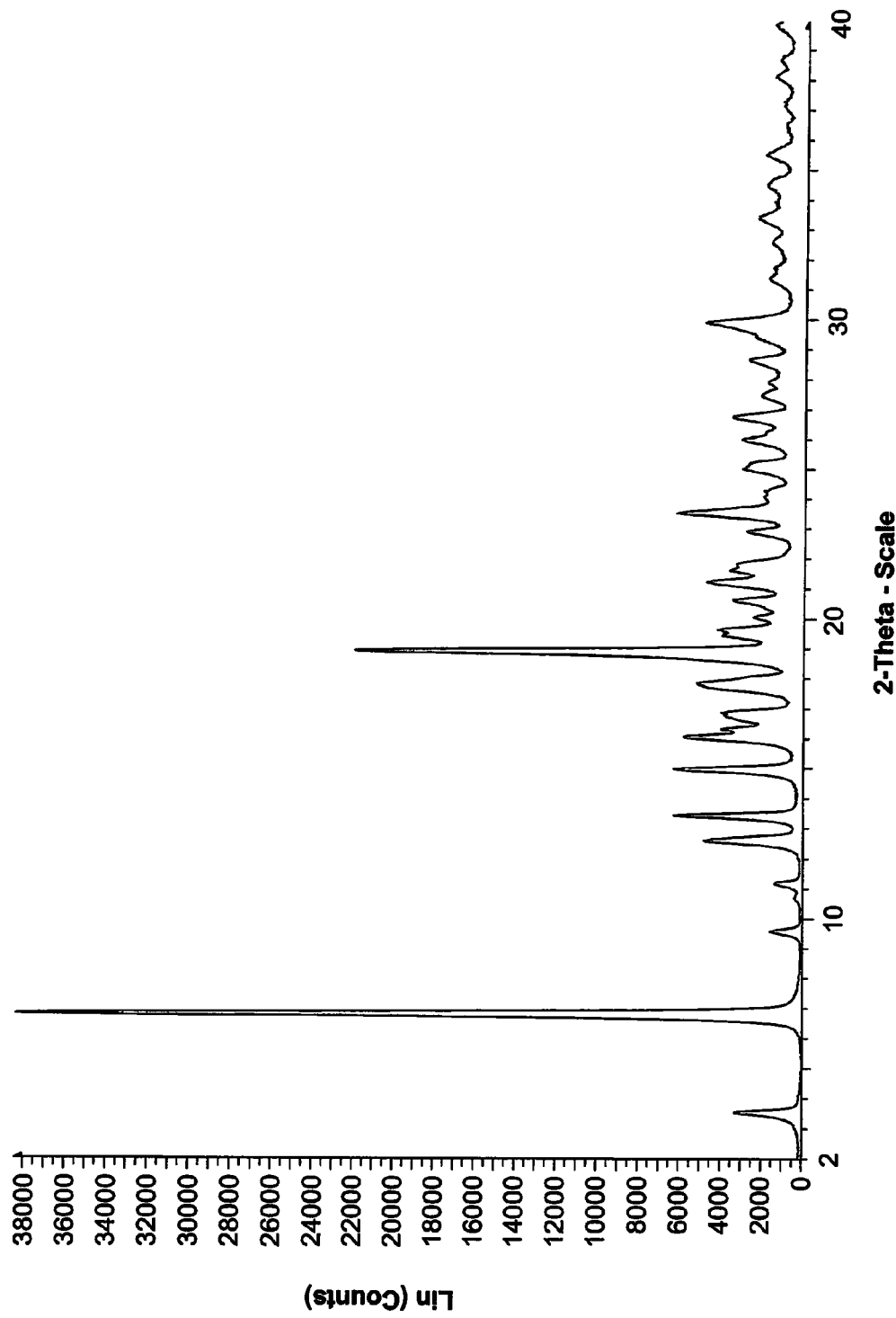
FIG. 40 is an experimental XRPD of Compound 1.Besylate Form D.
Figure 42:
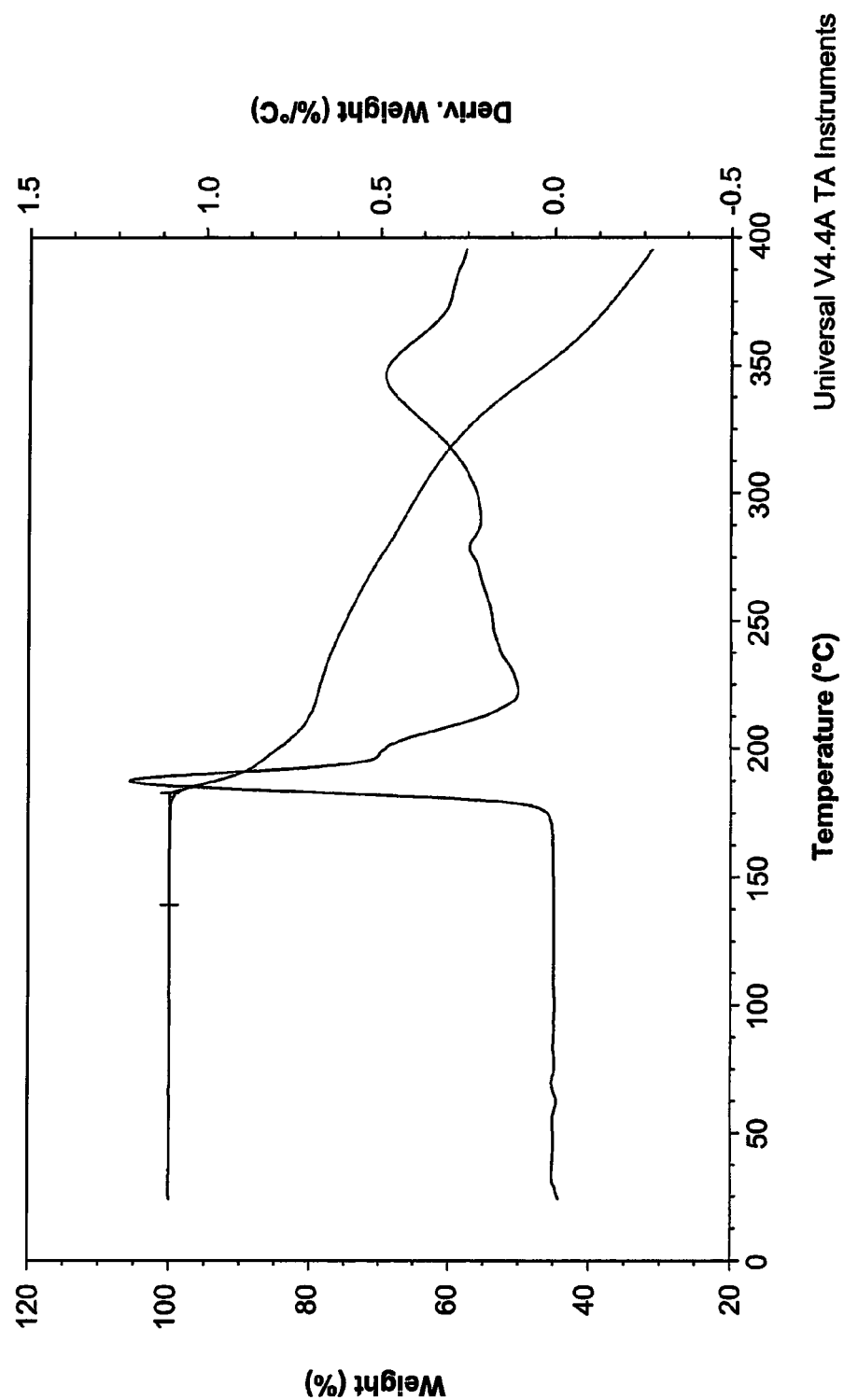
FIG. 42 is a TGA trace of Compound 1.Besylate Form D.

A sample of Form XII was analyzed using a plurality of analytical techniques. FIGS. 40-42 depict an experimental XRPD of Form XII, a DSC of Form XII and a TGA of Form XII, respectively. The XRPD was recorded on a Corundum calibrated Bruker D8 Advance diffractometer with Vantac line detector. The 2 Theta range was approximately 2 degrees to 40 degrees, with a step size of 0.014 degrees. The time per step was approximately 105 milliseconds. Cu Kα seal tube radiation was used at 40 kV, 40 mA under ambient conditions. The TGA was recorded as described above except that data was recorded out to 350° C.

Example 13

Form XIII

Compound 1 was added to reactor A with 10 vol of isopropyl acetate. In a separate reactor, benzenesulfonic acid monohydrate (0.95 eq based on anhydrous Benzenesulfonic acid) was dissolved with 10 vol of isopropyl acetate. The benzenesulfonic acid solution was then added to reactor A. The resulting slurry was heated to 30° C.+/−2.5° C. and stirred for 24 h. The mixture was cooled to 20.0° C.+/−5° C., the solids filtered and washed with 5 vol isopropyl acetate. The washed solids were dried at 30° C. in a fluidized bed with N$_2$ bleed to provide Form XIII.

Figure 43:
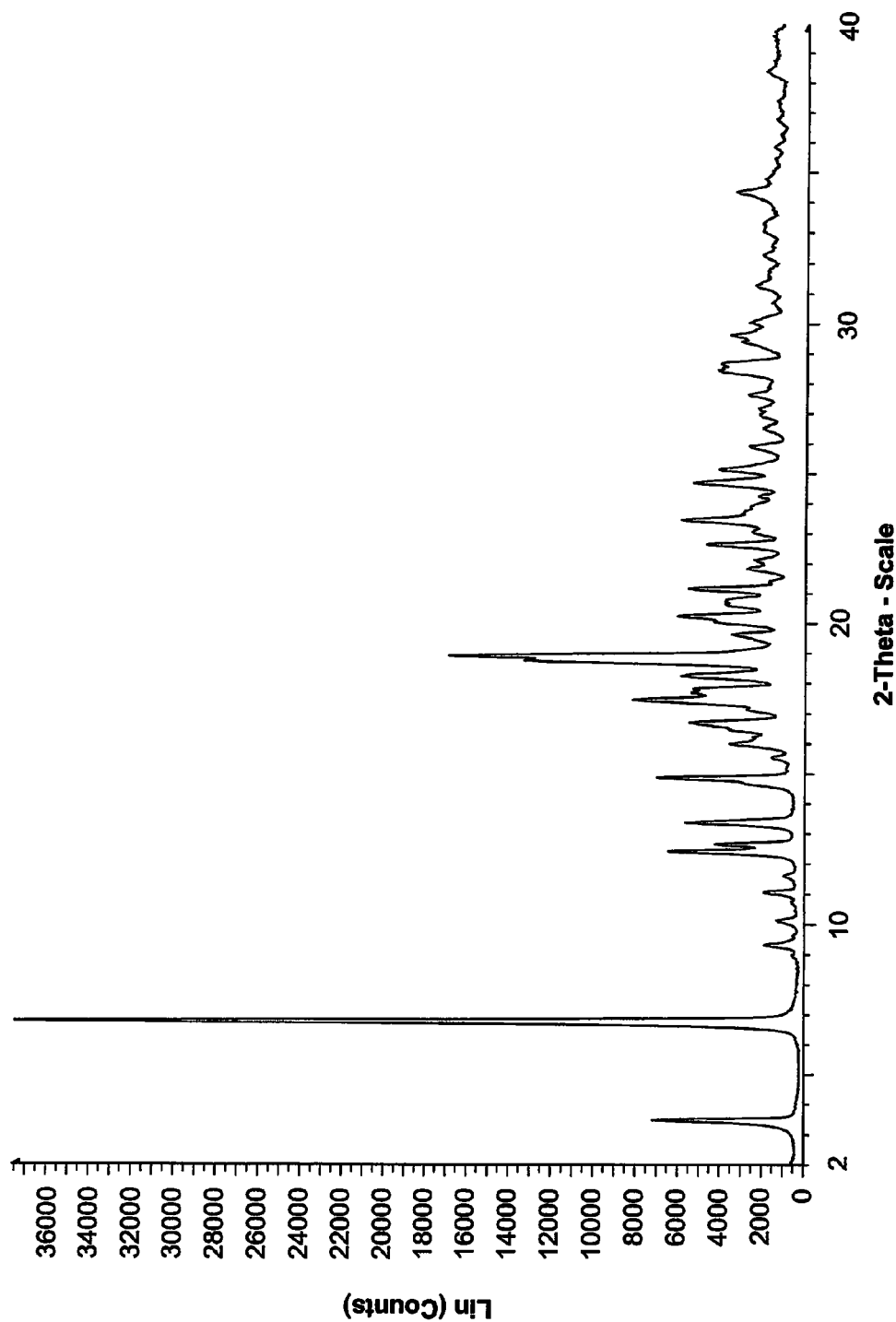
FIG. 43 is an experimental XRPD of Compound 1.Besylate Form E.
Figure 45:
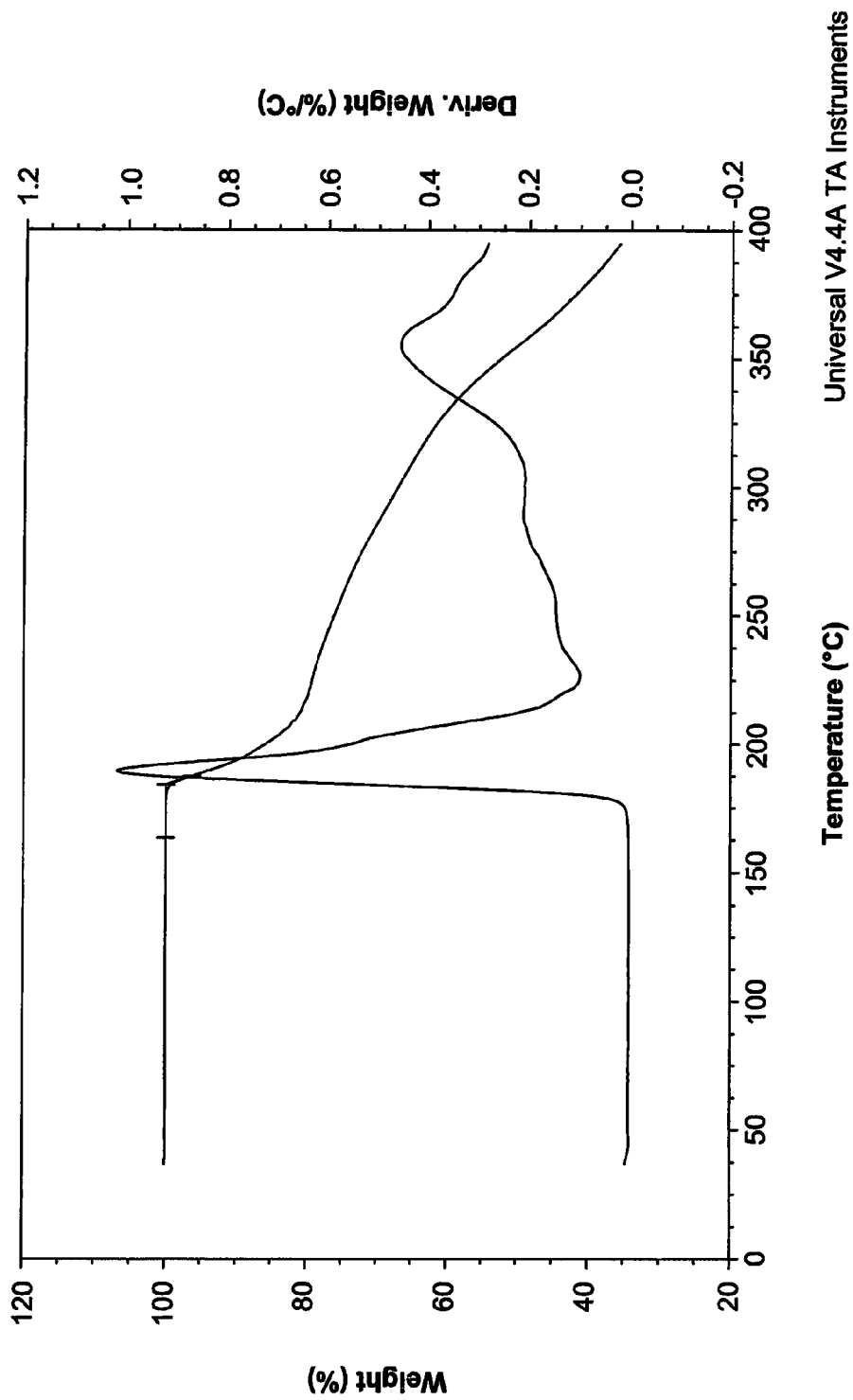
FIG. 45 is a TGA trace of Compound 1.Besylate Form E.
Figure 46:
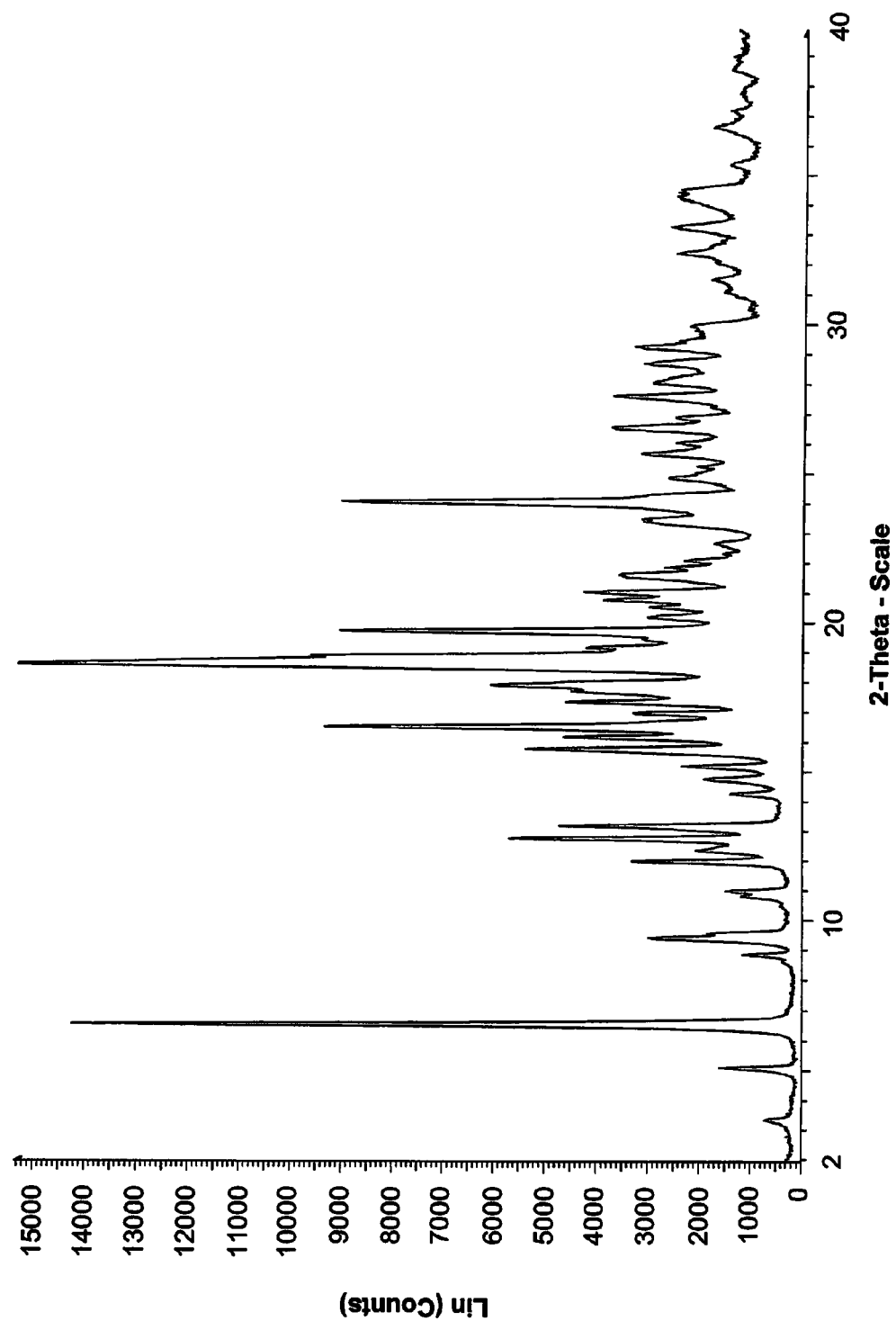
FIG. 46 is an experimental XRPD of Compound 1.Besylate Form F.

A sample of Form XIII was analyzed using a plurality of analytical techniques. FIGS. 43-45 depict an experimental XRPD of Form XIII, a DSC of Form XIII and a TGA of Form XIII, respectively. The XRPD was recorded on a Corundum calibrated Bruker D8 Advance diffractometer with Vantac line detector. The 2 Theta range was approximately 2 degrees to 40 degrees, with a step size of 0.014 degrees. The time per step was approximately 105 milliseconds. Cu Kα seal tube radiation was used at 40 kV, 40 mA under ambient conditions. The TGA was recorded as described above except that data was recorded out to 350° C.

Example 14

Form XIV 15.0 g of Compound 1 and 120 ml 2-methyltetrahydrofuran were charged to reactor A. 7.25 g benzenesulfonic acid hydrate and 180 ml isopropyl acetate was charged to reactor B. Reactor B contents were dried via zoetrope (solvent swap with fresh isopropyl acetate) twice to provide a dry solution of benzenesulfonic acid in isopropyl acetate. Reactor B contents were charged into reactor A at ambient temperature. The resulting slurry was heated to reflux (homogeneous solution attained), and then cooled immediately to ambient temperature to afford a slurry. The slurry was concentrated under reduced pressure to ½ volume, followed by addition of isopropyl acetate to achieve the original volume. The concentration and suspension in isopropyl acetate was repeated followed by concentration to ½ volume, filtration, and a washed with isopropyl acetate. The cake was dried in a vacuum oven at 50° C. to provide Form XIV.

Figure 48:
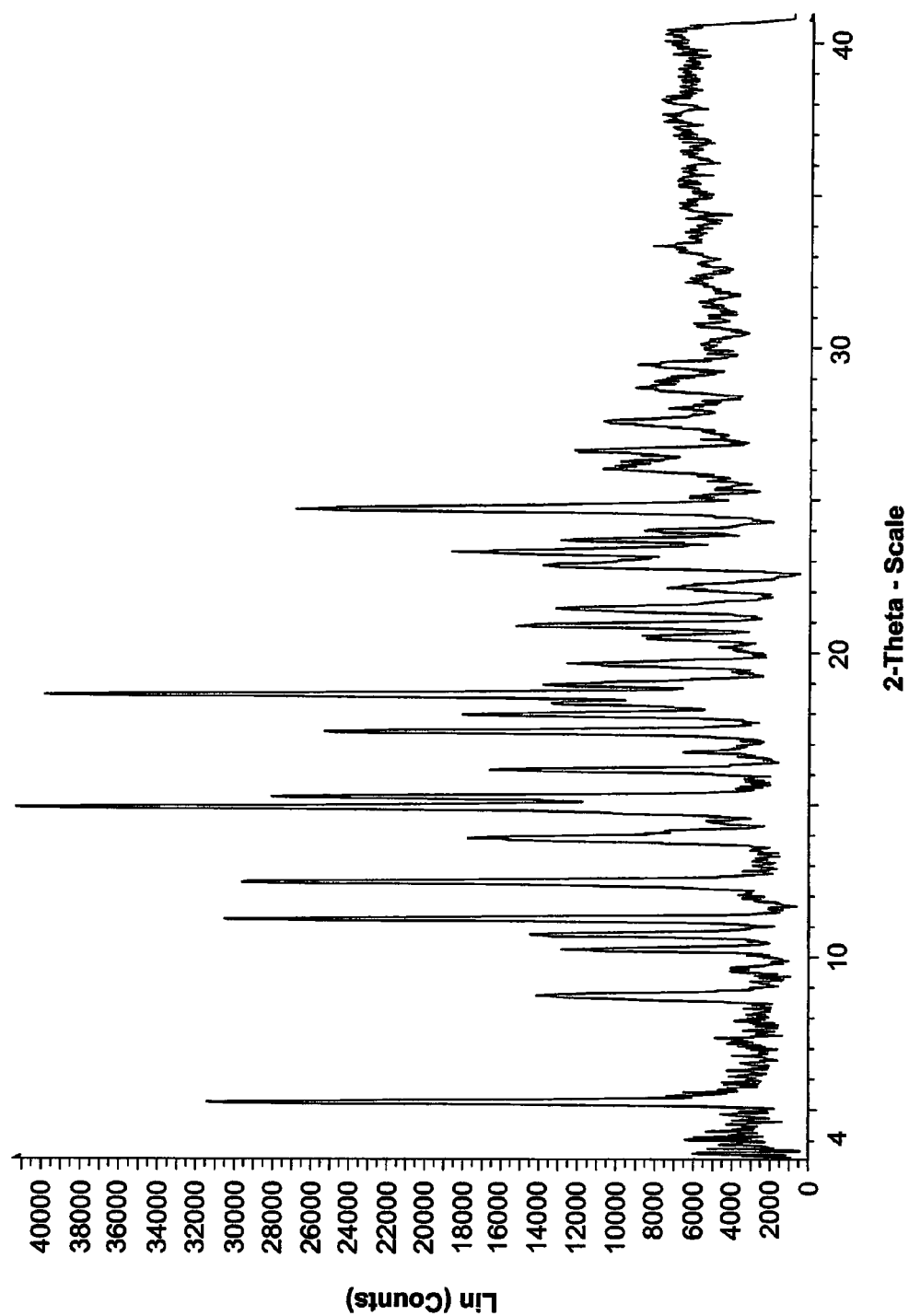
FIG. 48 is an experimental XRPD of Compound 1.Besylate with a ratio of Compound 1 to besylate of 2:1.

A sample of Form XIV was analyzed using a plurality of analytical techniques. FIGS. 47 and 48 depict an experimental XRPD of Form XIV and a DSC of Form XIV, respectively. The XRPD was recorded on a Corundum calibrated Bruker D8 Advance diffractometer with Vantac line detector. The 2 Theta range was approximately 2 degrees to 40 degrees, with a step size of 0.014 degrees. The time per step was approximately 105 milliseconds. Cu Kα seal tube radiation was used at 40 kV, 40 mA under ambient conditions.

Example 15

Form XV 4.94 g of Compound 1 and 24.7 ml isopropyl acetate were charged to reactor A. 1.195 g (0.6 eq) benzenesulfonic acid hydrate and 24.7 ml isopropyl acetate was charged to reactor B. Reactor B contents were charged to reactor A at ambient temperature. The resulting slurry was stirred at room temperature for 23 hrs followed by filtration and a wash with isopropyl acetate. The cake was dried in a vacuum oven to provide Form XV.

Figure 49:
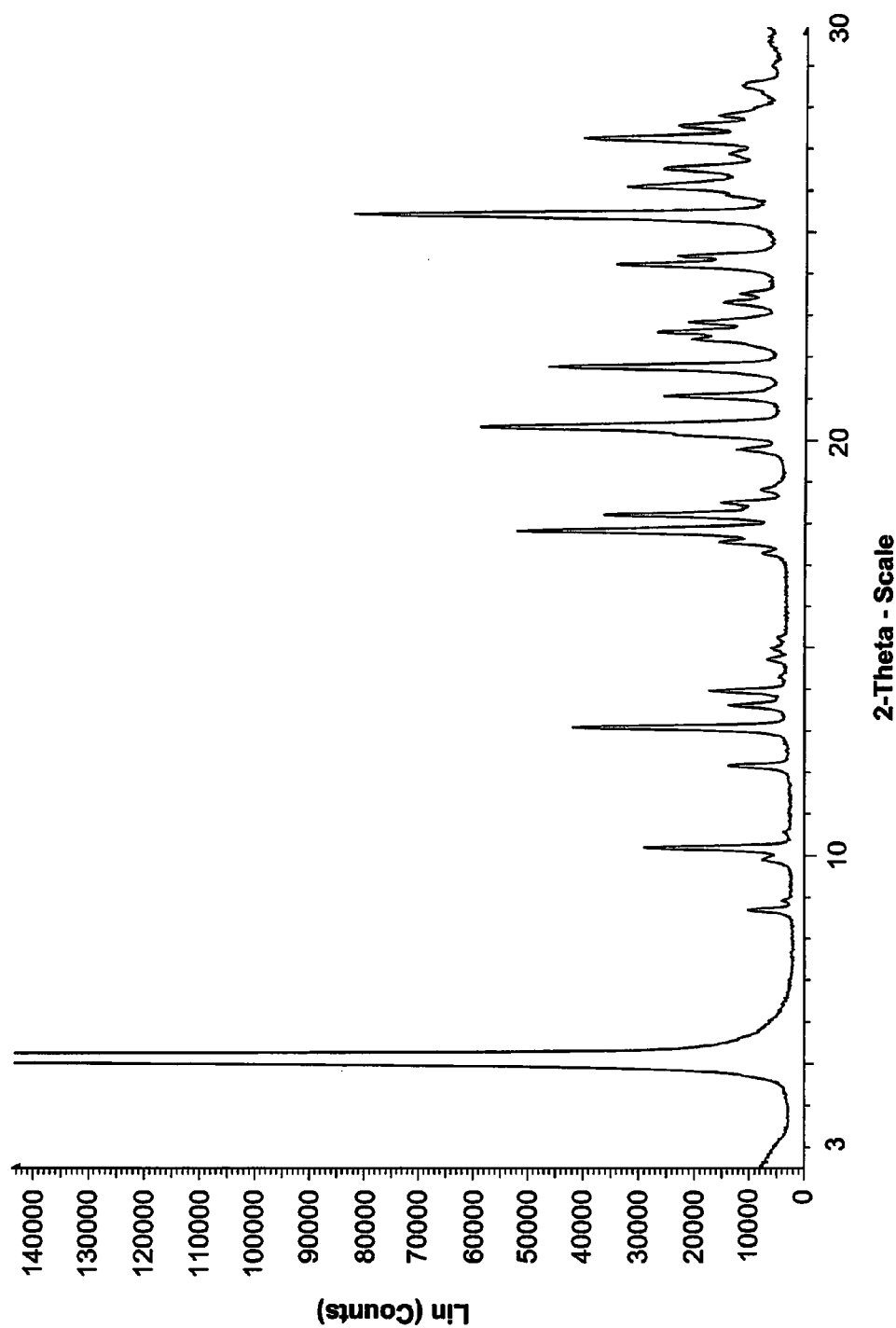
FIG. 49 is an experimental XRPD of Compound 1.Besylate.H$_2$O with a ratio of Compound 1 to besylate to water of 1:2:1.

A sample of Form XV was analyzed using a plurality of analytical techniques. FIG. 49 depicts an experimental XRPD of Form XV. The XRPD was recorded on a Corundum calibrated Bruker D8 Advance diffractometer with Vantac line detector. The 2 Theta range was approximately 2 degrees to 40 degrees, with a step size of 0.014 degrees. The time per step was approximately 105 milliseconds. Cu Kα seal tube radiation was used at 40 kV, 40 mA under ambient conditions.

Example 16

Form XVI 13.15 g of Compound 1.besylate and 98.6 ml ethyl acetate were charged to reactor A. 21.04 g benzenesulfonic acid hydrate and 98.6 ml isopropyl acetate was charged to reactor B. Reactor B contents were charged to reactor A at ambient temperature. The resulting slurry was stirred at room temperature for 18 hrs followed by filtration and a wash with isopropyl acetate. The cake was dried in a vacuum oven at 35° C. to provide Form XVI.

Figure 50:
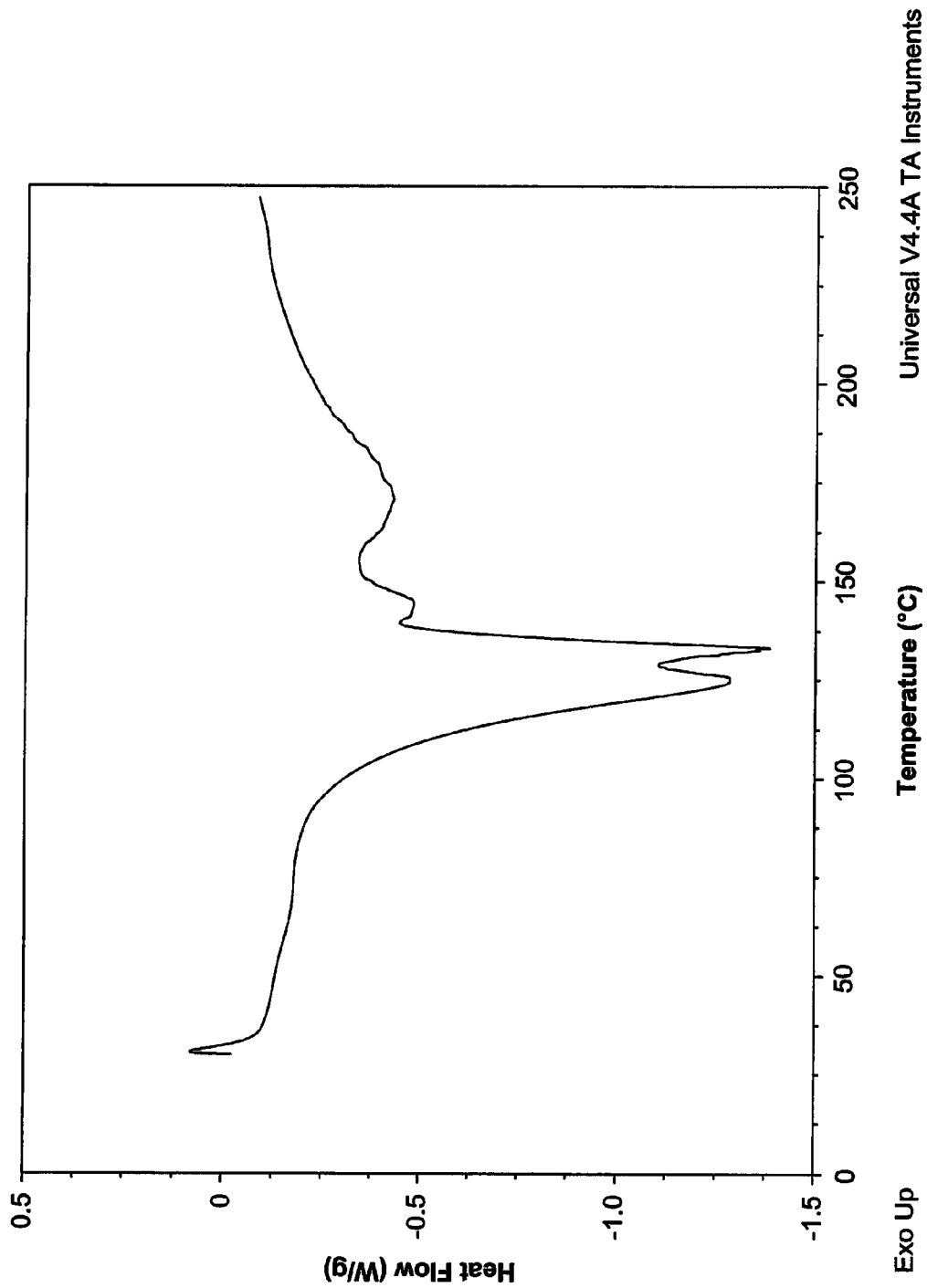
FIG. 50 is a DSC trace of Compound 1.Besylate.H$_2$O.
Figure 52:
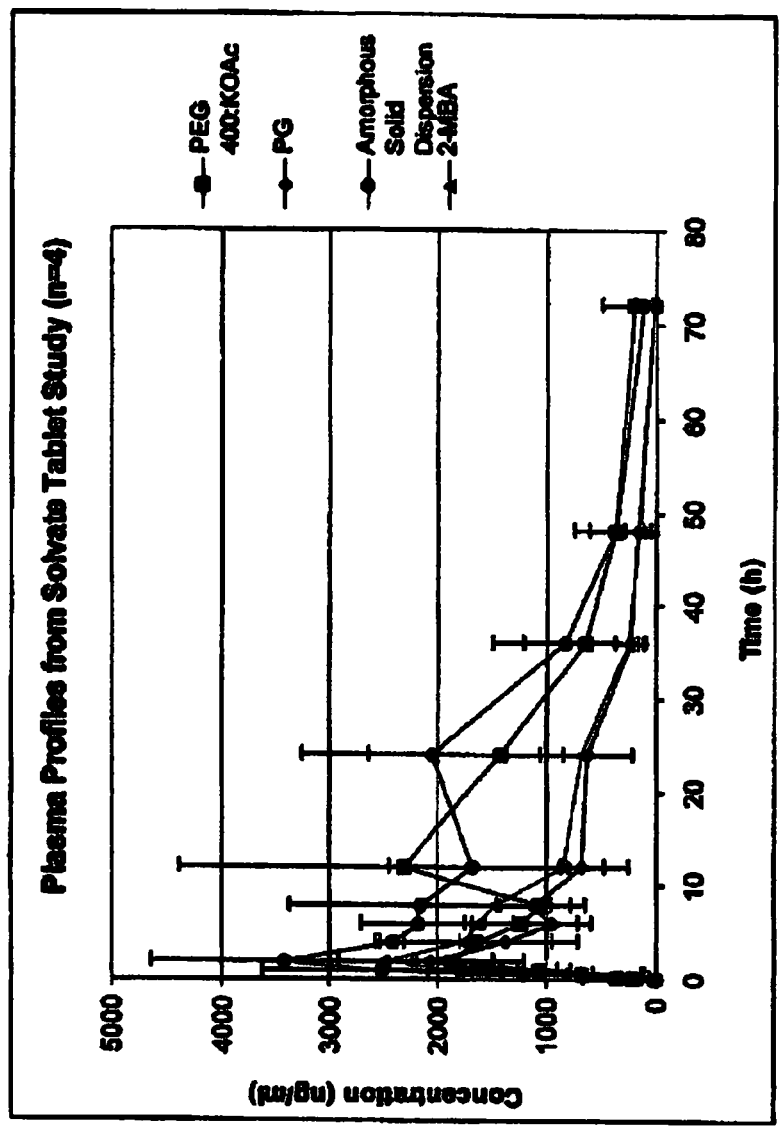
FIG. 52 depicts a graph of plasma levels of dosed dogs with various solid forms of Compound 1.

A sample of Form XVI was analyzed using a plurality of analytical techniques. FIGS. 50-52 respectively depict an experimental XRPD of Form XVI, a TGA trace of Form XVI, a DSC of Form XVI, and a DVS of Form XVI, each of which were obtained using the methods described above. The XRPD was recorded on a Corundum calibrated Bruker D8 Advance diffractometer with Vantac line detector. The 2 Theta range was approximately 3 degrees to 41 degrees, with a step size of 0.014 degrees. The time per step was approximately 105 milliseconds. Cu Kα seal tube radiation was used at 40 kV, 35 mA under ambient conditions. The TGA was recorded as described above except that data was recorded out to 350° C.

Example 17

NMR

The solution NMR spectra recorded by dissolving the materials in Examples 10-17 exhibits the following peaks.

$^1$H NMR (500 MHz, d6-DMSO): 12.99 (d, J=5 Hz, 1H); 11.91 (s, 1H); 11.43 (br, 2H); 8.92 (d, J=10 Hz, 1H); 8.39 (d, J=10 Hz, 1H); 7.79 (m, 2H); 7.77 (d, J=10 Hz, 2H); 7.53 (m, 1H); 7.42 (m, 3H); 7.23 (s, 1H); 7.21 (s, 1H); 1.43 (d, J=15 Hz, 18H).

Example 18

Plasma Exposure of Solid Forms

Tablets of a solid dispersion of Compound 1, as well as tablets of solid forms I, II, and III, were administered to 4 dogs to evaluate the plasma exposure of Compound 1. The compounds were dosed as 10 mg/kg. The results of the study are provided in FIG. 53 and the following table.

| Tablet Description | Dose (mg/kg) | AUCinf (hr * ug/ml) | | Cmax (ug/ml) | |
|---|---|---|---|---|---|
| Solid dispersion Tablet | 10 | 38.3 | 13.5 | 2.5 | 0.8 |
| Form I Tablet | 10 | 31.5 | 12.2 | 2.1 | 0.8 |
| Form II Tablet | 10 | 71.5 | 53.5 | 3.8 | 1.1 |
| Form III Tablet | 10 | 85.5 | 31.3 | 4.3 | 1.3 |

| Tablet Description | Tmax (hr) | | Half-life (hr) | | % F | |
|---|---|---|---|---|---|---|
| Solid Dispersion Tablet | 1.8 | 0.5 | 9.6 | 1.6 | 15.3 | 5.4 |
| Form I Tablet | 1.8 | 0.5 | 9.1 | 1.2 | 12.7 | 4.9 |
| Form II Tablet | 7.5 | 5.3 | 15.7 | 5.8 | 28.6 | 21.4 |
| Form III Tablet | 8.0 | 10.7 | 12.6 | 1.5 | 34.2 | 12.5 |

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating a CFTR mediated disease in a mammal comprising administering a solid form of a compound selected from Compound 1.2-methylbutyric acid, Compound 1.propylene glycol, Compound 1.PEG 400.KOAc, Compound 1.lactic acid, Compound 1.isobutyric acid, Compound 1.propionic acid, Compound 1.2-propanol, Compound 1.besylate, and Compound 1.besylate.H$_2$O, wherein said disease is selected from cystic fibrosis, hereditary emphysema, COPD, and dry-eye disease, and Compound 1 is N-[2,4-bis(1,1-dimethylethyl)-5-hydroxyphenyl]-1,4-dihydro-4-oxoquinoline-3-carboxamide.

2. The method according to claim 1, wherein said disease is cystic fibrosis.

3. The method according to claim 1, further comprising administering an additional therapeutic agent.

* * * * *